(12) United States Patent
Moussy et al.

(10) Patent No.: US 8,962,665 B2
(45) Date of Patent: Feb. 24, 2015

(54) THIAZOLE AND OXAZOLE KINASE INHIBITORS

(75) Inventors: Alain Moussy, Paris (FR); Abdellah Benjahad, Champigny sur Marne (FR); Jason Martin, L'Hay les Roses (FR); Emmanuel Chevenier, Les Ulis (FR); Didier Pez, Nievroz (FR); Franck Sandrinelli, Balan (FR); Willy Picoul, Lyon (FR)

(73) Assignee: AB Science, Paris (FR)

( * ) Notice: Subject to any disclaimer, the term of this patent is extended or adjusted under 35 U.S.C. 154(b) by 148 days.

(21) Appl. No.: 13/521,676

(22) PCT Filed: Jan. 12, 2011

(86) PCT No.: PCT/EP2011/050312
§ 371 (c)(1),
(2), (4) Date: Oct. 23, 2012

(87) PCT Pub. No.: WO2011/086085
PCT Pub. Date: Jul. 21, 2011

(65) Prior Publication Data
US 2013/0035331 A1 Feb. 7, 2013

Related U.S. Application Data

(60) Provisional application No. 61/294,226, filed on Jan. 12, 2010.

(51) Int. Cl.
*A61K 31/42* (2006.01)
*C07D 413/00* (2006.01)
*C07D 413/14* (2006.01)
*C07D 413/12* (2006.01)
*C07D 417/14* (2006.01)

(52) U.S. Cl.
CPC ............ *C07D 413/14* (2013.01); *C07D 413/12* (2013.01); *C07D 417/14* (2013.01)
USPC ........................................ 514/374; 548/215

(58) Field of Classification Search
USPC .......................................... 514/374; 548/215
See application file for complete search history.

(56) References Cited

U.S. PATENT DOCUMENTS

| | | | |
|---|---|---|---|
| 3,740,420 A | 6/1973 | Herschler et al. |
| 3,743,727 A | 7/1973 | Herschler |
| 3,989,816 A | 11/1976 | Rajadhyaksha |
| 4,322,433 A | 3/1982 | Leslie et al. |
| 4,379,454 A | 4/1983 | Campbell et al. |
| 4,405,616 A | 9/1983 | Rajadhyaksha |
| 4,411,893 A | 10/1983 | Johnson et al. |
| 4,460,372 A | 7/1984 | Campbell et al. |
| 4,575,515 A | 3/1986 | Sandborn |
| 4,615,699 A | 10/1986 | Gale et al. |
| 5,556,611 A | 9/1996 | Biesalski |
| 5,906,202 A | 5/1999 | Schuster et al. |
| 2008/0207617 A1 | 8/2008 | Miwa et al. |

FOREIGN PATENT DOCUMENTS

| | | |
|---|---|---|
| EP | 1854793 | 11/2007 |
| JP | 2004/039782 | 5/2004 |
| WO | 02/32861 | 4/2002 |
| WO | 02/092599 | 11/2002 |
| WO | 03/024931 | 3/2003 |
| WO | 03/024969 | 3/2003 |
| WO | 03/035009 | 5/2003 |
| WO | 03/037347 | 5/2003 |
| WO | 03/057690 | 7/2003 |
| WO | 03/099771 | 12/2003 |
| WO | 2004/005281 | 1/2004 |
| WO | 2004/016597 | 2/2004 |
| WO | 2004/018419 | 3/2004 |
| WO | 2004/039782 | 5/2004 |
| WO | 2004/043389 | 5/2004 |
| WO | 2004/046120 | 6/2004 |
| WO | 2004/058749 | 7/2004 |
| WO | WO 2007/149395 | 12/2007 |
| WO | 2008/016665 | 2/2008 |
| WO | WO 2009/076140 | 6/2009 |
| WO | WO 2011/075517 | 6/2011 |

OTHER PUBLICATIONS

Yamamoto et al., "Activating mutation of D835 within the activation loop of FLT3 in human hematologic malignancies", Blood, 2001, vol. 97, No. 8, pp. 2434-2439.
Braselmann et al., "R406, an Orally Available Spleen Tyrosine Kinase Inhibitor Blocks Fc Receptor Signaling and Reduces Immune Complex-Mediated Inflammation", The Journal of Pharmacology and Experimental Therapeutics, 2006, vol. 319, No. 3, pp. 998-1008.
Casteran et al., Analysis of the Mitogenic Pathway of the FLT3 Receptor and Characterization in its C Terminal Region of a Specific Binding Site for the PI3'Kinase, Cellular and Molecular Biology. 1994, vol. 40, No. 3, pp. 443-456.
Cooper et al., "Interaction of Surfactants with Epidermal Tissues: Physicochemical Aspects", Surfactant Science Series, 1987, vol. 16, pp. 195-210.
Wong et al., "Targeting Syk as a treatment for allergic and autoimmune disorders", Expert Opin. Investig. Drugs, 2004, vol. 13. No. 7, pp. 743-762.

(Continued)

*Primary Examiner* — James O. Wilson
*Assistant Examiner* — Oluwafemi Masha
(74) *Attorney, Agent, or Firm* — Hamre, Schumann, Mueller & Larson, P.C.

(57) ABSTRACT

The present invention is concerned with substituted azole derivatives that selectively modulate, regulate, and/or inhibit signal transduction mediated by certain native and/or mutant proteine kinases implicated in a variety of human and animal diseases such as cell proliferative, metabolic, allergic, and degenerative disorders. In particular, several of these compounds are potent and selective Flt-3 inhibitors or/and syk inhibitors.

15 Claims, No Drawings

(56) References Cited

OTHER PUBLICATIONS

Rosnet et al., "Isolation and Chromosomal Localization of a Novel FMS-like Tyrosine Kinase Gene", Genomics, 1990, vol. 9, pp. 380-385.

Denton et al.,"5-Substituted, 6-Substituted, and Unsubstituted 3-Heteroaromatic Pyradine Analogues of Nicotine as Selective Inhibitors of Cytochrome P-450 2A6", J. Med. Chem., 2005, vol. 48, pp. 224-239.

Shen et al., "Discovery of Biaryl Anthranilides as Full Agonists for the High Affinity Niacin Receptor", J. Med. Chem., 2007, vol. 50, pp. 6303-6306.

Mamane et al., "Convenient Access to New Chiral Ferroceno-(iso)quinolines" J. Org. Chem., 2005, vol. 70, pp. 8220-8223.

Beslu et al., "Phosphatidylinositol-3'Kinase is not required for Mitogenesis or Internalization of the Flt3/Flk2 Receptor Tyrosine Kinase", The Journal of Biological Chemistry, 1996, vol. 271, No. 33, pp. 20075-20081.

Yamada et al., "IL-1 Induced Chemokine Production Through the Association of Syk with TNF Receptor-Associated Factor-6 in Nasal Fibroblast Lines", The Journal of Immunology, 2001, vol. 167, pp. 283-288.

Takada et al., "TNF Activates Syk Protein Tyrosine Kinase Leading to TNF-Induced MAPK Activation, NF-kB Activation, and Apoptosis", The Journal of Immunology, 2004, vol. 173, pp. 1066-1077.

Dugard et al., "Effects of Ionic Surfactants on the Permeability of Human Epidermis: an Electrometric Study", The Journal of Investigative Dermatology, 1973, vol. 60, No. 5, pp. 263-269.

Nakao et al., "Internal Tandem duplication of the flt3 gene found in acute myeloid leukemia", Leukemia, 1996, vol. 10, pp. 1911-1918.

Diederich et al., "Metal-catalyzed Cross-coupling Reactions", Wiley-VCH, 1998, pp. 1-270.

Hannum et al., "Ligand for FLT3/FLK2 receptor tyrosine kinase regulates growth of haematopoietic stem cells and is encoded by variant RNAs", Letters to Nature, 1994, vol. 368, pp. 643-648.

Okamura et al., "Identification of Seven Genes regulated by Wild-Type p53 in a Colon Cancer Cell Line Carrying a Well-Controlled Wild-Type p53 Expression System", Oncology Research, 1999, vol. 11, pp. 281-285.

Hicks et al. "Synthesis of Multitopic Verdazyl Radical Ligands. Paramagnetic Supramolecular Synthons", Organic Letters, 2004, vol. 6, No. 12, pp. 1887-1890.

Besselievre et al., "Stereoselective Direct Copper-Catalyzed Alkenylation of Oxazoles with Bromoalkenes", Organic Letters, 2008, vol. 10, No. 18, pp. 4029-4032.

Matsuyama et al., "Nickel-Catalyzed Direct Alkynylation of Azoles with Alkynyl Bromides", Organic Letters, 2009, vol. 11, No. 18, pp. 4156-4159.

Hudlicky, "Reductions in Organic Chemistry", John Wiley and Sons, 1984, pp. 1-322.

Nairn, "Solutions, Emulsions, Suspensions and Extractives", Remington's Pharmaceutical Sciences, 1980, 6th edition, chapter 83, pp. 1438-1462.

Sekura et al., "The Percutaneous Absorption of Alkyl Methyl Sulfoxides", Pharmacology of the Skin, Advances in Biology of Skin, vol. 12, chapter 17, pp. 257-269.

Besselievre et al., "C-H Bond Activation: A Versatile Protocol for the Direct Arylation and Alkenylation of Oxazoles", Synthesis, 2009, No. 20, pp. 3511-3520.

van Leusen et al.. "A Novel and Efficient Synthesis of Oxazoles from Tosylmethylisocyanide and Carbonyl Compounds", Tetrahedron Letters, 1972, No. 23, pp. 2369-2372.

Coleridge et al., "Negishi Coupling of 2-pyridylzinc bromide-paradigm shift in cross-coupling chemistry?", Tetrahedron Letters, 2010, No. 51, pp. 357-359.

Casteran et al., Analysis of the Mitogenic Pathway of the FLT3 Receptor and Characterization in its C Terminal Region of a Specific Binding Site for the PI3'Kinase, Cellular and Molecular Biology, 1994, vol. 40, No. 3. pp. 443-456.

Wong et al., "Targeting Syk as a treatment for allergic and autoimmune disorders", Expert Opin. Investig. Drugs. 2004, vol. 13. No. 7, pp. 743-762.

Shen et al., "Discovery of Biaryl Anthranil ides as Full Agonists for the High Affinity Niacin Receptor", J. Med. Chem., 2007, vol. 50, pp. 6303-6306.

Mamane et al., "Convenient Access to New Chiral Ferroecno-(iso)quinolines" J. Org. Chem., 2005, vol. 70, pp. 8220-8223.

Nairn, "Solutions, Emulsions, Suspensions and Extractives", Remington's Pharmaceutical Sciences, 1980, 16th edition, chapter 83, pp. 1438-1462.

van Leusen et al., "A Novel and Efficient Synthesis of Oxazoles from Tosylmethylisocyanide and Carbonyl Compounds", Tetrahedron Letters, 1972, No. 23, pp. 2369-2372.

Wright S W et al; "Anilinoquinazoline Inhibitors of Fructose 1, 6-Bisphosphatase Bind at a Novel Allosteric Site: Synthesis, in Vitro Characterization, and X-ray Crystallography"; Journal of Medicinal Chemistry; American Chemical Society, vol. 45 (Jul. 26, 2002), pp. 3865-3877, XP-002379969.

THIAZOLE AND OXAZOLE KINASE INHIBITORS

The present invention is concerned with substituted azole derivatives that selectively modulate, regulate, and/or inhibit signal transduction mediated by certain native and/or mutant protein kinases implicated in a variety of human and animal diseases such as cell proliferative, metabolic, allergic, and degenerative disorders. In particular, several of these compounds are potent and selective Flt-3 inhibitors or/and syk inhibitors.

BACKGROUND OF THE INVENTION

Protein Kinases are receptor type or non-receptor type proteins, which transfer the terminal phosphate of ATP to aminoacid residues, such as tyrosine, threonine, serine residues, of proteins, thereby activating or inactivating signal transduction pathways. These proteins are known to be involved in many cellular mechanisms, which in case of disruption, lead to disorders such as abnormal cell proliferation and migration as well as inflammation.

As of today, there are over 500 known Protein kinases. Included are the well-known Abl, Akt1, Akt2, Akt3, ALK, Alk5, A-Raf, Axl, B-Raf, Brk, Btk, Cdk2, Cdk4, Cdk5, Cdk6, CHK1, c-Raf-1, Csk, EGFR, EphA1, EphA2, EphB2, EphB4, Erk2, Fak, Fes, Fer, FGFR1, FGFR2, FGFR3, FGFR4, Flt-3, Fms, Frk, Fyn, Gsk3a, Gsk3B, HCK, Her2/Erbb2, Her4/Erbb4, IGF1R, IKK beta, Irak4, Itk, Jak1, Jak2, Jak3, Jnk1, Jnk2, Jnk3, KDR, Kit, Lek, Lyn, MAP2K1, MAP2K2, MAP4K4, MAPKAPK2, Met, Mer, MNK1, MLK1, mTOR, p38, PDGFRα, PDGFRβ, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, RON, Src, Stk6, Syk, TEC, Tie2, TrkA, TrkB, Tyk2, VEGFR1/Flt-1, VEGFR2/Kdr, VEGFR3/Flt-4, Yes, and Zap70.

Among tyrosine kinase receptors, Flt-3 is of special interest. Indeed, 60 to 80% of acute myeloid leukemias (AML) blasts express receptor Flt-3, the receptor for Flt-3 ligand and in a high percentage of acute lymphoblastic leukemias (ALL). Both ligand and receptor have been directly or in collaboration identified at U119 (Hannum et al., Nature 368, pp. 643-648, 1994; Rosnet et al., Genomics 9, pp. 380-385, 1991). Flt-3 mediates differentiation and proliferation of normal hematopoietic stem cells and mediates proliferation and survival signals in AML blasts. Although Flt-3 is most commonly expressed in the wild type form, the leukemic clone of 30 to 35% of patients with AML (Nakao et al., Leukemia 12, pp. 1911-1918, 1996), expresses a mutated form of Flt-3 that contains an Internal Tandem Duplication (Flt-3 ITD) of the juxtamembrane domain coding sequence. This mutation leads to constitutive activation of the receptor and autonomous cytokine-independent growth. It has also been reported that a cohort of AML patients (~7%) contains mutations in the activation loop of Flt-3 near the amino acid position Asp835 (Flt-3D835) (Yamamoto et al., Blood 97, pp. 2434-2439, 2001). Flt-3 mutations have also been reported at a frequency of 15% in secondary AML and may be associated with disease progression or relapse of AML.

Patients with Flt-3 mutations tend to have a poor prognosis, with decreased remission times and disease free survival. Specific inhibitors of native and/or mutant Flt-3 kinase present an attractive target for the treatment of hematopoietic disorders and hematological malignancies.

Spleen tyrosine kinase (Syk), an intracellular protein tyrosine kinase, is a key mediator of immunoreceptor signalling in a host of inflammatory cells including B cells, mast cells, macrophages, and neutrophils (Wong Br eta/(2004), Expert Opin Investig Drugs, 13, 743-762). Syk is also widely expressed in nonhematopoietic cells like fibroblasts, breast cancer cells, colonic carcinoma cells, hepatocytes, neuronal cells, and vascular endothelial cells (Okamura S et a/(1999), Oncol Res 11, 281-285). Originally, Syk was thought to function primarily in signaling of immunoreceptors such as Fc receptor (FcR) and B cell receptor (BCR). However, recent studies demonstrated the crucial role of Syk in the cell signaling of diverse cellular stimuli including IL-1, tumor necrosis factor-α (TNFα), lipopolysaccharide, and 81-integrin (Yamada T et al (2001), J Immunol, 167, 283-288). For instance, Syk can be activated by TNFα, resulting in MAPK phosphorylation and NF-κB translocation in hematopoietic cell lines (Takada Y and Aggarwal B B (2004), J Immunol, 173, 1066-1077). IL-1-induced chemokine production in fibroblasts of nasal polyps is also mediated by Syk activation (Yamada T et a/(2001), J Immunol, 167, 283-288). Syk has emerged as a potential therapeutic target for treatment of allergic and autoimmune disorders.

GOAL OF THE INVENTION

The main objective underlying the present invention is therefore to find potent and selective compounds capable of inhibiting wild type and/or mutated protein kinase, in particular wild type and/or mutated tyrosine kinase, and more particularly wild type and/or mutated Flt-3 and/or syk.

Many different compounds have been described as Flt-3 tyrosine kinase inhibitors, for example, AG1295 and AG1296; Lestaurtinib (Cephalon); CEP-5214 and CEP-7055 (Cephalon); CHIR-258 (Chiron Corp.); EB-IO and IMC-EBIO (ImClone Systems Inc.); GTP-14564 (Merk Biosciences UK). Midostaurin (Novartis AG); MLN 608 (Millennium USA); MLN-518 and MLN-608 (Millennium Pharmaceuticals Inc.); SU-11248 (PfizerUSA); SU-11657 (Pfizer USA); SU-5416 and SU-5614; THRX-165724 (Theravance Inc.); AMI-10706 (Theravance Inc.); VX-528 and VX-680 (Novartis Switzerland), Merck & Co USA); and XL-999 (Exelixis USA); AC220 (Ambit Biosciences Corp. USA). The following PCT International Applications and US Patent Applications disclose additional kinase modulators, including modulators of Flt-3: WO 2002032861, WO 2002092599, WO 2003035009, WO 2003024931, WO 2003037347, WO 2003057690, WO 2003099771, WO 2003024969, WO 2004005281, WO 2004016597, WO 2004018419, WO 2004039782, WO 2004043389, WO 2004046120, WO 2004058749, WO 2004058749, WO 2008016665.

The compound R406 (Rigel Pharmaceuticals) was reported to inhibit Syk (Braselmann, Taylor et al. J Pharmacol Exp Ther, (2006), 319(3), 998-1008). Interestingly and After Syk, Flt-3 autophosphorylation was most potently inhibited by R406 at approximately 5-fold less potency than Syk activity (Braselmann, Taylor et al. 2006). Although exact mechanism of action of Rigel inhibitor R406 is unclear, the data suggest that inhibition of kinases that mediate survival signaling in lymphocytes is clinically beneficial.

In particular, the invention aims to provide a method and compounds for selectively modulating, regulating, and/or inhibiting signal transduction mediated by certain native and/or mutant protein kinase, and in particular tyrosine kinases implicated in a variety of human and animal diseases such as cell proliferative, metabolic, allergic, and degenerative disorders. More particularly, these compounds are potent and selective Flt-3 and/or Syk inhibitors.

The invention aims notably to provide a method for treating AML or ALL.

DESCRIPTION OF THE INVENTION

Compounds of the present invention were screened for their ability to inhibit a protein kinase and in particular a tyrosine kinase, and more particularly Flt-3 and/or Flt-3 mutant (especially Flt-3 ITD), and/or Syk.

In connection with the present invention, the inventors have discovered that compounds displaying specific substitutions in oxazole and thiazole derivatives are potent and selective inhibitors of native and/or mutant Flt-3. These compounds are good candidates for treating cell proliferative disorder and/or disorders related to Flt-3. Such disorders are abnormal cell proliferation and migration as well as inflammation where Flt-3 expression should be inhibited or where it is needed to selectively modulate, regulate, and/or inhibit signal transduction mediated by certain native and/or mutant Flt-3. In particular, the invention relates to a method and compounds for the treatment of hematopoietic disorders and hematological malignancies. Such disorders include acute myeloid leukemia, and acute lymphoid leukemias.

In connection with the present invention, the inventors have discovered that compounds displaying specific substitutions in oxazole and thiazole derivatives are potent and selective inhibitors of syk.

DETAILED DESCRIPTION OF THE INVENTION

Therefore, the present invention relates to compounds belonging to the substituted azole derivatives. These compounds are capable of selectively inhibiting signal transduction involving a protein kinase, and in particular a tyrosine kinase, and more particularly the tyrosine phosphokinase Flt-3 and mutant forms thereof and/or syk.

In the foregoing description any reference to protein kinase, and in particular a tyrosine kinase implicitly refers to Flt-3 and/or syk. In a first embodiment, the invention is aimed at compounds of formula I, which may represent either free base forms of the substances or pharmaceutically acceptable salts thereof:

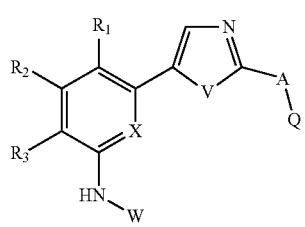

FORMULA I wherein substituents A, Q, X, R1, R2, R3, V and W in Formula I are defined as follows:

A is one of the following:
i) N(R4) (CH2)$_n$ where n is 0<n<3
ii) O(CH2)$_n$ where n is 0<n<3
iii) S(CH2)$_n$ where n is 0<n<3
iv) (CH2)$_n$ where n is 0≤n<4
v) C(O)(CH2)$_n$ where n is 0<n<3
vi) C(R4)=C(R5)
vii) CC(R5)

R4 and R5 each independently are hydrogen, $C_{1-4}$alkyl, $C_{2-6}$alkenyl, $C_{2-6}$alkynyl, $C_{3-7}$cycloalkyl, $C_{1-4}$haloalkyl, $C_{1-4}$alkoxy, $C_{1-4}$hydroxyalkyl, $C_{1-4}$alkylamino;

X is CH or N;
V is O or S;
Q is selected from:
i) an alkyl[1] group, or
ii) an aryl[1] group, or
iii) an heteroaryl[1] group;

an alkyl[1] group is defined as a linear, branched or cycloalkyl group containing from 1 to 10 carbon atoms and optionally substituted with one or more hetereoatoms such as halogen (selected from F, Cl, Br or I), oxygen, and nitrogen; as well as trifluoromethyl, carboxyl, cyano, nitro, formyl; as well as CO—R, COO—R, CONR—R', SO2-R, and SO2NR—R' wherein R and R' are a linear or branched alkyl group containing 1 to 10 carbon atoms and optionally substituted with at least one heteroatom, notably a halogen (selected from F, Cl, Br or I), oxygen, and nitrogen; as well as a cycloalkyl or aryl[1] or heteroaryl[1] group;

an aryl[1] group is defined as phenyl or a substituted variant thereof bearing any combination, at any one ring position, of one or more substituents such as
- halogen (selected from I, F, Cl or Br),
- an alkyl[1] group,
- a cycloalkyl, aryl or heteroaryl group,
- trifluoromethyl, O-alkyl, carboxyl, cyano, nitro, formyl, hydroxy, NH-alkyl, N(alkyl)(alkyl), and amino group,
- NRCO—R' or NRCOO—R' or NRCONR'—R" or NRSO2-R' or NRSO2NR'—R" or CO—R or COO—R or CONR—R' or SO2-R or or SO2NRR' wherein R, R' and R" each independently are selected from hydrogen, alkyl, aryl or heteroaryl group;

a heteroaryl[1] group is defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, benzoxazole, benzothiazole, quinolinyl group, etc., which may additionally bear any combination, at any one ring position, of one or more substituents such as
- halogen (selected from F, Cl, Br or I),
- an alkyl[1] group,
- a cycloalkyl, aryl or heteroaryl group,
- trifluoromethyl, O-alkyl, carboxyl, cyano, nitro, formyl, hydroxy, NH-alkyl, N(alkyl)(alkyl), and amino group,
- NRCO—R' or NRCOO—R' or NRCONR'—R" or NRSO2-R' or NRSO2NR'—R" or CO—R or COO—R or CONR—R' or SO2-R or or SO2NRR' wherein R, R' and R" each independently are selected from hydrogen, alkyl, aryl or heteroaryl group;

R1, R2 and R3 each independently are selected from hydrogen, halogen (selected from F, Cl, Br or I), a linear or branched alkyl group containing from 1 to 10 carbon atoms and optionally substituted with one or more hetereoatoms such as halogen (selected from F, Cl, Br or I), oxygen, and nitrogen; as well as trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONR—R', SO2-R, and SO2NR—R' wherein R and R' each independently are selected from hydrogen, alkyl, aryl or heteroaryl group;

W is aryl[1] or heteroaryl[1]. Aryl[1] and heteroaryl[1] are defined like described above.

Unless stated otherwise (for example by the indication alkyl[1], aryl[1] or heteroaryl[1]), for the purpose of the present invention, the term "alkyl group" means any linear or branched, substituted or unsubstituted, C1-C10 alkyl group, such as C1-C4 or C1-C6, in particular a methyl, ethyl group, propyl group, preferably methyl. The term "cycloalkyl group" means a saturated or partially unsaturated, monocyclic, fused bicyclic or bridged polycyclic ring assembly containing the number of ring atoms indicated. This includes substituted or unsubstituted cylcoalkyl groups. For example, cycloalkyl group may be C3-C10 alkyl group, such as C5 or C6, in particular a cyclopropyl, cyclobutyl, cyclopentyl, cyclohexyl, cycloheptyl or cyclooctyl group etc. Cycloalkyl groups include heterocycle, by replacing one or more carbon atoms of the cycloalkyl group by one or more nitrogen, oxygen, or sulphur atoms. It includes cycloheteroalkyl water-solubilizing groups as described herein after. The term "alkoxy group" as used herein, alone or in combination, includes an alkyl group connected to the oxygen connecting atom. Examples of suitable alkoxy groups include methoxy, ethoxy, n-propoxy, i-propoxy, n-butoxy, s-butoxy, t-butoxy. The term "aryl group" means a substituted or unsubstituted monocyclic or fused bicyclic aromatic ring assembly containing six to ten ring carbon atoms. For example, aryl may be phenyl or naphthyl, preferably phenyl. The term "heteroaryl group" is as defined for aryl group above where one or more of the ring members is a heteroatom. For example heteroaryl groups includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

In some embodiments, the Q and W moieties each independently, are a substituted aryl group or heteroaryl group, in which at least one of the substituents is a water-solubilizing group. As used herein, a "water-solubilizing" group is a group that has hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups (e.g., O, S, N, NH, N—$(CH_2)_z$R, N—$(CH_2)_z$—C(O)R, N—$(CH_2)_z$—C(O)OR, N—$(CH_2)_z$—S(O)$_2$R, N—$(CH_2)_z$—S(O)$_2$OR, N—$(CH_2)_z$—C(O)NRR, etc., where z is an integer ranging from 0 to 6, R and R' each independently are selected from hydrogen, a linear or branched alkyl group containing from 1 to 10 carbon atoms and optionally substituted with one or more hetereoatoms such as halogen (selected from F, Cl, Br or I), oxygen, and nitrogen; as well as $C_{1-6}$alkyloxy, $C_{1-6}$alkylamino, $C_{1-6}$alkylhydroxy, di($C_{1-6}$alkyl)amino; as well as aryl and heteroaryl group.

In some embodiments, the water-solubilizing group is a cycloheteroalkyl that optionally includes from 1 to 5 substituents, which may themselves be water-solubilizing groups.

In a specific embodiment, the water-solubilizing group is of the formula,

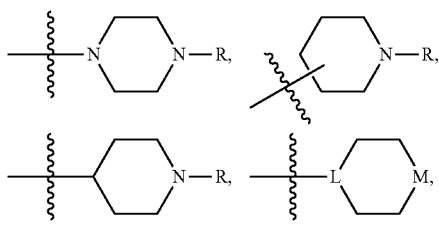

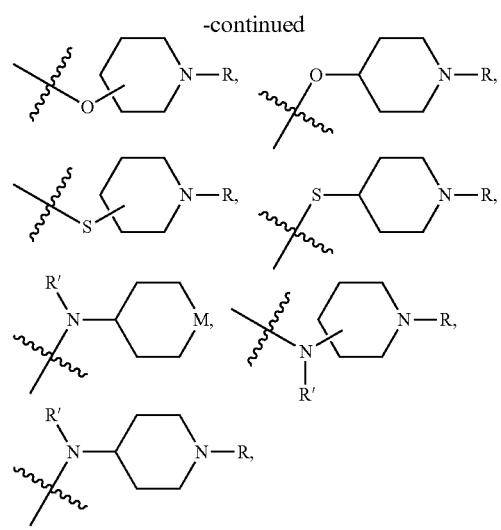

where L is selected from the group consisting of CH and N, M is selected from the group consisting of CH(R)—, —CH$_2$—, —O—, —S—, —NH—, —N(—$(CH_2)_z$—R)—, —N(—$(CH_2)_z$—C(O)R)—, —N(—$(CH_2)_z$—C(O)OR)—, —N(($CH_2)_z$)—S(O)$_2$R)—, —N(—$(CH_2)_z$—S(O)$_2$OR)— and —N(—$(CH_2)_z$—C(O)NRR')—, where z is an integer ranging from 0 to 6, R and R' each independently are selected from hydrogen, a linear or branched alkyl group containing from 1 to 10 carbon atoms and optionally substituted with one or more hetereoatoms such as halogen (selected from F, Cl, Br or I), oxygen, and nitrogen; as well as $C_{1-6}$alkyloxy, $C_{1-6}$alkylamino, $C_{1-6}$alkylhydroxy, di($C_{1-6}$alkyl)amino; as well as aryl and heteroaryl group, with the proviso that L and M are not both simultaneously CH and CH$_2$, respectively.

In another specific embodiment, the water-solubilizing group is selected from the group consisting of morpholino, piperidinyl, ($C_1$-$C_6$) N-alkyl piperidinyl, N-methyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, ($C_1$-$C_6$) N-alkylpiperazinyl, N-methylpiperazinyl, N-ethyl piperidinyl, N-ethyl piperazinyl, N-cycloalkyl piperazinyl, N-cyclohexyl piperazinyl, pyrrolidinyl, N-alkyl pyrrolidinyl, N-methylpyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl, imidazolyl, and the like.

The terms "one or more" encompass any combinations of the species to which they refer.

Preferred compounds of the invention are those of formula Ia:

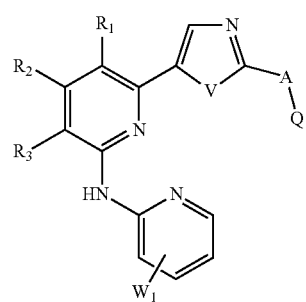

Formula Ia

Wherein, A, Q, R1, R2, R3, and V are as defined above, and W1 is selected from one or more of the following: hydrogen, halogen (selected from F, Cl, Br or I), a linear or branched alkyl group containing from 1 to 10 carbon atoms and optionally substituted with one or more hetereoatoms such as halogen (selected from F, Cl, Br or I), oxygen, and nitrogen; as well as trifluoromethyl, $C_{1-6}$alkyloxy, amino, $C_{1-6}$alkylamino, di($C_{1-6}$alkyl)amino, carboxyl, cyano, nitro, formyl, hydroxy, CO—R, COO—R, CONR—R', SO2-R, and SO2NR—R' wherein R and R' each independently are selected from hydrogen, alkyl, aryl or heteroaryl group.

In a particular embodiment V is O. In another particular embodiment V is S.

In one embodiment all of R1, R2, R3 are hydrogen atoms.

In formula I and Ia, A is preferably selected from CH2-CH2, S, S—CH2, NH—CH2, CH=CH, CC or is absent.

According to one embodiment of formula I and Ia, Q is aryl or heteroaryl group optionally substituted by halogen (selected from F, Cl, Br or I), cyano, trifluoromethyl, amino, alkoxy groups as defined above, alkyl groups as defined above or a nitro group.

According to one embodiment of formula I and Ia, Q is cycloalkyl, such as as defined above, and preferably selected from cyclohexyl, cyclopentyl, cycloheptyl, and cyclooctyl.

In one embodiment W1 is hydrogen, methyl, ethyl, propyl, isopropyl, butyl, isobutyl, sec-butyl, terbutyl, methoxy, ethoxy or propyloxy optionally bearing one or more substituents, such as nitrogen, oxygen or halogen (selected from F, Cl, Br or I), for example as trifluoromethyl or trifluoromethoxy, hydroxy, alkylamine and hydroxyalkyl.

Among the particular compounds of formula I, the invention is directed to compounds of the following formula:

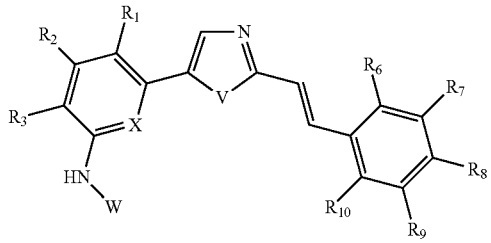

FORMULA II

Wherein R1, R2, R3, X, V and W have the meaning described above, and

Wherein R6, R7, R8, R9 and R10 each independently are selected from hydrogen, halogen (selected from F, Cl, Br or I), a linear or branched alkyl group containing from 1 to 10 carbon atoms and optionally substituted with one or more hetereoatoms such as halogen (selected from F, Cl, Br or I), oxygen, and nitrogen; as well as trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONR—R', SO2-R, and SO2NR—R' wherein R and R' each independently are selected from hydrogen, alkyl, aryl or heteroaryl group.

According to the invention, compounds of formula II may be those of Formula Ia defined above including each embodiment, wherein A-Q is as follows:

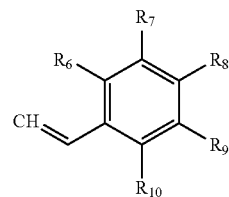

Such compounds may be represented by formula IIa below:

Formula IIa

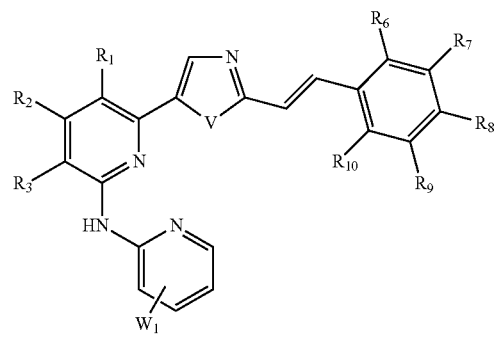

Wherein, R1, R2, R3, R6, R7, R8, R9 and R10, V and W1 have the meaning described above.

Among the particular compounds of formula I, the invention is directed to compounds of the following formula:

FORMULA III

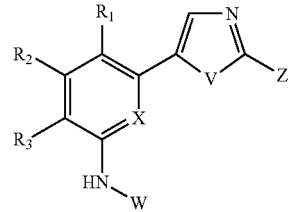

Wherein Z is Aryl[1] or heteroaryl[1]. R1, R2, R3, X, V, W, Aryl[1] and heteroaryl[1] have the meaning described above.

According to the invention, compounds of formula III may be those of Formula Ia defined above including each embodiment, wherein A-Q is Z as defined above.

Such compounds may be represented by formula IIIa below:

Formula IIIa

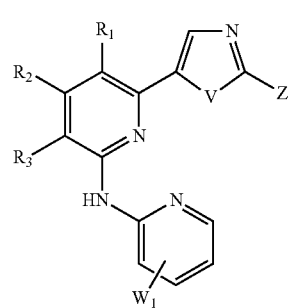

Wherein, R1, R2, R3, V, W1 and Z have the meaning described above.

The compounds of the present invention may be prepared using the general protocol as follows:

Aromatic aldehydes of general formula (2) were reacted with p-toluenesulfonylmethyl isocyanide (TosMIC) to prepare the corresponding 5-arylsubstitued oxazoles (3) using the method of Van Leusen et. al. (*Tetrahedron Lett.,* 1972, 23, 2369). The non-commercial aldehydes were prepared using literature methods to introduce the aldehyde group from the corresponding brominated aromatic compound (I) using an organometallic reagent and DMF (*Org. Lett.,* 2004, 6, 1887).

Those compounds of general formula (3) carrying a substitutable atom, eg Br, were then further functionalised where necessary using known palladium-catalysed N-arylation protocols with a suitable combination of ligand and inorganic base for each substrate to afford the N-linked analogues (4). Deprotonation of the oxazole moiety by a suitable organic base and subsequent electrophilic chlorination or iodination was used to prepare the 2-chlorooxazole or 2-iodooxazole coumpounds (5). This allowed access to various families of molecules by substitution of the chlorine by either amine or thiol nucleophiles to generate compounds of the general formula (6). Similarly, the chlorinated or iodinated oxazoles (5) were used to prepare further C-2 substituted analogues (7) using classical palladium catalysed coupling reactions (Diederich, F. and Stang P. J. "Metal-catalyzed Cross-coupling Reactions" WILEY-VCH, 1998), eg. Stille or Suzuki coupling in the presence of stannanes or arylboronic acids respectively (Scheme 1). Compounds (4) were used to prepare further analogues (14) by Nickel catalysed alkynylation, using the method of Matsuyama et. al. (*Org. Lett,* 2009, 11, 4156).

Scheme 1

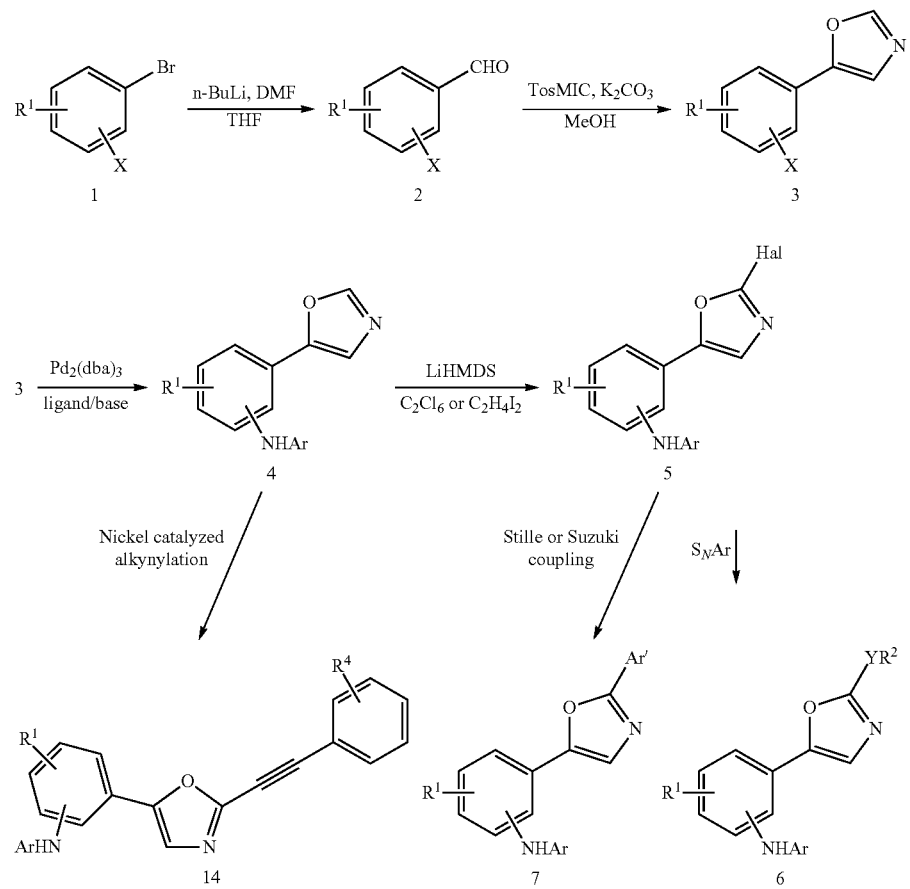

Furthermore, the unsubstituted oxazoles (4) were also used in palladium-catalysed C—H activation reactions (Scheme 2), in order to install an aromatic ring in the C-2 position regioselectively according to the method of Besselievre et al. (Synthesis 2009, 20, 3511; *Org. Lett,* 2008, 10 (18), 4029). Additionally, these oxazole intermediates (4) were reacted with a number of 3-bromostyrenes to prepare the corresponding 2-styryloxazoles (8) by a similar method. The non-commercial bromostyrenes used herein were prepared from the corresponding cinnamic acids using the published Hunsdieker protocol or from the corresponding aldehydes by Corey-Fuchs dibromination followed by debromination by the Hirau reduction with triphenylphosphine. Alternatively, oxazoles (8) could be prepared from halogenated analogues (5) by Palladium catalysed cross-coupling with a suitable boronic acid or ester. A further family of inhibitors (9) was prepared by reduction of the double bond of the styryloxazoles (8) by atmospheric pressure catalytic hydrogenation, as described in Hudlicky "Reductions in Organic Chemistry" John Wiley and Sons, 1984.

Scheme 2

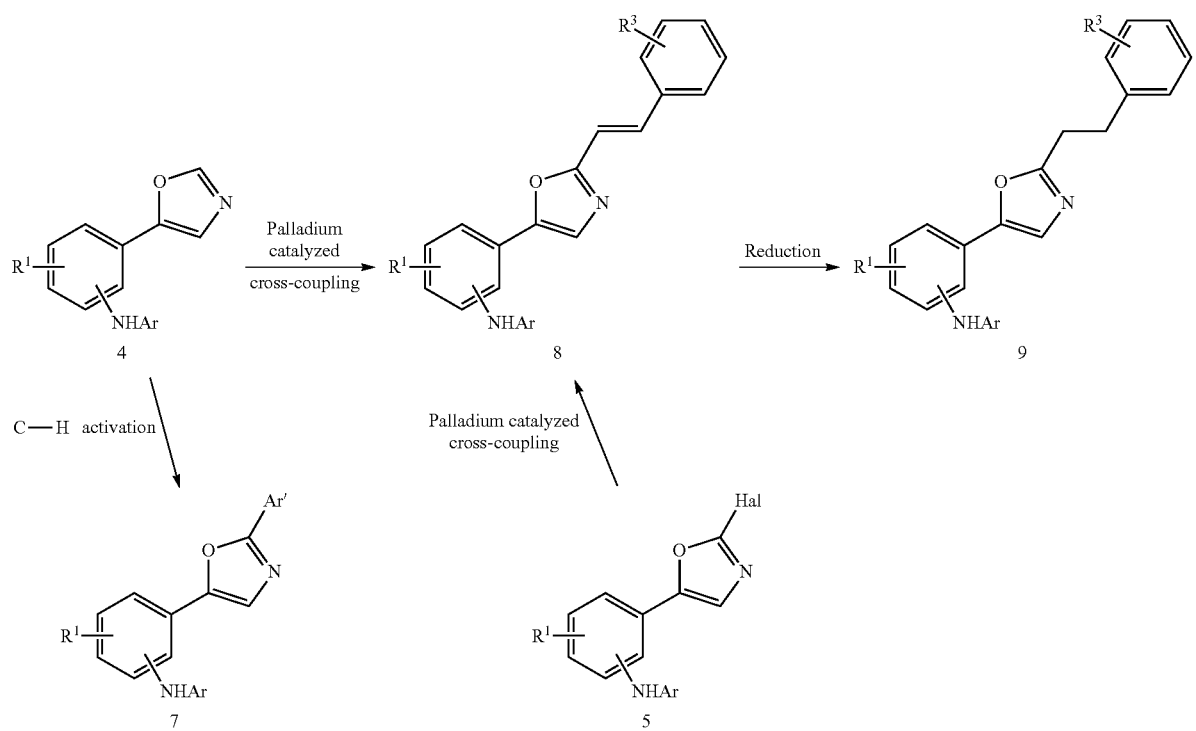

Thiazoles of general formula (13) were prepared as follows: commercial 2-bromothiazole was reacted with aromatic boronic acids or organozinc reagents using known Suzuki protocols (*J. Med. Chem.*, 2005, 48, 224) or Negishi protocols protocols (*Tet. Lett.* 2010, 51, 357-359) respectively in order to obtain thiazoles (10). Deprotonation of the thiazole moiety by a suitable organic base followed by electrophilic stannylation was used to prepare compounds (II). Subsequent Stille coupling reactions using 2,6-dibromopyridine allowed access to bromo-pyridines of formula (12). Classical palladium-catalysed N-arylation protocols afford the N-linked analogues (13). Analogues (13) can also be obtained directly from compounds (II) by Stille coupling (Scheme 3).

Scheme 3

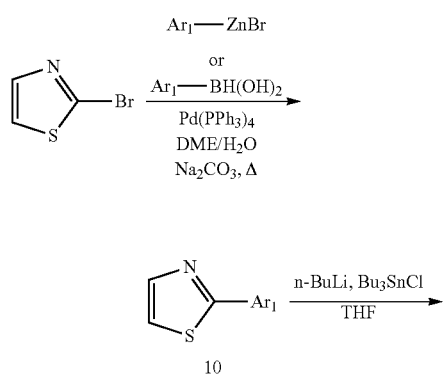

-continued

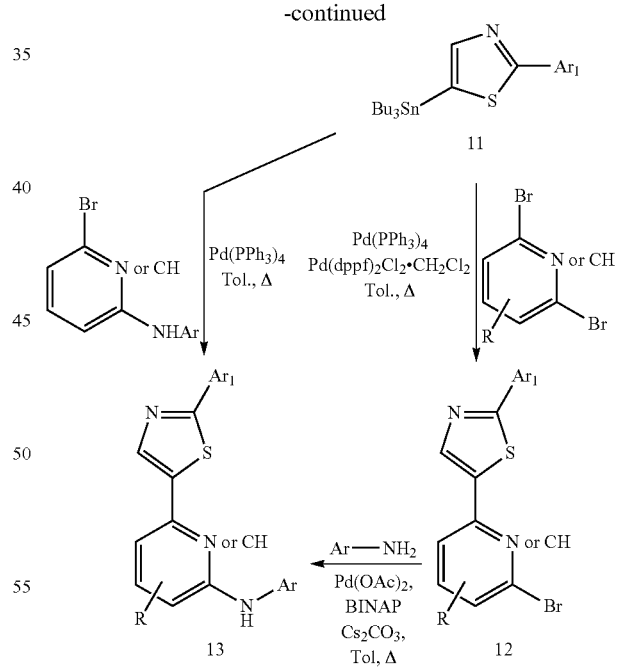

Furthermore, 2-styrylthiazoles (18) were synthesised from 2-[1,3]dioxolan-2-yl-5-tributylstannanyl-thiazole XIV (*J. Med. Chem.* 2007, 50, 6303) (Scheme 4). Derivatives of formula (16) were obtained in a similar manner to the two-step palladium-catalysed sequence described for the preparation of compounds (13). Dioxolanes (16) were then deprotected in acidic conditions, followed by classical Wittig reaction of the corresponding aldehydes (17) using benzyltriphenylphosphonium salts and a suitable base to afford families of E-styrylthiazoles (18) after separation of the isomers by classical chromatographic methods.

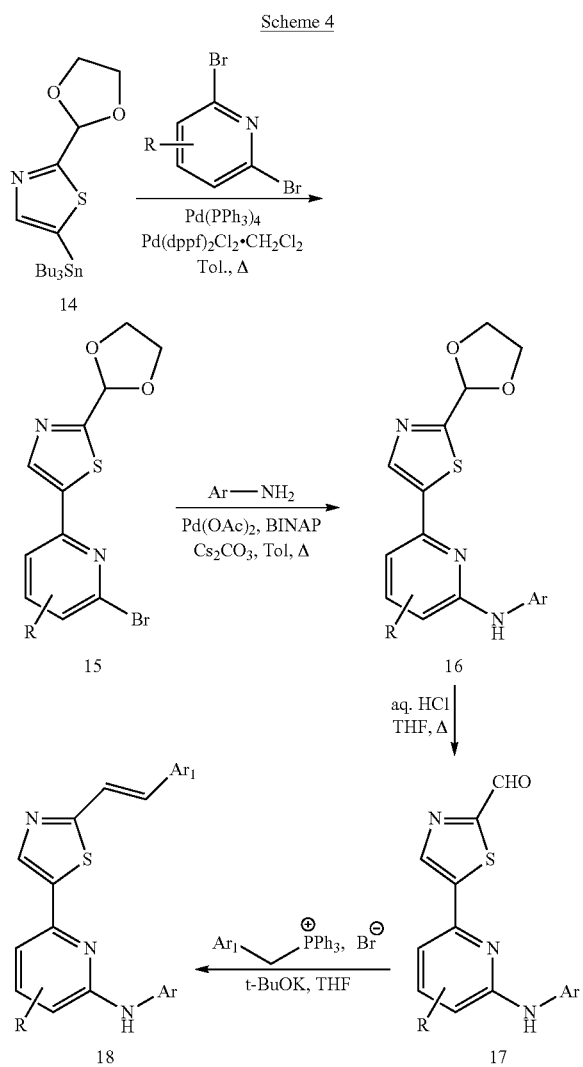

Scheme 4

In the synthesis of compounds of formula I, $R^1$ and R represents schematically one or more group selected from $R_1$, $R_2$ and $R_3$; X is halogen; $R^3$ represents one or more groups selected from $R_6$, $R_7$, $R_8$, $R_9$ and $R_{10}$. $YR^2$ represents an amine group or a thiol group. Ar and $Ar_1$ represent aryl or heteroaryl groups. Hal represent a halogen atom.

The invention further relates to a compound selected from:
(4-methyl-pyridin-2-yl)-(6-oxazol-5-yl-pyridin-2-yl)-amine
[6-(2-Chloro-oxazol-5-yl)-pyridin-2-yl]-(4-methyl-pyridin-2-yl)-amine
[6-(2-iodo-oxazol-5-yl)-pyridin-2-yl]-(4-methyl-pyridin-2-yl)-amine
2-Bromo-6-(2-pyridin-3-yl-thiazol-5-yl)-pyridine
2-Bromo-6-(2-[1,3]dioxolan-2-yl-thiazol-5-yl)-pyridine
[6-(2-[1,3]Dioxolan-2-yl-thiazol-5-yl)-pyridin-2-yl]-(4-methyl-pyridin-2-yl)-amine
5-[6-(4-Methyl-pyridin-2-ylamino)-pyridin-2-yl]-thiazole-2-carbaldehyde.

These compounds are good intermediates for the synthesis of the active compounds of the invention.

In a second embodiment, the invention relates to a pharmaceutical composition comprising a compound as depicted above.

Accordingly the invention relates to pharmaceutical composition comprising at least one compound of the invention and an acceptable pharmaceutical excipient.

As is known to the person skilled in the art, various forms of excipients can be used adapted to the mode of administration and some of them can promote the effectiveness of the active molecule, e.g. by promoting a release profile rendering this active molecule overall more effective for the treatment desired.

The pharmaceutical compositions of the invention are thus able to be administered in various forms, more specially for example in an injectable, pulverizable or ingestible form, for example via the intramuscular, intravenous, subcutaneous, intradermal, oral, topical, rectal, vaginal, ophthalmic, nasal, transdermal or parenteral route. The present invention notably covers the use of a compound according to the present invention for the manufacture of a composition, particularly a pharmaceutical composition.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V. 60, pp. 263-69, 1973), lauryl amine oxide (Johnson et. al., U.S. Pat. No. 4,411,893), azone (Rajadhyaksha, U.S. Pat. No. 4,405,616 and U.S. Pat. No. 3,989,816) and decylmethyl sulfoxide (Sekura, D. L. and Scala, J., "The Percutaneous Absorption of Alkylmethyl Sulfides," Pharmacology of the Skin, Advances In Biolocy of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physicochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et al., U.S. Pat. No. 4,615,699 and Campbell et al., U.S. Pat. Nos. 4,460,372 and 4,379,454), dimethyl sulfoxide (U.S. Pat. No. 3,740,420 and U.S. Pat. No. 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:

- liquid gas systems (a liquefied gas is used as propellent gas (e.g. low-boiling FCHC or propane, butane) in a pressure container,
- suspension aerosol (the active substance particles are suspended in solid form in the liquid propellent phase),
- pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. In other words, the invention embraces a method for treating a disease related to deregulated Flt-3 and/or syk comprising administering an effective amount of at least one compound as defined above to a mammal in need of such treatment.

A disease related to deregulated Flt-3 and/or syk is a disease which is prevented, treated or which regresses by modulation, regulation, and/or inhibition of Flt-3 and/or syk.

Advantageously, the compounds according to the invention can be used in an efficient amount. These quantities are generally comprised between 0.1 mg and 2 g of the compound of the invention per day per kilogram of body weight.

The invention relates to another aspect to a method or compound for modulating, regulating, and/or inhibiting, in cells, signal transduction mediated by a native and/or mutant protein kinase, and in particular a native and/or mutant tyrosine kinase, and more particularly native and/or mutant Flt-3 and/or syk. Said method comprises administering to cells at least one compound of the invention. In one embodiment said cells are AML blasts or hematopoietic stem cells with a protein kinase mutation, and in particular a tyrosine kinase mutation, and more particularly Flt-3 mutation.

The terms "compound of the invention" means an azole derivative as described above, including each embodiment, taken alone or in combinations. Any combination of the different variants, aspects and embodiments are within the scope of the invention.

The invention also relates to a method or compound for treating a human and animal diseases related to a disorder of the signal transduction mediated by native and/or mutant protein kinase, and in particular a native and/or mutant tyrosine kinase, and more particularly native and/or mutant Flt-3 and/or syk. In particular such a method is for treating a proliferative, metabolic, allergic, and/or degenerative disorder.

Said method comprises administering to a subject, and in particular to a human patient, in need thereof an effective amount of at least one compound of the invention.

In one embodiment, said subject or patient has been diagnosed as having an AML or ALL.

The invention relates to a method or compound for treating AML or ALL, said method comprising administering an effective amount of at least one compound of the invention to a subject, and in particular to a human patient, having an AML or ALL.

The invention relates to a method or compound for the treatment of hematopoietic disorders and hematological malignancies.

More particularly, the invention is aimed at a method for treating a disease selected from autoimmune diseases, allergic diseases, bone loss, cancers such as leukemia and GIST, tumor angiogenesis, viral infection, inflammatory diseases, inflammatory bowel diseases (IBD), interstitial cystitis, mastocytosis, infections diseases, metabolic disorders, fibrosis, diabetes and CNS disorders comprising administering an effective amount a compound depicted above to a mammal in need of such treatment.

The above described compounds are useful for manufacturing a medicament for the treatment of diseases related to deregulated Flt-3 and/or syk, including, but not limited to:

neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas.

tumor angiogenesis.

metabolic diseases such as diabetes mellitus and its chronic complications;

obesity; diabete type II; hyperlipidemias and dyslipidemias; atherosclerosis; hypertension; and cardiovascular disease.

allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.

interstitial cystitis.

bone loss (osteoporosis).

inflammatory diseases such as rheumatoid arthritis, conjunctivitis, rheumatoid spondylitis, osteoarthritis, gouty arthritis and other arthritic conditions.

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.

graft-versus-host disease or graft rejection in any organ transplantation including kidney, pancreas, liver, heart, lung, and bone marrow.

Other autoimmune diseases embraced by the invention active chronic hepatitis and chronic fatigue syndrome.

subepidermal blistering disorders such as pemphigus.

Vasculitis.

Viral infection.

Bacterial infection.

melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.

CNS disorders such as psychiatric disorders, migraine, pain, memory loss and nerve cells degeneracy. More particularly, the method according to the invention is useful for the treatment of the following disorders:
Depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (MND), and Amyotrophic Lateral Sclerosis (ALS).

substance use disorders as referred herein include but are not limited to drug addiction, drug abuse, drug habituation, drug dependence, withdrawal syndrome and overdose.

Cerebral ischemia

Fibrosis

Duchenne muscular dystrophy

The invention thus relates to the use of one or more compounds of the invention to manufacture a medicament for treating hematological malignancies, myeloproliferative disorder, other proliferative disorders, autoimmune disorders, inflammatory diseases, allergic diseases, and/or neurological diseases.

In an embodiment, hematological malignancies is acute myeloid leukemias (AML), myelodysplastic syndromes (MDS), acute lymphoblastic leukemia (ALL), and/or chronic myeloid leukemia (CML).

In an embodiment, proliferative disorder is cancer.

In an embodiment, autoimmune disorders is multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, atopic dermatitis and/or proliferative glomerulonephritis.

In an embodiment, allergic diseases is asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and/or blood sucking parasitic infestation.

In an embodiment, a neurologic disease is Huntington's disease, schizophrenia, Parkinson's disease and/or Alzheimer's disease.

In an embodiment, the compound(s) of the invention is/are used for the manufacture of a medicament that act as an inhibitor of protein kinases.

In particular, the protein kinase is Flt-3 or syk.

The invention further relates a method for treating or preventing a protein kinase, and in particular a tyrosine kinase, and more particularly Flt-3 and/or syk related disease or disorder in a subject comprising administration to the subject an effective amount of at least one compound of the invention.

The invention relates to a pharmaceutical composition comprising an effective amount of a combination of at least one compound of the invention and another molecularly targeted agent.

The invention relates to a method for preventing or treating haematological malignancies, myeloproliferative disorder, other proliferative disorders, autoimmune disorders and skin disorders, comprising simultaneously or sequentially administering to a human or animal subject in need thereof at least one compound of the invention in combination with another molecularly targeted agent, in sufficient amounts to provide a therapeutic effect.

The invention relates to the use of at least one compound of the invention together with another molecularly targeted agent, for the manufacture of a medicament for the treatment of haematological malignancies, myeloproliferative disorder, other proliferative disorders, autoimmune disorders and skin disorders.

The invention relates also to the use of at least one compound of the invention for the selective inhibition of Syk. The invention relates also to the use of at least one compound of the invention for the treatment of autoimmune and/or inflammatory and/or allergic diseases.

The invention is now illustrated by Examples which represent currently preferred embodiments which make up a part of the invention but which in no way are to be used to limit the scope of it.

Examples 1 and 2 of Preferred Compounds of the Formula I are Depicted Below

Example 001

(4-Methyl-pyridin-2-yl)-[6-(2-phenethyl-oxazol-5-yl)-pyridin-2-yl]-amine

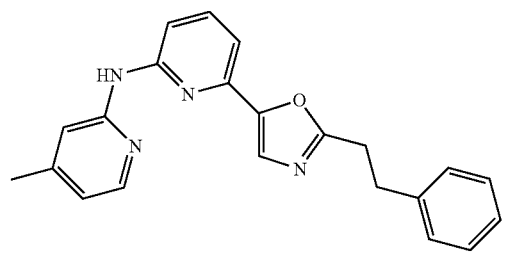 [SMILES: Cc1ccnc(Nc2cccc(-c3cnc(CCc4ccccc4)o3)n2)c1]

$^1$H NMR (DMSO-$d_6$, 300 MHz) δ=9.88 (s, 1H), 8.12 (d, J=5.0 Hz, 1H), 7.90-7.41 (m, 4H), 7.43-6.96 (m, 6H), 6.78 (d, J=4.8 Hz, 1H), 3.26-2.92 (m, 4H), 2.33 (s, 3H). (ESI+) m/z 357 (M+H)$^+$.

Example 002

(4-Methyl-pyridin-2-yl)-[3-(2-phenylsulfanyl-oxazol-5-yl)-phenyl]-amine

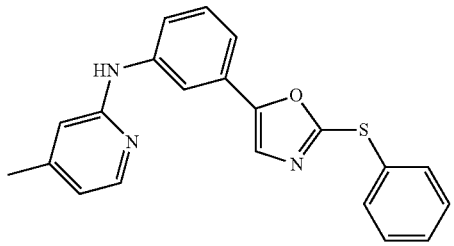 [SMILES: Cc1ccnc(Nc2cccc(-c3cnc(Sc4ccccc4)o3)c2)c1]

$^1$H NMR (DMSO-d$_6$, 300 MHz) δ=9.09 (s, 1H), 8.02 (d, J=5.0 Hz, 1H), 7.93 (s, 1H), 7.80-7.25 (m, 8H), 8.02 (d, J=7.4 Hz, 1H), 6.64 (br, 2H), 2.24 (s, 3H). (ESI+) m/z 360 (M+H)$^+$. Retention time=3.28 mins (method 1).

Examples 3 to 7 of Preferred Compounds of the Formula II are Depicted Below

Example 003

(3-{2-[2-(4-Methoxy-phenyl)-vinyl]-oxazol-5-yl}-phenyl)-(4-methyl-pyridin-2-yl)-amine

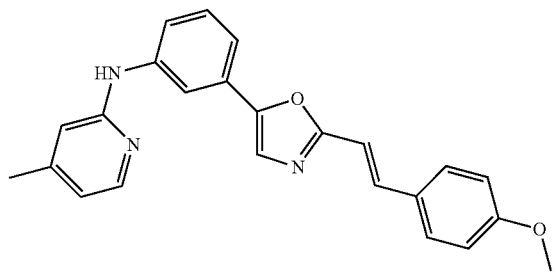

$^1$H NMR (DMSO-d$_6$, 300 MHz) δ=9.12 (s, 1H), 8.07 (d, J=5.0 Hz, 1H), 8.04 (s, 1H), 7.80-7.60 (m, 4H), 7.53 (d, J=16.8 Hz, 1H), 7.40-7.20 (m, 2H), 7.05 (d, J=16.8 Hz, 1H), 7.00 (d, J=8.1 Hz, 1H), 6.68 (s, 1H), 6.62 (d, J=4.9 Hz, 1H), 3.81 (s, 3H), 2.25 (s, 3H). (ESI+) m/z 384 (M+H)$^+$. Retention time=3.34 mins (method 1).

Example 004

(6-{2-[2-(4-Methoxy-phenyl)-vinyl]-oxazol-5-yl}-pyridin-2-yl)-(4-methyl-pyridin-2-yl)-amine

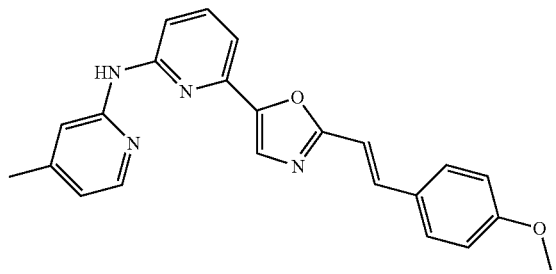

$^1$H NMR (DMSO-d$_6$, 300 MHz) δ=9.77 (s, 1H), 8.11 (d, J=4.8 Hz, 1H), 7.92-7.52 (m, 7H), 7.33 (d, J=7.2 Hz, 1H), 7.17-6.93 (m, 3H), 6.78 (d, J=4.7 Hz, 1H), 3.81 (s, 3H), 2.35 (s, 3H). (ESI+) m/z 385 (M+H)$^+$.

Example 005

(4-Methyl-pyridin-2-yl)-[6-(2-styryl-oxazol-5-yl)-pyridin-2-yl]-amine

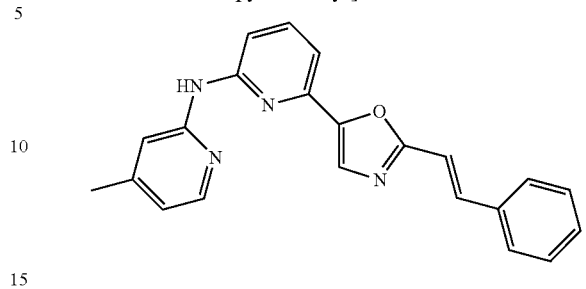

$^1$H NMR (DMSO-d$_6$, 300 MHz) δ=9.78 (s, 1H), 8.12 (d, J=5.0 Hz, 1H), 7.86 (s, 1H), 7.84-7.72 (m, 4H), 7.72-7.56 (m, 2H), 7.50-7.33 (m, 4H), 7.25 (d, J=16.5 Hz, 1H), 6.78 (d, J=4.9 Hz, 1H), 2.35 (s, 3H). (ESI+) m/z 355 (M+H)$^+$.

Example 006

Pyridin-2-yl-[6-(2-styryl-oxazol-5-yl)-pyridin-2-yl]-amine

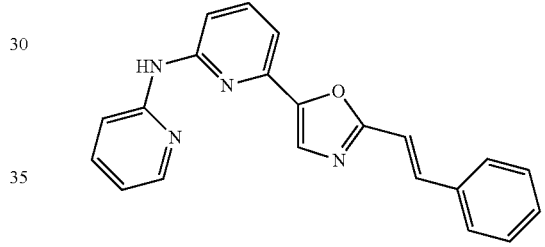

$^1$H NMR (DMSO-d$_6$, 300 MHz) δ=9.85 (s, 1H), 8.25 (d, J=4.6 Hz, 1H), 8.00 (d, J=8.4 Hz, 1H), 7.90-7.56 (m, 7H), 7.50-7.31 (m, 4H), 7.25 (d, J=16.4 Hz, 1H), 6.92 (m, 1H). (ESI+) m/z 341 (M+H)$^+$.

Example 007

(6-{2-[2-(4-Methoxy-phenyl)-vinyl]-oxazol-5-yl}-pyridin-2-yl)-pyridin-2-yl-amine

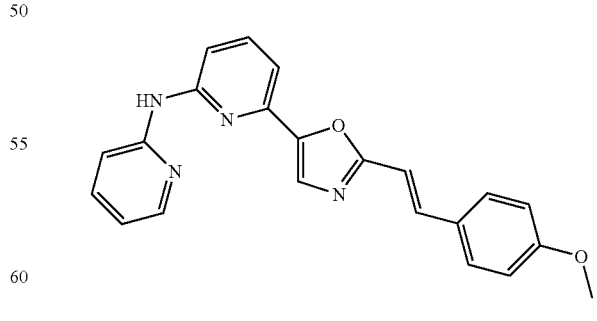

$^1$H NMR (DMSO-d$_6$, 300 MHz) δ=9.84 (s, 1H), 8.25 (d, J=3.8 Hz, 1H), 7.99 (d, J=8.5 Hz, 1H), 7.86-7.49 (m, 7H), 7.33 (d, J=7.3 Hz, 1H), 7.09 (d, J=16.4 Hz, 1H), 7.01 (d, J=8.4 Hz, 2H), 6.96-6.89 (m, 1H), 3.81 (s, 3H). (ESI+) m/z 371 (M+H)$^+$.

Examples 25 to 31 of Preferred Compounds of the Formula III are Depicted Below

Example 025

(6-{2-[2,6-Dimethyl-4-(2-morpholin-4-yl-ethoxy)-phenyl]-oxazol-5-yl}-pyridin-2-yl)-(4-methyl-pyridin-2-yl)-amine

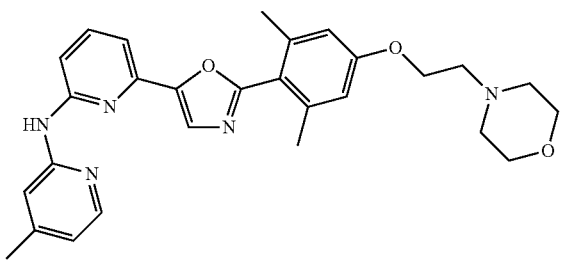 [SMILES: Cc1ccnc(Nc2cccc(-c3cnc(-c4c(C)cc(OCCN5CCOCC5)cc4C)o3)n2)c1]

$^1$H NMR (400 MHz, DMSO) δ 9.77 (s, 1H), 8.11 (d, J=5.1 Hz, 1H), 7.84 (s, 2H), 7.75 (t, J=7.9 Hz, 1H), 7.59 (d, J=8.3 Hz, 1H), 7.28 (d, J=7.4 Hz, 1H), 6.83 (s, 2H), 6.77 (d, J=5.2 Hz, 1H), 4.16 (t, J=5.7 Hz, 2H), 3.60 (t, J=4.7 Hz, 4H), 3.33-3.29 (m, 4H), 2.73 (t, J=5.6 Hz, 2H), 2.34-2.21 (m, 9H). (ESI+) m/z 486 (M+H)$^+$. Retention time=1.96 mins (method 1).

Example 026

(5-Chloro-pyridin-2-yl)-[6-(2-phenyl-oxazol-5-yl)-pyridin-2-yl]-amine

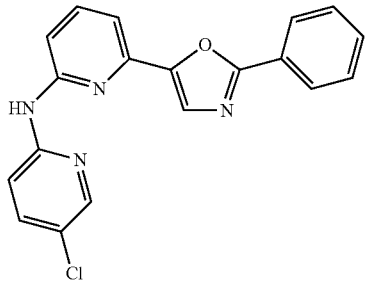 [SMILES: Clc1ccc(Nc2cccc(-c3cnc(-c4ccccc4)o3)n2)nc1]

(400 MHz, DMSO) δ 10.07 (s, 1H), 8.29 (d, J=2.6 Hz, 1H), 8.18-8.08 (m, 3H), 7.92 (s, 1H), 7.91-7.79 (m, 2H), 7.65-7.57 (m, 3H), 7.54 (d, J=8.4 Hz, 1H), 7.45 (d, J=7.4 Hz, 1H). (ESI+) m/z 349 (M+H)$^+$. Retention time=4.64 mins (method 1).

Example 027

(4-Methyl-piperazin-1-yl)-(3-{5-[3-(4-methyl-pyridin-2-ylamino)-phenyl]-oxazol-2-yl}-phenyl)-methanone

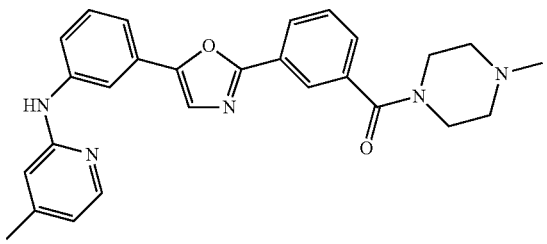

$^1$H NMR (400 MHz, DMSO) δ 9.15 (s, 1H), 8.13 (d, J=7.8 Hz, 1H), 8.11-8.04 (m, 2H), 8.02 (s, 1H), 7.86-7.80 (m, 1H), 7.79 (s, 1H), 7.66 (t, J=7.7 Hz, 1H), 7.55 (d, J=7.7 Hz, 1H), 7.41-7.32 (m, 2H), 6.69 (s, 1H), 6.65 (d, J=5.2 Hz, 1H), 3.79-3.55 (m, 2H), 3.47-3.35 (m, 2H), 2.45-2.35 (m, 2H), 2.34-2.27 (m, 2H), 2.25 (s, 3H), 2.20 (s, 3H). (ESI+) m/z 454 (M+H)$^+$. Retention time=1.90 mins (method 1).

Example 028

3-(4-Methyl-pyridin-2-ylamino)-5-(2-thiophen-3-yl-oxazol-5-yl)-benzonitrile

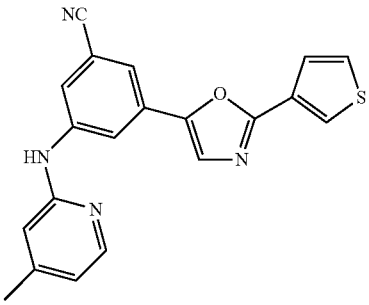 [SMILES: Cc1ccnc(Nc2cc(C#N)cc(-c3cnc(-c4ccsc4)o3)c2)c1]

$^1$H NMR (400 MHz, DMSO) δ 9.56 (s, 1H), 8.35-8.33 (m, 1H), 8.31 (dt, J=2.7, 1.2 Hz, 1H), 8.23-8.21 (m, 1H), 8.16 (d, J=5.0 Hz, 1H), 7.87 (d, J=1.1 Hz, 1H), 7.82-7.78 (m, 2H), 7.66 (dt, J=5.2, 1.3 Hz, 1H), 6.74 (d, J=5.1 Hz, 1H), 6.71 (s, 1H), 2.28 (s, 3H). (ESI+) m/z 359 (M+H)$^+$. Retention time=3.57 mins (method 1).

Example 029

4-{5-[6-(5-Methyl-pyridin-2-ylamino)-pyridin-2]-thiazol-2-yl}benzonitrile

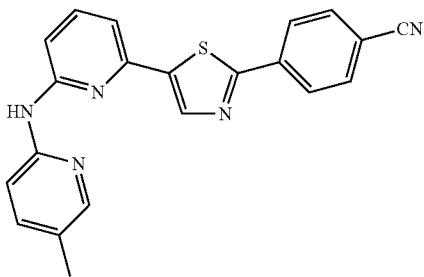 [SMILES: Cc1ccc(Nc2cccc(-c3cnc(-c4ccc(C#N)cc4)s3)n2)nc1]

$^1$H NMR (300 MHz, DMSO) δ 9.73 (s, 1H), 8.65 (s, 1H), 8.20 (d, J=7.1 Hz, 2H), 8.11 (s, 1H), 8.03-7.93 (m, 3H), 7.74 (t, J=7.9 Hz, 1H), 7.65 (d, J=8.2 Hz, 1H), 7.53 (d, J=7.5 Hz, 1H), 7.46 (d, J=8.3 Hz, 1H), 2.26 (s, 3H). (APCI+) m/z 370 (M+H)$^+$. Retention time=1.83 mins (method 2).

Example 030

{6-[2-(4-Methoxy-phenyl)-thiazol-5-yl]-pyridin-2-yl}-(6-methyl-pyridin-2-yl)-amine

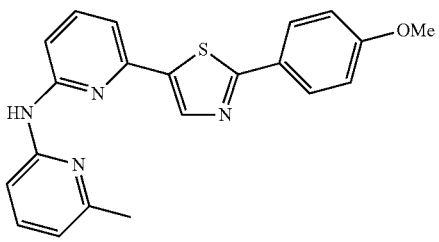 [SMILES: COc1ccc(-c2ncc(-c3cccc(Nc4cccc(C)n4)n3)s2)cc1]

¹H NMR (300 MHz, DMSO) δ 9.73 (br s, 1H), 8.47 (s, 1H), 7.96 (d, J=8.8 Hz, 2H), 7.90 (d, J=8.2 Hz, 1H), 7.76-7.65 (m, 2H), 7.47 (d, J=8.2 Hz, 2H), 7.10 (d, J=8.8 Hz, 2H), 6.81 (d, J=7.2 Hz, 1H), 3.85 (s, 3H), 2.42 (s, 3H). (APCI+) m/z 375 (M+H)$^+$. Retention time=2.54 mins (method 2).

Example 031

(4-Methyl-pyridin-2-yl)-{3-[2-(3-trifluoromethyl-phenyl)-oxazol-5]-phenyl}-amine

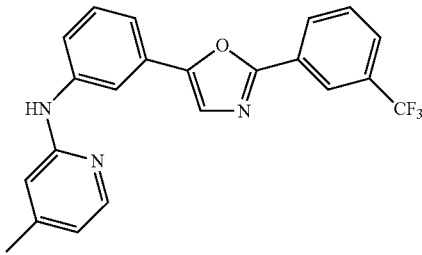 [SMILES: Cc1ccnc(Nc2cccc(-c3cnc(-c4cccc(C(F)(F)F)c4)o3)c2)c1]

¹H NMR (400 MHz, DMSO) δ 9.16 (s, 1H), 8.36 (d, J=7.7 Hz, 1H), 8.31 (s, 1H), 8.14 (s, 1H), 8.07 (d, J=5.2 Hz, 1H), 7.94 (d, J=8.0 Hz, 1H), 7.89-7.75 (m, 3H), 7.45-7.34 (m, 2H), 6.69 (s, 1H), 6.66 (d, J=5.3 Hz, 1H), 2.26 (s, 3H). (ESI+) m/z 396 (M+H)$^+$. Retention time=3.59 mins (method 1).

Examples of Compound Synthesis

The invention will be more fully understood by reference to the following preparative examples, but they should not be construed as limiting the scope of the invention. General: All chemicals used were commercial reagent grade products. Solvents were of anhydrous commercial grade and were used without further purification. THF was freshly distilled under a stream of argon before use. The progress of the reactions was monitored by thin layer chromatography using precoated silica gel 60F 254, Merck TLC plates, which were visualized under UV light. Multiplicities in ¹H NMR spectra are indicated as singlet (s), broad singlet (br s), doublet (d), triplet (t), quadruplet (q), and multiplet (m) and the NMR spectrum were performed either on a Bruker 300, 360 or 400 MHz spectrometer. Mass spectra were performed by Electrospray Ionisation Mass Spectrometry (ESI MS) in positive mode or by Atmospheric Pressure Chemical Ionization Mass Spectrometry (APCI MS) in positive mode LCMS methods: Method 1: This method was run on a Ultra-high performance liquid chromatography (HPLC) ACQUITY Waters instrument coupled to a TQD mass spectrometer. The gradient used was: starting at t=0.0 min with 5% of CH$_3$CN+0.1% Formic acid in Water+0.1% Formic acid until t=0.5 min; then a linear gradient from t=0.5 min to t=7.0 min reaching 100% CH$_3$CN+0.1% Formic acid; then staying at this state from t=7.0 min until t=10.0 min. The column used was a Waters HSS C18-1.8 μm, 2.1×50 mm. The detection instrument used was the triple quadrupole mass spectrometer (TQD) using ESI positive mode.

Method 2: This method was run on an HPLC 2695 Alliance Waters instrument coupled to a ZMD mass spectrometer. The gradient used was: starting at t=0.0 min with 0% of CH$_3$CN+0.04% Formic acid in water (10 mM); then a linear gradient to t=3.1 min reaching 100% of CH$_3$CN+0.04% Formic acid; then staying at this state to t=3.8 min and decreasing to =4.8 min to 0% of CH$_3$CN+0.04% Formic acid in water. The column used was a Sunfire 2,1×50 mm dp: 3.5 μm. The detection instrument used was the triple quadrupole mass spectrometer (TQD) using APCI positive mode.

ABBREVIATIONS

APCI+Atmospheric Pressure Chemical Ionization Mass Spectrometry (positive mode)
BINAP 2,2'-Bis(diphenylphosphino)-1,1'-binaphthalalene
CDCl$_3$ Deuterochloroform
DCM Dichloromethane
DMF N,N-Dimethylformamide
DMSO-d$_6$ Hexadeuterodimethyl sulfoxide
dppbz 1,2-bis(diphenylphosphino)benzene
ESI+Electrospray Ionisation Mass Spectrometry (positive mode)
EtOAc Ethyl acetate
EtOH Ethanol
h Hours
K$_2$CO$_3$ Potassium carbonate
LiOtBu Lithium tot-butoxide
LiHMDS Lithium bis(trimethylsilyl)amide
MeOH Methanol
MgSO$_4$ Magnesium sulfate
NaI Sodium iodide
NaOtBu Sodium tert-butoxide
Ni(cod)$_2$ Bis(cyclooctadiene)nickel(0)
Pd$_2$(dba)$_3$ Tris(dibenzylideneacetone)palladium(0)
Pd(PPh$_3$)$_4$ Tetrakis(triphenylphoshine)palladium(0)
SiO$_2$ Silica gel
TosMIC p-Toluenesulfonylmethyl isocyanide
THF Tetrahydrofuran Example 008

Preparation of (4-methyl-pyridin-2-yl)-(6-oxazol-5-yl-pyridin-2-yl)-amine

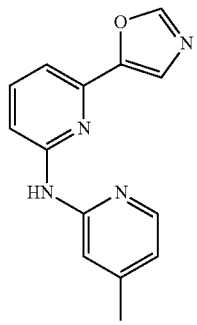 [SMILES: Cc1ccnc(Nc2cccc(-c3cnco3)n2)c1]

To a stirred solution of 6-bromopyridine-2-carboxaldehyde (5.90 g, 31.7 mmol) in methanol (150 ml) was added K$_2$CO$_3$ (5.25 g, 38.0 mmol) and TosMIC (7.43 g, 38.0 mmol). After stirring at ambient temperature for 1.5 h, the mixture was concentrated under vacuum and the product precipitated by addition of water. The solid was collected by filtration and dried in a vacuum dessicator at 50° C. to afford 2-bromo-6-oxazol-5-ylpyridine compound as a beige solid (6.81 g, 95% yield). ¹H NMR (CDCl$_3$, 300 MHz): δ=7.97 (s, 1H), 7.76 (s, 1H), 7.65-7.57 (m, 2H), 7.48-7.37 (m, 1H).

A sealed tube with a teflon screw cap was charged with 2-bromo-6-oxazol-5-ylpyridine (4.00 g, 17.8 mmol), 2-amino-4-methylpyridine (2.30 g, 21.3 mmol), Pd$_2$(dba)$_3$ (320 mg, 0.349 mmol), (±)-BINAP (440 mg, 0.707 mmol), NaOtBu (2.40 g, 25.0 mmol) and anhydrous toluene (80 ml) and heated to 90° C. with stirring for 1 h. The cooled reaction mixture was treated with water and extracted with DCM. The combined organics were dried over MgSO$_4$, filtered and evaporated under reduced pressure before purification by column chromatography on SiO$_2$, eluting with 30% EtOAc in cyclohexane to afford the title compound as a yellow-orange solid (1.89 g, 42%). $^1$H NMR (300 MHz, DMSO-d$_6$): δ=9.78 (s, 1H), 8.53 (s, 1H), 8.11 (d, J=5.0 Hz, 1H), 7.84-7.59 (m, 4H), 7.25 (d, J=7.3 Hz, 1H), 6.76 (d, J=5.0 Hz, 1H), 2.32 (s, 3H). (ESI+) m/z 253 (M+H).

Example 009

Preparation of 4-(2-{5-[6-(4-Methyl-pyridin-2-ylamino)-pyridin-2-yl]-oxazol-2-yl}-vinyl)-benzonitrile

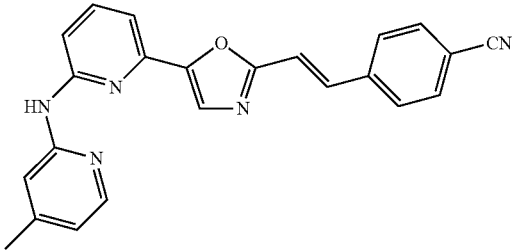 [SMILES: Cc1ccnc(Nc2cccc(-c3cnc(/C=C/c4ccc(C#N)cc4)o3)n2)c1]

A sealed tube was charged with a mixture of (4-methyl-pyridin-2-yl)-(6-oxazol-5-yl-pyridin-2-yl)-amine (200 mg, 0.793 mmol), 4-(2-bromovinyl)-benzonitrile (330 mg, 1.59 mmol), Pd(PPh$_3$)$_4$ (46 mg, 0.0396 mmol), LiOtBu (127 mg, 1.59 mmol) and anhydrous 1,4-dioxane (5 ml) and heated to 100° C. with stirring for 2 h. The cooled reaction mixture was treated with water and extracted with DCM. The combined organics were dried over MgSO$_4$, filtered and evaporated under reduced pressure before purification by column chromatography on SiO$_2$, eluting with 50% EtOAc in cyclohexane to afford the title compound as a yellow solid (76 mg, 25%). $^1$H NMR (300 MHz, DMSO-d$_6$) δ=9.79 (s, 1H), 8.12 (d, J=5.1 Hz, 1H), 7.97 (d, J=8.3 Hz, 2H), 7.90 (d, J=8.2 Hz, 2H), 7.86-7.61 (m, 5H), 7.46 (d, J=16.3 Hz, 1H), 7.36 (d, J=7.3 Hz, 1H), 6.78 (d, J=4.7 Hz, 1H), 2.35 (s, 3H). (ESI+) m/z 380 (M+H).

Example 010

Preparation of 4-(2-{5-[6-(4-Methyl-pyridin-2-ylamino)-pyridin-2-yl]-oxazol-2-yl}-ethyl)-benzonitrile

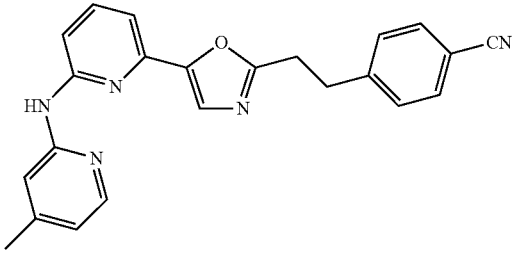 [SMILES: Cc1ccnc(Nc2cccc(-c3cnc(CCc4ccc(C#N)cc4)o3)n2)c1]

A mixture of the 4-(2-{5-[6-(4-methyl-pyridin-2-ylamino)-pyridin-2-yl]-oxazol-2-yl}-vinyl)-benzonitrile (72 mg, 0.189 mmol) and 10% palladium on activated carbon (27 mg) in MeOH and DCM (10 ml each) was stirred vigorously under an atmosphere of hydrogen at ambient temperature and pressure for 24 h. Further catalyst (27 mg) was added and the mixture stirred for a further 18 h. The mixture was filtered and evaporated under reduced pressure before trituration from DCM/pentane to afford the title compound as a pale yellow solid (32 mg, 44%). $^1$H NMR (300 MHz, DMSO-d$_6$) δ 9.75 (s, 1H), 8.10 (d, J=5.0 Hz, 1H), 7.89-7.39 (m, 8H), 7.17 (d, J=7.2 Hz, 1H), 6.73 (t, J=13.6 Hz, 1H), 3.22 (s, 4H), 2.31 (s, 3H). (ESI+) m/z 382 (M+H).

Example 011

Preparation of (4-methyl-pyridin-2-yl)-[6-(2-pyridin-3-yl-oxazol-5-yl)-pyridin-2-yl]-amine

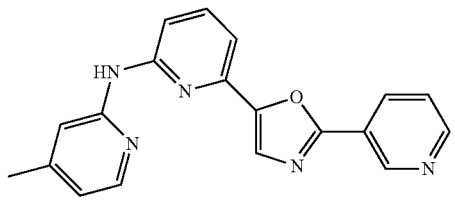 [SMILES: Cc1ccnc(Nc2cccc(-c3cnc(-c4cccnc4)o3)n2)c1]

Prepared as for 4-(2-{5-[6-(4-methyl-pyridin-2-ylamino)-pyridin-2-yl]-oxazol-2-yl}-vinyl)-benzonitrile above using (4-methyl-pyridin-2-yl)-(6-oxazol-5-yl-pyridin-2-yl)-amine, 3-bromopyridine, Pd(PPh$_3$)$_4$, LiOtBu and anhydrous 1,4-dioxane to afford the title compound as a pale yellow solid (8%). $^1$H NMR (300 MHz, DMSO-d$_6$) δ=9.81 (s, 1H), 9.31 (s, 1H), 8.76 (d, J=4.8 Hz, 1H), 8.46 (d, J=8.1 Hz, 1H), 8.12 (d, J=5.0 Hz, 1H), 7.91 (s, 2H), 7.84-7.76 (m, 1H), 7.69-7.52 (m, 2H), 7.45 (d, J=7.4 Hz, 1H), 6.79 (d, J=5.0 Hz, 1H), 2.36 (s, 3H). (ESI+) m/z 330 (M+H).

Example 032

Preparation of N-(2-Hydroxy-ethyl)-N-methyl-3-{5-[6-(4-methyl-pyridin-2-ylamino)-pyridin-2-yl]-oxazol-2-yl}-benzenesulfonamide

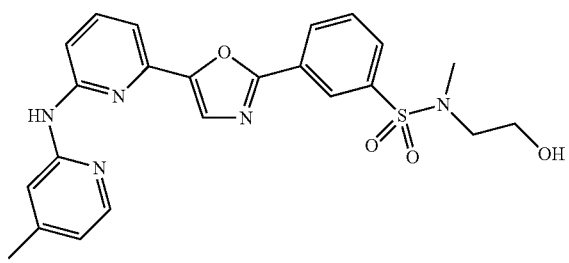 [SMILES: Cc1ccnc(Nc2cccc(-c3cnc(-c4cccc(S(=O)(=O)N(C)CCO)c4)o3)n2)c1]

Prepared as for 4-(2-{5-[6-(4-methyl-pyridin-2-ylamino)-pyridin-2-yl]-oxazol-2-yl}-vinyl)-benzonitrile above using (4-methyl-pyridin-2-yl)-(6-oxazol-5-yl-pyridin-2-yl)-amine, 3-bromo-N-(2-hydroxy-ethyl)-N-methyl-benzenesulfonamide, Pd(PPh$_3$)$_4$, LiOtBu and anhydrous 1,4-dioxane to afford the title compound as a pale yellow solid (24%). $^1$H NMR (400 MHz, CDCl$_3$) δ 9.81 (s, 1H), 8.45-8.34 (m, 2H), 8.12 (d, J=5.0 Hz, 1H), 8.01-7.77 (m, 5H), 7.66 (d, J=8.4 Hz, 1H), 7.46 (d, J=7.4 Hz, 1H), 6.79 (d, J=5.0 Hz, 1H), 4.83 (t, J=5.5 Hz, 1H), 3.55 (q, J=5.8 Hz, 2H), 3.11 (t, J=5.9 Hz, 2H), 2.81 (d, J=8.0 Hz, 3H), 2.36 (s, 3H). (ESI+) m/z 466 (M+H)$^+$. Retention time=2.45 mins (method 1).

Example 033

Preparation of (4-methyl-pyridin-2-yl)-{6-[2-(3-pyrrolidin-1-ylmethyl-phenyl)-oxazol-5-yl]-pyridin-2-yl}-amine hydrochloride

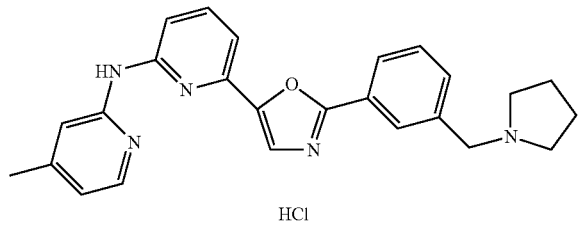 [SMILES: Cc1ccnc(Nc2cccc(-c3cnc(-c4cccc(CN5CCCC5)c4)o3)n2)c1 ; Cl]

HCl

A solution of 3-iodobenzyl alcohol (600 mg, 2.56 mmol) in DCM (3 ml) was treated with thionyl chloride (3 ml, 41.3 mmol) and stirred at ambient temperature for 18 h, before addition of further thionyl chloride (1 ml, 13.7 mmol) and heating to reflux for 12 h. The cooled solution was basified with 50% NaOH, diluted with water and extracted with DCM. The combined organics were dried over MgSO$_4$, filtered and evaporated to afford a clear syrup which crystallises on standing to give 3-iodobenzyl chloride as a white solid (650 mg, quant.).

A solution of 3-iodobenzyl chloride (100 mg, 0.396 mmol) in 1,4-dioxane (3 ml) was treated with pyrrolidine (0.5 ml, 6.02 mmol) and heated to reflux for 5 h. The cooled mixture was evaporated to dryness and treated with EtOAc and water. The organics were separated, dried over MgSO4, filtered and evaporated to afford 1-(3-iodo-benzyl)-pyrrolidine as a clear syrup (110 mg, 97%).

(4-Methyl-pyridin-2-yl)-{6-[2-(3-pyrrolidin-1-ylmethyl-phenyl)-oxazol-5-yl]-pyridin-2-yl}-amine was then prepared as for 4-(2-{5-[6-(4-methyl-pyridin-2-ylamino)-pyridin-2-yl]-oxazol-2-yl}-vinyl)-benzonitrile above using (4-methyl-pyridin-2-yl)-(6-oxazol-5-yl-pyridin-2-yl)-amine (Example 008), 1-(3-iodo-benzyl)-pyrrolidine, Pd(PPh$_3$)$_4$, LiOtBu and anhydrous 1,4-dioxane. The isolated material was taken up in EtOAc and treated with HCl (2M in ether) to afford the title compound as a beige solid (35%) after evaporation under vacuum. $^1$H NMR (400 MHz, DMSO-d$_6$) δ 12.65 (s, 1H), 11.30 (s, 1H), 8.53-8.47 (m, 2H), 8.33 (s, 1H), 8.19 (d, J=7.6 Hz, 1H), 8.07 (t, J=7.9 Hz, 1H), 7.85 (d, J=7.8 Hz, 1H), 7.80 (d, J=7.6 Hz, 1H), 7.67 (t, J=7.7 Hz, 1H), 7.52 (s, 1H), 7.38 (d, J=8.3 Hz, 1H), 7.24 (d, J=6.4 Hz, 1H), 4.48 (d, J=5.6 Hz, 2H), 3.42-3.29 (m, 4H), 2.51 (s, 3H), 2.09-1.86 (m, 4H). (ESI+) m/z 412 (M+H)$^+$. Retention time=1.88 mins (method 1).

Example 034

Preparation of (4-methyl-pyridin-2-yl)-{6-[2-(3-morpholin-4-ylmethyl-phenyl)-oxazol-5-yl]-pyridin-2-yl}-amine hydrochloride

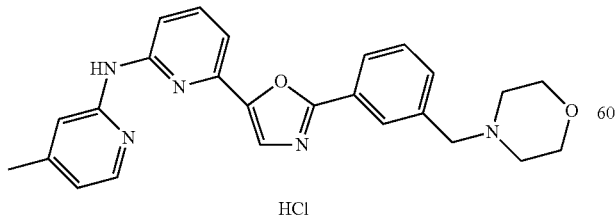

HCl 4-(3-Iodo-benzyl)-morpholine was prepared as described for 1-(3-iodo-benzyl)-pyrrolidine above. (4-Methyl-pyridin-2-yl)-{6-[2-(3-morpholin-4-ylmethyl-phenyl)-oxazol-5-yl]-pyridin-2-yl}-amine was then prepared as for (4-methyl-pyridin-2-yl)-{6-[2-(3-pyrrolidin-1-ylmethyl-phenyl)-oxazol-5-yl]-pyridin-2-yl}-amine hydrochloride above using (4-methyl-pyridin-2-yl)-(6-oxazol-5-yl-pyridin-2-yl)-amine (Example 008), 4-(3-iodo-benzyl)-morpholine, Pd(PPh$_3$)$_4$, LiOtBu and anhydrous 1,4-dioxane then HCl (2M in ether) to afford the title compound as a beige solid (8%). $^1$H NMR (400 MHz, DMSO-d$_6$) δ 12.69-11.90 (m, 1H), 11.90-11.22 (m, 1H), 8.51 (s, 1H), 8.46 (d, J=5.8 Hz, 1H), 8.28 (s, 1H), 8.22 (d, J=7.7 Hz, 1H), 8.05 (t, J=7.9 Hz, 1H), 7.85 (d, J=7.5 Hz, 1H), 7.75 (d, J=7.7 Hz, 1H), 7.70 (t, J=7.7 Hz, 1H), 7.57 (s, 1H), 7.41 (d, J=8.3 Hz, 1H), 7.19 (d, J=4.5 Hz, 1H), 4.47 (s, 2H), 3.95 (d, J=11.8 Hz, 2H), 3.85 (t, J=11.8 Hz, 2H), 3.27 (d, J=11.8 Hz, 2H), 3.20-3.10 (m, 2H), 2.50 (s, 3H). (ESI+) m/z 428 (M+H)$^+$. Retention time=1.80 mins (method 1).

Example 012

Preparation of [6-(2-chloro-oxazol-5-yl)-pyridin-2-yl]-(4-methyl-pyridin-2-yl)-amine

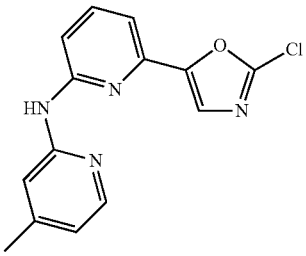 [SMILES: Cc1ccnc(Nc2cccc(-c3cnc(Cl)o3)n2)c1]

A stirred solution of (4-methyl-pyridin-2-yl)-(6-oxazol-5-yl-pyridin-2-yl)-amine (Example 008, 1.00 g, 3.96 mmol) in dry distilled THF (50 ml) under an argon atmosphere was cooled to −78° C. then treated with LiHMDS (1M in THF) (5.96 ml, 5.96 mmol) dropwise. After stirring at −78° C. for 15 mins, the solution was treated with C$_2$Cl$_6$ (1.41 g, 5.96 mmol) in one portion and the reaction allowed to return to ambient temperature. The reaction was then cooled to −78° C. and treated with LiHMDS (1M in THF) (5.96 ml, 5.96 mmol) dropwise then C$_2$Cl$_6$ (1.41 g, 5.96 mmol) and warmed to room temperature and stirred for 1 h. The mixture was treated with water and extracted with DCM. The combined organics were dried over MgSO$_4$, filtered and evaporated under reduced pressure before purification by column chromatography on SiO$_2$, eluting with 30% EtOAc in cyclohexane to afford the title compound as an off-white solid (836 mg, 74%). $^1$H NMR (300 MHz, DMSO-d$_6$) δ=9.82 (s, 1H), 8.10 (d, J=5.0 Hz, 1H), 7.84-7.63 (m, 4H), 7.24 (d, J=7.0 Hz, 1H), 6.76 (d, J=4.6 Hz, 1H), 2.31 (s, 3H).

Example 035

Preparation of (5-chloro-pyridin-2-yl)-[6-(2-thiophen-3-yl-oxazol-5-yl)-pyridin-2-yl]-amine

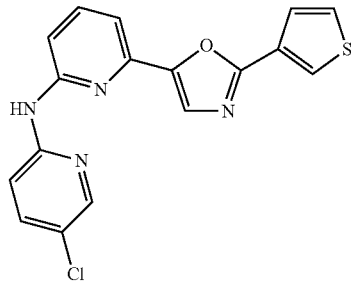 [SMILES: Clc1ccc(Nc2cccc(-c3cnc(-c4ccsc4)o3)n2)nc1]

[6-(2-chloro-oxazol-5-yl)-pyridin-2-yl]-(5-chloro-pyridin-2-yl)-amine was prepared by the same sequence of reactions as described above for the preparation of [6-(2-chloro-oxazol-5-yl)-pyridin-2-yl]-(4-methyl-pyridin-2-yl)-amine (Example 012) culminating in the chlorination with LiHMDS and $C_2Cl_6$ to afford the desired chloro-oxazole.

A solution of [6-(2-chloro-oxazol-5-yl)-pyridin-2-yl]-(5-chloro-pyridin-2-yl)-amine (50 mg, 0.162 mmol) in THF (4 ml) and water (2 ml) was treated with 3-thiopheneboronic acid (25 mg, 0.195 mmol), $Pd(PPh_3)_4$ (19 mg, 0.0162 mmol) and $K_2CO_3$ (50 mg, 0.358 mmol) before heating to 100° C. for 60 h. The cooled mixture was treated with water and extracted with DCM. The combined organics were dried over $MgSO_4$, filtered and evaporated under reduced pressure before purification by column chromatography on $SiO_2$, eluting with 1% EtOH in DCM to afford the title compound as an off-white solid (51 mg, 89%). $^1$H NMR (400 MHz, DMSO-$d_6$) δ 10.05 (s, 1H), 8.33-8.31 (m, 1H), 8.28 (d, J=2.5 Hz, 1H), 8.15 (d, J=9.0 Hz, 1H), 7.89 (dd, J=9.0, 2.7 Hz, 1H), 7.85 (s, 1H), 7.83-7.77 (m, 2H), 7.69-7.65 (m, 1H), 7.49 (d, J=8.3 Hz, 1H), 7.40 (d, J=7.4 Hz, 1H). (ESI+) m/z 355 (M+H)$^+$. Retention time=4.28 mins (method 1).

Example 036

Preparation of {6-[2-(1H-indol-5-yl)-oxazol-5-yl]-pyridin-2-yl}-pyrazin-2-yl-amine

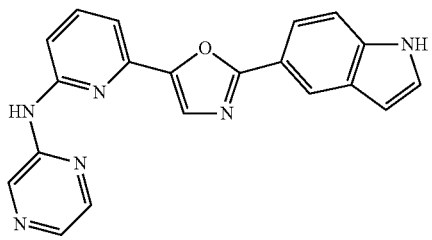 [SMILES: c1cc(Nc2cnccn2)nc(-c2cnc(-c3ccc4[nH]ccc4c3)o2)c1]

Prepared as for (5-chloro-pyridin-2-yl)-[6-(2-thiophen-3-yl-oxazol-5-yl)-pyridin-2-yl]-amine from [6-(2-chloro-oxazol-5-yl)-pyridin-2-yl]-pyrazin-2-yl-amine, indole-5-boronic acid, $Pd(PPh_3)_4$ and $K_2CO_3$ in THF/water to afford the title compound as a beige solid. $^1$H NMR (400 MHz, DMSO-$d_6$) δ 11.37 (s, 1H), 10.08 (s, 1H), 9.28 (s, 1H), 8.38 (s, 1H), 8.30-8.25 (m, 1H), 8.16 (d, J=2.6 Hz, 1H), 7.93-7.81 (m, 2H), 7.79 (s, 1H), 7.65 (d, J=8.3 Hz, 1H), 7.58 (d, J=8.5 Hz, 1H), 7.51-7.42 (m, 2H), 6.62 (s, 1H). (ESI+) m/z 338 (M+H)$^+$. Retention time=1.81 mins (method 1).

Example 037

Preparation of {6-[2-(1H-indol-5-yl)-oxazol-5-yl]-5-methyl-pyridin-2-yl}-(4-methyl-pyridin-2-yl)-amine

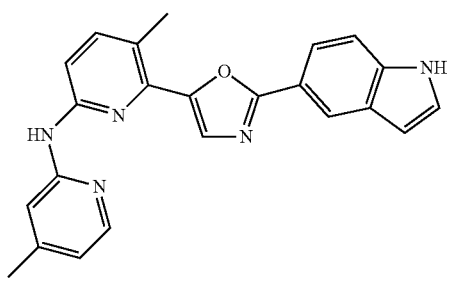 [SMILES: Cc1ccnc(Nc2ccc(C)c(-c3cnc(-c4ccc5[nH]ccc5c4)o3)n2)c1]

2-Bromo-6-chloro-3-methyl-pyridine was prepared from 2-chloro-5-methylpyridine by by the method of Gros P. and Fort Y. (*J. Org. Chem.*, 2005, 8220). A solution of n-BuLi (1.6M in hexanes) (2.0 ml, 3.30 mmol) in dry THF (6 ml) at −78° C. under argon was treated dropwise with a solution of 2-bromo-6-chloro-3-methyl-pyridine (642 mg, 3.10 mmol) in dry THF (4 ml) and stirred at this temperature for 30 minutes. A solution of DMF (385 µl, 4.70 mmol) in dry THF (1 ml) was added dropwise and stirred at −78° C. for a further 45 minutes before warming to ambient temperature. The reaction was quenched with MeOH (3 ml), treated with water and extracted with EtOAc. The combined organics were dried over $MgSO_4$, filtered and evaporated under reduced pressure before purification by column chromatography on $SiO_2$, eluting with 2% EtOH in DCM to afford 6-chloro-3-methyl-pyridine-2-carbaldehyde as a yellow solid (217 mg, 45%). $^1$H NMR (400 MHz, CDCl$_3$) δ 10.09 (s, 1H), 7.60 (d, J=7.7 Hz, 1H), 7.42 (d, J=7.7 Hz, 1H), 2.64 (s, 3H).

[6-(2-Chloro-oxazol-5-yl)-5-methyl-pyridin-2-yl]-(4-methyl-pyridin-2-yl)-amine was then prepared by the same sequence of reactions as described above for the preparation of [6-(2-chloro-oxazol-5-yl)-pyridin-2-yl]-(4-methyl-pyridin-2-yl)-amine culminating in the chlorination with LiHMDS and $C_2Cl_6$ to afford the desired chloro-oxazole which was used without further purification.

{6-[2-(1H-indol-5-yl)-oxazol-5-yl]-5-methyl-pyridin-2-yl}-(4-methyl-pyridin-2-yl)-amine was then prepared as described for (5-chloro-pyridin-2-yl)-[6-(2-thiophen-3-yl-oxazol-5-yl)-pyridin-2-yl]-amine above using (5-chloro-pyridin-2-yl)-[6-(2-thiophen-3-yl-oxazol-5-yl)-pyridin-2-yl]-amine, indole-5-boronic acid, $Pd(PPh_3)_4$ and $K_2CO_3$ in THF/water to afford {6-[2-(1H-indol-5-yl)-oxazol-5-yl]-5-methyl-pyridin-2-yl}-(4-methyl-pyridin-2-yl)-amine as a beige solid (32%). $^1$H NMR (400 MHz, DMSO-$d_6$) δ 11.45 (s, 1H), 9.62 (s, 1H), 8.36 (s, 1H), 8.14 (s, 1H), 8.11 (d, J=5.1 Hz, 1H), 7.90 (dd, J=8.5, 1.5 Hz, 1H), 7.72 (s, 1H), 7.65-7.54 (m, 2H), 7.51-7.46 (m, 1H), 7.40 (d, J=8.4 Hz, 1H), 6.77 (d, J=4.9 Hz, 1H), 6.61 (s, 1H), 2.51 (s, 3H), 2.39 (s, 3H). (ESI+) m/z 382 (M+H)$^+$. Retention time=2.98 mins (method 1).

Example 013

Preparation of [6-(2-Cylohexylsulfanyl-oxazol-5-yl)-pyridin-2-yl]-(4-methyl-pyridin-2-yl)-amine

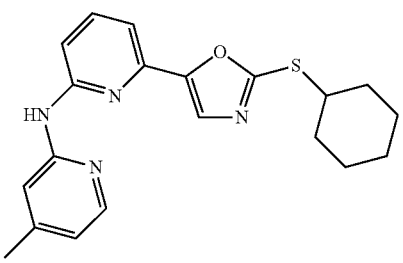 [SMILES: Cc1ccnc(Nc2cccc(-c3cnc(SC4CCCCC4)o3)n2)c1]

A mixture of [6-(2-chloro-oxazol-5-yl)-pyridin-2-yl]-(4-methyl-pyridin-2-yl)-amine (50 mg, 0.174 mmol), $K_2CO_3$ (72 mg, 0.523 mmol) and cyclohexanethiol (64 µl, 0.523 mmol) in iPrOH (5 ml) were heated to reflux for 18 h. The cooled mixture was treated with water and extracted with DCM. The combined organics were dried over $MgSO_4$, filtered and evaporated under reduced pressure to a yellow gum. The gum was taken up in a minimum of DCM and precipitated with n-pentane to afford the title compound as a beige solid (45 mg, 71%). $^1$H NMR (300 MHz, DMSO-$d_6$) δ 9.76 (s, 1H), 8.10 (s, 1H), 7.56-7.78 (m, 4H), 7.17 (d, J=5.9 Hz, 1H), 6.75 (s, 1H), 3.71 (m, 1H), 2.31 (s, 3H), 2.08 (m, 2H), 1.64 (m, 8H). (ESI+) m/z 367 (M+H)⁺.

Example 014

Preparation of 5-[6-(4-methylpyridin-2-ylamino) pyridin-2-yl]-N-(pyridin-4-ylmethyl)oxazol-2-amine

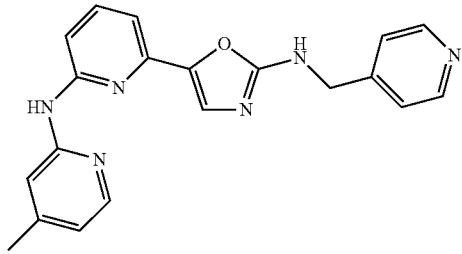 [SMILES: Cc1ccnc(Nc2cccc(-c3cnc(NCc4ccncc4)o3)n2)c1]

A solution of [6-(2-chloro-oxazol-5-yl)-pyridin-2-yl]-(4-methyl-pyridin-2-yl)-amine (50 mg, 0.174 mmol) in iPrOH (5 ml) was treated with 4-aminomethylpyridine (53 μl) and heated to reflux for 40 h. The cooled mixture was treated with water and extracted with DCM. The combined organics were dried over MgSO₄, filtered and evaporated under reduced pressure before purification by column chromatography on Al₂O₃ (Brockman grade III, 7% H₂O), eluting with 2% EtOH in DCM. Precipitation from DCM with n-pentane afforded the title compound as pale yellow solid (34 mg, 55%). ¹H NMR (300 MHz, DMSO-d₆) δ 9.61 (s, 1H), 8.52 (d, J=4.6 Hz, 2H), 8.25 (t, J=5.8 Hz, 1H), 8.08 (d, J=5.0 Hz, 1H), 7.73 (s, 1H), 7.64 (t, J=7.9 Hz, 1H), 7.47 (d, J=8.3 Hz, 1H), 7.36 (d, J=4.9 Hz, 2H), 7.29 (s, 1H), 6.92 (d, J=7.6 Hz, 1H), 6.73 (d, J=5.0 Hz, 1H), 4.49 (d, J=5.7 Hz, 2H), 2.29 (s, 3H). (ESI+) m/z 359 (M+H)⁺.

Example 015

Preparation of N-(4-Methoxybenzyl)-5-[6-(4-methylpyridin-2-ylamino)pyridin-2-yl]oxazol-2-amine

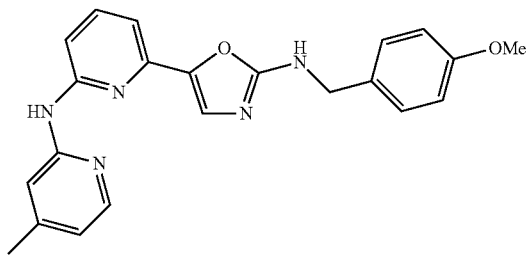 [SMILES: COc1ccc(CNc2ncc(-c3cccc(Nc4cc(C)ccn4)n3)o2)cc1]

Prepared as for 5-[6-(4-methylpyridin-2-ylamino)pyridin-2-yl]-N-(pyridin-4-ylmethyl)oxazol-2-amine above from the chlorooxazole and 4-methoxybenzylamine in iPrOH. ¹H NMR (300 MHz, DMSO-d₆) δ 9.60 (s, 1H), 8.18-8.00 (m, 2H), 7.75 (s, 1H), 7.63 (t, J=7.9 Hz, 1H), 7.45 (d, J=8.3 Hz, 1H), 7.38-7.24 (m, 3H), 6.95-6.86 (m, 3H), 6.73 (d, J=5.0 Hz, 1H), 4.37 (d, J=5.9 Hz, 2H), 3.72 (s, 3H), 2.30 (s, 3H). (ESI+) m/z 388 (M+H)⁺.

Example 038

Preparation of 4-{5-[6-(5-methyl-thiazol-2-ylamino)-pyridin-2-yl]-oxazol-2-yl}-piperazin-2-one

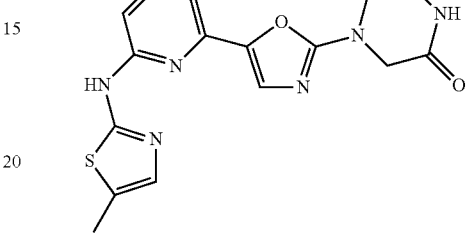

Prepared as for 5-[6-(4-methylpyridin-2-ylamino)pyridin-2-yl]-N-(pyridin-4-ylmethyl)oxazol-2-amine above from [6-(2-Chloro-oxazol-5-yl)-pyridin-2-yl]-(5-methyl-thiazol-2-yl)-amine and 2-oxopiperazine in iPrOH. ¹H NMR (400 MHz, DMSO-d₆) δ 11.08 (s, 1H), 8.14 (s, 1H), 7.68 (t, J=7.9 Hz, 1H), 7.59 (s, 1H), 7.16-6.97 (m, 2H), 6.83 (d, J=8.2 Hz, 1H), 4.11 (s, 2H), 3.86-3.63 (m, 2H), 3.43-3.32 (m, 2H), 2.37 (s, 3H). (ESI+) m/z 357 (M+H)⁺. Retention time=1.91 mins (method 1).

Example 039

Preparation of {6-[2-(4-Methyl-piperazin-1-yl)-oxazol-5]-pyridin-2-yl}-(3-trifluoromethyl-phenyl)-amine

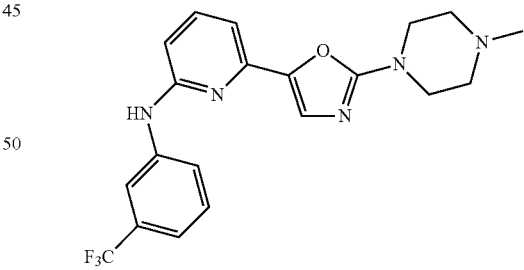

Prepared as for 5-[6-(4-methylpyridin-2-ylamino)pyridin-2-yl]-N-(pyridin-4-ylmethyl)oxazol-2-amine above from [6-(2-Chloro-oxazol-5-yl)-pyridin-2-yl]-(3-trifluoromethyl-phenyl)-amine and N-methylpiperazine in iPrOH. ¹H NMR (400 MHz, DMSO-d₆) δ 9.54 (s, 1H), 8.66 (s, 1H), 7.72 (d, J=8.0 Hz, 1H), 7.63 (t, J=7.9 Hz, 1H), 7.50 (t, J=7.9 Hz, 1H), 7.36 (s, 1H), 7.21 (d, J=7.5 Hz, 1H), 7.00 (d, J=7.5 Hz, 1H), 6.70 (d, J=8.3 Hz, 1H), 3.58-3.48 (m, 4H), 2.46-2.37 (m, 4H), 2.23 (s, 3H). (ESI+) m/z 404 (M+H)⁺. Retention time=3.01 mins (method 1).

Example 040

Preparation of (6-{2-[4-(2-Methoxy-ethyl)-piperazin-1-yl]-oxazol-5-yl}-pyridin-2-yl)-(4-methyl-pyridin-2-yl)-amine

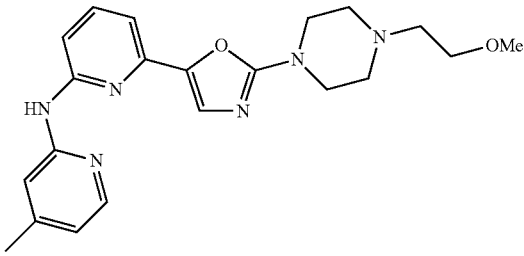 [SMILES: COCCN1CCN(c2ncc(-c3cccc(Nc4cc(C)ccn4)n3)o2)CC1]

A solution of N-Boc-piperazine (1.00 g, 5.31 mmol) in acetonitrile (30 ml) was treated with $K_2CO_3$ (2.20 g, 15.9 mmol) and (2-bromoethyl)methyl ether (812 μl, 5.84 mmol) and heated to 80° C. for 18 h. The cooled mixture was diluted with water and extracted with DCM. The combined organcs were dried over $MgSO_4$, filtered and evaporated and the residue purified by column chromatography on $SiO_2$, eluting with 5% EtOH in DCM to afford 1-Boc-4-(2-methoxy-ethyl)-piperazine as a clear oil (978 mg, 76%). $^1$H NMR (400 MHz, DMSO-$d_6$) δ 3.41 (t, J=5.8 Hz, 2H), 3.29-3.25 (m, 4H), 3.21 (s, 3H), 2.45 (t, J=5.8 Hz, 2H), 2.33 (t, J=5.0 Hz, 4H), 1.38 (s, 9H).

A solution of 1-Boc-4-(2-methoxy-ethyl)-piperazine (264 mg, 1.08 mmol) in DCM (10 ml) was treated with TFA (1 ml) and stirred at ambient temperature for 2 h. The solution was evaporated to dryness and the crude mixture containing 1-(2-methoxy-ethyl)-piperazine trifluoroacetic acid salt was used without further purification.

(6-{2-[4-(2-Methoxy-ethyl)-piperazin-1-yl]-oxazol-5-yl}-pyridin-2-yl)-(4-methyl-pyridin-2-yl)-amine was then prepared as for 5-[6-(4-methylpyridin-2-ylamino)pyridin-2-yl]-N-(pyridin-4-ylmethyl)oxazol-2-amine above from [6-(2-chloro-oxazol-5-yl)-pyridin-2-yl]-(4-methyl-pyridin-2-yl)-amine and 1-(2-methoxy-ethyl)-piperazine trifluoroacetic acid salt in iPrOH. $^1$H NMR (400 MHz, DMSO-$d_6$) δ 9.59 (s, 1H), 8.08 (d, J=5.1 Hz, 1H), 7.86 (s, 1H), 7.63 (t, J=8.0 Hz, 1H), 7.41-7.36 (m, 2H), 7.03 (d, J=7.4 Hz, 1H), 6.73 (d, J=4.9 Hz, 1H), 3.52 (t, J=4.7 Hz, 4H), 3.47 (t, J=5.7 Hz, 2H), 3.25 (s, 3H), 2.63-2.52 (m, 6H), 2.30 (s, 3H). (ESI+) m/z 395 (M+H)$^+$. Retention time=1.54 mins (method 1).

Example 041

Preparation of 1-(2-Methoxy-ethyl)-4-{5-[3-(4-methyl-pyrimidin-2-ylamino)-phenyl]-oxazol-2-yl}-piperazin-2-one

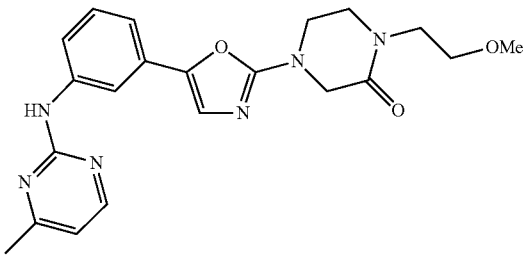 [SMILES: COCCN1CCN(c2ncc(-c3cccc(Nc4nccc(C)n4)c3)o2)CC1=O]

Prepared as for 5-[6-(4-methylpyridin-2-ylamino)pyridin-2-yl]-N-(pyridin-4-ylmethyl)oxazol-2-amine above from [3-(2-chloro-oxazol-5-yl)-phenyl]-(4-methyl-pyrimidin-2-yl)-amine and 1-(2-methoxy-ethyl)-2-oxopiperazine trifluoroacetic acid salt in iPrOH. $^1$H NMR (400 MHz, DMSO-$d_6$) δ 9.56 (s, 1H), 8.35 (d, J=5.0 Hz, 1H), 8.10 (s, 1H), 7.64 (d, J=8.0 Hz, 1H), 7.31-7.20 (m, 2H), 7.15 (d, J=7.6 Hz, 1H), 6.76 (d, J=5.0 Hz, 1H), 4.10 (s, 2H), 3.79-3.72 (m, 2H), 3.58-3.46 (m, 6H), 3.25 (dd, J=2.7, 2.2 Hz, 3H), 2.38 (s, 3H). (ESI+) m/z 409 (M+H)$^+$. Retention time=2.94 mins (method 1).

Example 042

Preparation of 3-{2-[(2-methoxy-ethyl)-methyl-amino]-oxazol-5-yl}-5-(4-methyl-pyridin-2-ylamino)-benzonitrile

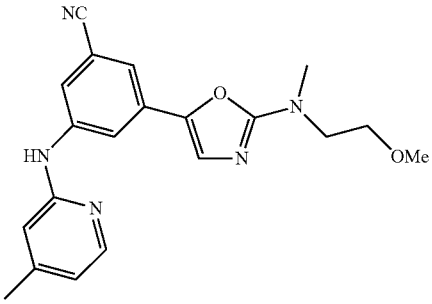 [SMILES: COCCN(C)c1ncc(-c2cc(C#N)cc(Nc3cc(C)ccn3)c2)o1]

Prepared as for 5-[6-(4-methylpyridin-2-ylamino)pyridin-2-yl]-*(pyridin-4-ylmethyl)-oxazol-2-amine above from 3-(2-chloro-oxazol-5-yl)-5-(4-methyl-pyridin-2-ylamino)-benzonitrile and N-(2-methoxyethyl)methylamine in iPrOH. (400 MHz, DMSO-$d_6$) δ 9.38 (s, 1H), 8.18 (d, J=1.7 Hz, 1H), 8.10 (d, J=5.1 Hz, 1H), 7.87 (t, J=1.7 Hz, 1H), 7.49 (t, J=1.4 Hz, 1H), 7.41 (s, 1H), 6.70 (d, J=5.3 Hz, 1H), 6.68 (s, 1H), 3.64-3.60 (m, 2H), 3.60-3.55 (m, 2H), 3.29 (s, 3H), 3.11 (s, 3H), 2.26 (s, 3H) (ESI+) m/z 364 (M+H)$^+$. Retention time=2.55 mins (method 1).

Example 016

Preparation of (4-Methyl-pyridin-2-yl)-[6-(2-pyridin-2-yl-oxazol-5-yl)-pyridin-2-yl]-amine

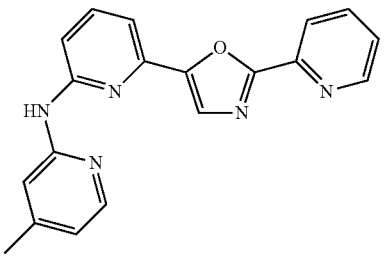 [SMILES: Cc1ccnc(Nc2cccc(-c3cnc(-c4ccccn4)o3)n2)c1]

A mixture of [6-(2-chloro-oxazol-5-yl)-pyridin-2-yl]-(4-methyl-pyridin-2-yl)-amine (44 mg, 0.153 mmol), 2-tri-n-butylstannyl pyridine (68 mg, 0.184 mmol) and Pd(PPh$_3$)$_4$ (18 mg, 0.016 mmol) in toluene (4 ml) was heated to reflux for 18 h and then concentrated in vacuo. The residue was purified by column chromatography on $SiO_2$ eluting with 5% EtOH in DCM to afford the title compound as a pale orange solid (16 mg, 31%). $^1$H NMR (300 MHz, DMSO-$d_6$): δ=9.85 (s, 1H), 8.76 (d, J=5.0 Hz, 1H), 8.21 (d, J=7.8 Hz, 1H), 8.12 (d, J=5.0 Hz, 1H), 8.03 (t, J=7.8 Hz, 1H), 7.94 (s, 1H), 7.91 (s, 1H), 7.80 (t, J=7.8 Hz, 1H), 7.67 (d, J=8.5, 1H), 7.58 (m, 1H), 7.39 (d, J=7.2 Hz, 1H), 6.78 (d, J=5.0 Hz, 1H), 2.38 (s, 3H). (ESI+) m/z 330 (M+H)⁺. Retention time=2.29 mins (method 1).

Example 017

Preparation of [6-(2-iodo-oxazol-5-yl)-pyridin-2-yl]-(4-methyl-pyridin-2-yl)-amine

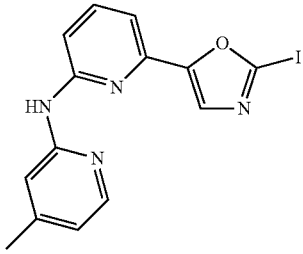 [SMILES: Cc1ccnc(Nc2cccc(-c3cnc(I)o3)n2)c1]

The 2-iodooxazole derivative was prepared as for [6-(2-chloro-oxazol-5-yl)-pyridin-2-yl]-(4-methyl-pyridin-2-yl)-amine above from (4-methyl-pyridin-2-yl)-(6-oxazol-5-yl-pyridin-2-yl)-amine with LiHMDS (1M solution in THF) and diiodoethane in anhydrous THF to give the title compound as a yellow solid (41%) after purification by column chromatography on SiO₂ eluting with 40% EtOAc in cyclohexane. ¹H NMR (300 MHz, DMSO-d₆) δ=9.81 (s, 1H), 8.10 (d, J=5.0 Hz, 1H), 7.84-7.51 (m, 4H), 7.23 (d, J=7.2 Hz, 1H), 6.77 (d, J=4.6 Hz, 1H), 2.33 (s, 3H).

Example 018

Preparation of (4-Methyl-pyridin-2-yl)-[6-(2-phenyl-oxazol-5-yl)-pyridin-2-yl]-amine

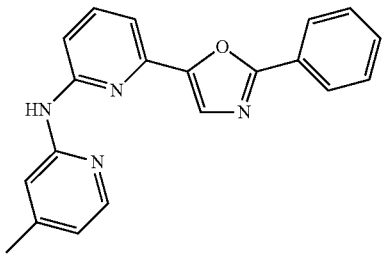 [SMILES: Cc1ccnc(Nc2cccc(-c3cnc(-c4ccccc4)o3)n2)c1]

A solution of [6-(2-iodo-oxazol-5-yl)-pyridin-2-yl]-(4-methyl-pyridin-2-yl)-amine (46 mg, 0.121 mmol), phenylboronic acid (30 mg, 0.246 mmol), K₂CO₃ (37 mg, 0.268 mmol) and Pd(PPh₃)₄ (14 mg, 0.012 mmol) in a mixture of THF (4 ml) and water (2 ml) was stirred at 90° C. for 18 h. The cooled reaction mixture was treated with water and extracted with EtOAc. The combined organics were dried over MgSO₄, filtered and evaporated under reduced pressure before purification by column chromatography on SiO₂ eluting with 30% EtOAc in cyclohexane to afford the title compound as a pale orange solid (30 mg, 75%). ¹H NMR (DMSO-d₆, 300 MHz): δ=9.79 (s, 1H), 8.12 (m, 2H), 8.02 (s, 1H), 7.93 (s, 1H), 7.86 (s, 1H), 7.78 (m, 2H), 7.58 (m, 2H), 7.40 (t, J=7.0 Hz, 1H), 7.33 (t, J=7.0 Hz, 1H), 6.78 (d, J=5.0 Hz, 1H), 2.37 (s, 3H). (ESI+) m/z 329 (M+H)⁺. Retention time=2.84 mins (method 1).

Example 043

Preparation of (4-methyl-pyridin-2-yl)-(3-{2-[2-(3-trifluoromethyl-phenyl)-vinyl]-oxazol-5-yl}-phenyl)-amine

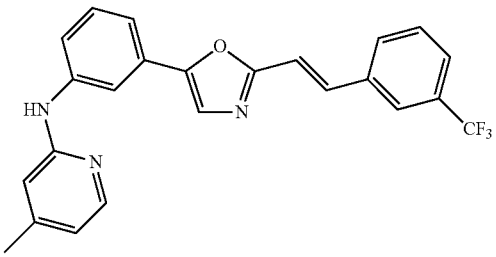 [SMILES: Cc1ccnc(Nc2cccc(-c3cnc(/C=C/c4cccc(C(F)(F)F)c4)o3)c2)c1]

Prepared as for (4-methyl-pyridin-2-yl)-[6-(2-phenyl-oxazol-5-yl)-pyridin-2-yl]-amine above using [3-(2-Iodo-oxazol-5-yl)-phenyl]-(4-methyl-pyridin-2-yl)-amine, trans-2-(3-trifluoromethylphenyl)vinylboronic acid, K₂CO₃ and Pd(PPh₃)₄ in a 2:1 mixture by volume of THF and water to give (4-methyl-pyridin-2-yl)-(3-{2-[2-(3-trifluoromethyl-phenyl)-vinyl]-oxazol-5-yl}-phenyl)-amine as a pale yellow solid (72%). ¹H NMR (400 MHz, DMSO-d₆) δ 9.26-8.94 (m, 1H), 8.15 (s, J=8.6 Hz, 1H), 8.11-8.06 (m, 3H), 7.76-7.63 (m, 5H), 7.43 (d, J=16.5 Hz, 1H), 7.40-7.29 (m, 2H), 6.68 (s, 1H), 6.64 (d, J=5.2 Hz, 1H), 2.25 (s, 3H). (ESI+) m/z 422 (M+H)⁺. Retention time=3.84 mins (method 1).

Example 044

Preparation of {6-[2-(2-Methoxy-pyridin-3-yl)-oxazol-5-yl]-pyridin-2-yl}-(4-methyl-pyridin-2-yl)-amine

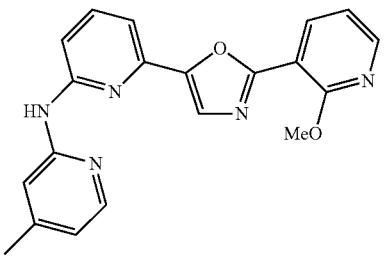 [SMILES: COc1ncccc1-c1ncc(-c2cccc(Nc3cc(C)ccn3)n2)o1]

Prepared as for (4-methyl-pyridin-2-yl)-[6-(2-phenyl-oxazol-5-yl)-pyridin-2-yl]-amine above using [6-(2-iodo-oxazol-5-yl)-pyridin-2-yl]-(4-methyl-pyridin-2-yl)-amine, 2-methoxy-pyridine-3-boronic acid, K₂CO₃ and Pd(PPh₃)₄ in a 2:1 mixture by volume of THF and water to give {6-[2-(2-methoxy-pyridin-3-yl)-oxazol-5-yl]-pyridin-2-yl}-(4-methyl-pyridin-2-yl)-amine as a yellow solid. 1-1 NMR (400 MHz, DMSO-d₆) δ 9.76 (s, 1H), 8.46-8.31 (m, 2H), 8.12 (d, J=5.0 Hz, 1H), 7.87-7.82 (m, 2H), 7.82-7.75 (m, 1H), 7.63 (d, J=8.4 Hz, 1H), 7.34 (d, J=7.3 Hz, 1H), 7.21 (dd, J=7.5, 5.0 Hz, 1H), 6.78 (d, J=5.0 Hz, 1H), 4.04 (s, 3H), 2.33 (s, 3H). (ESI+) m/z 360 (M+H)+. Retention time=2.54 mins (method 1).

Example 045

Preparation of 3-{5-[6-(4-methyl-pyridin-2-ylamino)-pyridin-2-yl]-oxazol-2-yl}-1H-pyridin-2-one

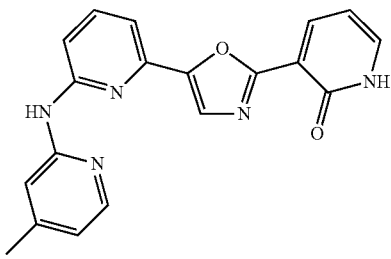 [SMILES: Cc1ccnc(Nc2cccc(-c3cnc(-c4ccc[nH]c4=O)o3)n2)c1]

A solution of {6-[2-(2-methoxy-pyridin-3-yl)-oxazol-5-yl]-pyridin-2-yl}-(4-methyl-pyridin-2-yl)-amine above (236 mg, 0.655 mmol) in EtOH (10 ml) was treated with conc. HCl (1 ml) and heated to 80° C. for 3 h and then 60° C. for 18 h. The cooled mixture was treated with water and the product precipitated as a yellow solid. ¹H NMR (400 MHz, DMSO-d₆) δ 12.23 (s, 1H), 9.78 (s, 1H), 8.29-8.22 (m, 1H), 8.11 (d, J=5.0 Hz, 1H), 7.86 (s, 1H), 7.82-7.73 (m, 2H), 7.69-7.63 (m, 1H), 7.60 (d, J=8.4 Hz, 1H), 7.29 (d, J=7.4 Hz, 1H), 6.77 (d, J=5.0 Hz, 1H), 6.40 (t, J=6.7 Hz, 1H), 2.35 (s, 3H). (ESI+) m/z 346 (M+H)+. Retention time=2.02 mins (method 1).

Example 046

Preparation of 3-{5-[6-(4-methyl-pyridin-2-ylamino)-pyridin-2-yl]-oxazol-2-yl}-1-(2-morpholin-4-yl-ethyl)-1H-pyridin-2-one

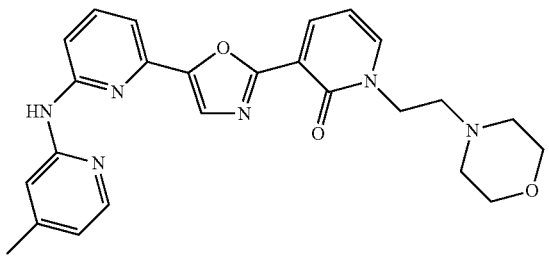 [SMILES: Cc1ccnc(Nc2cccc(-c3cnc(-c4cccn(CCN5CCOCC5)c4=O)o3)n2)c1]

A mixture of 3-{5-[6-(4-methyl-pyridin-2-ylamino)-pyridin-2-yl]-oxazol-2-yl}-1H-pyridin-2-one above (60 mg, 0.17 mmol), 1-(2-chloroethyl)morpholine (36 mg, 0.19 mmol), K₂CO₃ (29 mg, 0.21 mmol), NaI (29 mg, 0.19 mmol) in DMF (6 ml) was heated to 50° C. for 18 h. The mixture was concentrated under vacuum, and the residue treated with water and extracted with EtOAc. The combined organics were washed with water, dried over MgSO₄, filtered and evaporated under reduced pressure before purification by column chromatography on Al₂O₃ (Brockman grade III, 7% H₂O), eluting with 2% EtOH in DCM to afford the title compound as pale yellow solid (27 mg, 35%). ¹H NMR (400 MHz, DMSO-d₆) δ 9.77 (s, 1H), 8.23 (dd, J=7.2, 2.0 Hz, 1H), 8.11 (d, J=5.1 Hz, 1H), 7.95 (dd, J=6.6, 2.0 Hz, 1H), 7.89 (s, 1H), 7.83-7.72 (m, 2H), 7.58 (d, J=8.4 Hz, 1H), 7.29 (d, J=7.4 Hz, 1H), 6.77 (d, J=5.0 Hz, 1H), 6.43 (t, J=6.9 Hz, 1H), 4.13 (t, J=6.2 Hz, 2H), 3.56 (t, J=4.3 Hz, 4H), 2.62 (t, J=6.2 Hz, 2H), 2.48-2.40 (m, 4H), 2.35 (s, 3H). (ESI+) m/z 459 (M+H)+. Retention time=1.63 mins (method 1).

Example 047

Preparation of (4-Methyl-pyridin-2-yl)-[6-(2-phenyl-ethynyl-oxazol-5-yl)-pyridin-2-yl]-amine

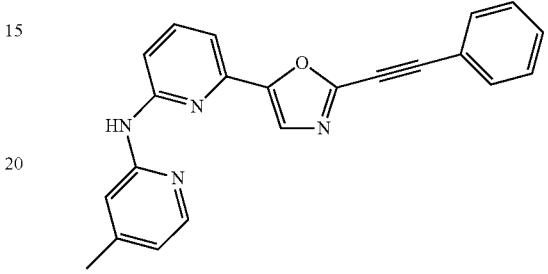

A sealed tube with a teflon screw cap was charged with a mixture of (4-methyl-pyridin-2-yl)-(6-oxazol-5-yl-pyridin-2-yl)-amine (200 mg, 0.793 mmol), bromoethynylbenzene (172 mg, 0.951 mmol) Ni(cod)₂ (11 mg, 0.040 mmol), dppbz (18 mg, 0.040 mmol) and LiOtBu (127 mg, 1.59 mmol) in dry dioxane (5 ml) and heated to 100° C. for 2 h. Further bromoethynylbenzene (172 mg), Ni(cod)₂ (11 mg), dppbz (18 mg) LiOtBu (127 mg, 1.59 mmol) and dry dioxane (2 ml) were added and heating continued for 36 h. The cooled mixture was treated with water and extracted with DCM. The combined organics were dried over MgSO₄, filtered and evaporated under reduced pressure before purification by column chromatography on SiO₂ eluting with 30% EtOAc in cyclohexane to afford the title compound as an off-white solid (35 mg, 13%). ¹H NMR (400 MHz, DMSO-d₆) δ 9.80 (s, 1H), 8.11 (d, J=5.1 Hz, 1H), 7.87 (s, J=26.8 Hz, 1H), 7.80-7.69 (m, 5H), 7.60-7.49 (m, 3H), 7.33 (d, J=7.2 Hz, 1H), 6.77 (d, J=5.1 Hz, 1H), 2.33 (s, 3H). (ESI+) m/z 353 (M+H)+. Retention time=3.24 mins (method 1).

Example 048

Preparation of [6-(2-benzoxazole-2-yl-oxazol-5-yl)-pyridin-2-yl]-(4-methyl-pyridin-2-yl)-amine

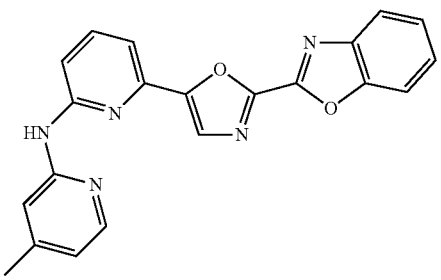 [SMILES: Cc1ccnc(Nc2cccc(-c3cnc(-c4nc5ccccc5o4)o3)n2)c1]

A sealed tube with a teflon screw cap was charged with a mixture of [6-(2-iodo-oxazol-5-yl)-pyridin-2-yl]-(4-methyl-pyridin-2-yl)-amine (100 mg, 0.264 mmol), benzoxazole (31 mg, 0.264 mmol), Pd(PPh$_3$)$_4$ (15 mg, 0.013 mmol) and LiOtBu (42 mg, 0.529 mmol) in dry dioxane (5 ml) and heated to 100° C. for 24 h. The cooled mixture was treated with water and extracted with DCM. The combined organics were dried over MgSO$_4$, filtered and evaporated under reduced pressure before purification by column chromatography on SiO$_2$ eluting with 30% EtOAc in cyclohexane to afford the title compound as a beige solid (12 mg, 12%). $^1$H NMR (400 MHz, DMSO-d$_6$) δ 9.88 (s, 1H), 8.14-8.11 (m, 2H), 7.99-7.88 (m, 3H), 7.83 (t, J=7.9 Hz, 1H), 7.73 (d, J=8.4 Hz, 1H), 7.61-7.51 (m, 2H), 7.46 (d, J=7.3 Hz, 1H), 6.80 (d, J=5.0 Hz, 1H), 2.41 (s, 3H). (ESI+) m/z 370 (M+H)$^+$. Retention time=2.88 mins (method 1).

Example 019

Preparation of 2-Bromo-6-(2-pyridin-3-yl-thiazol-5-yl)-pyridine

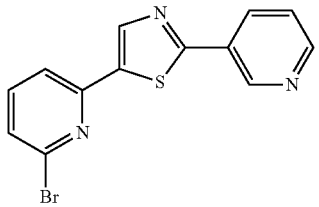 [SMILES: Brc1cccc(-c2cnc(-c3cccnc3)s2)n1]

To a stirred solution of 3-thiazol-2-yl-pyridine (*J. Med. Chem.* 2005, 48, 224) (927 mg, 5.71 mmol) in dry THF (30 mL) cooled at −78° C. under an inert atmosphere was added n-BuLi (2.5M in hexanes) (2.75 mL, 6.87 mmol) dropwise. After stirring at −78° C. for 45 mins, tributyltin chloride (1.86 mL, 6.87 mmol) was added. The mixture was allowed to warm to 0° C. over 90 mins, then treated with water and extracted with ethyl acetate. The combined organic layers were washed with brine, dried over MgSO$_4$, filtered and evaporated under reduced pressure before purification by column chromatography on SiO$_2$ using combiflash Companion®, eluting with cyclohexane/ethyl acetate 100/0 to 82/18 to afford 3-(5-tributylstannanyl-thiazol-2-yl)-pyridine as a colourless oil (955 mg, 37%). $^1$H NMR (DMSO-d$_6$, 300 MHz) δ=9.11 (m, 1H), 8.62 (dd, J=4.77-1.52 Hz, 1H), 8.28 (m, 1H), 7.90 (s, 1H), 7.50 (dd, J=8.0-4.8 Hz, 1H), 1.52 (m, 6H), 1.28 (m, 6H), 1.13 (m, 6H), 0.84 (t, J=7.2 Hz, 9H).

A sealed tube was charged with 2,6-dibromopyridine (269 mg, 1.13 mmol), 3-(5-tributylstannanyl-thiazol-2-yl)-pyridine (511 mg, 1.13 mmol), Pd(PPh$_3$)$_4$ (131 mg, 0.11 mmol), [1,1-Bis(diphenylphosphino)ferrocene]palladium(II) chloride. CH$_2$Cl$_2$ (20 mg, 0.024 mmol) and anhydrous and degassed toluene (5 ml) and heated to 110° C. with stirring for 36 h. The cooled reaction mixture was treated with water and extracted with ethyl acetate. The combined organic layers were washed with brine, dried over MgSO$_4$, filtered and evaporated under reduced pressure before purification by column chromatography on SiO$_2$ using combiflash Companion®, eluting with cyclohexane/ethyl acetate to afford the title compound as a white solid (125 mg, 35%). $^1$H NMR (DMSO-d$_6$, 300 MHz): δ=9.21 (d, J=1.7 Hz, 1H), 8.72 (s, 1H), 8.70 (m, 1H), 8.39 (m, 1H), 8.14 (d, J=7.8 Hz, 1H), 7.88 (dd, J=8.0; 7.8 Hz, 1H), 7.62 (d, J=8.0 Hz, 1H), 7.57 (m, 1H).

Example 020

Preparation of (4-Methyl-pyridin-2-yl)-[6-(2-pyridin-3-yl-thiazol-5-yl)-pyridin-2-yl]-amine

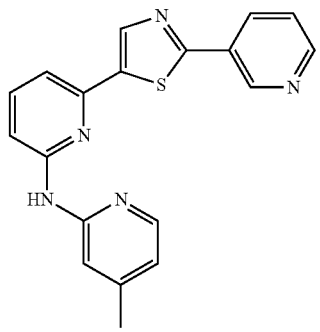 [SMILES: Cc1ccnc(Nc2cccc(-c3cnc(-c4cccnc4)s3)n2)c1]

A sealed tube was charged with 2-bromo-6-(2-pyridin-3-yl-thiazol-5-yl)-pyridine (125 mg, 0.392 mmol), 2-amino-4-methylpyridine (51 mg, 0.471 mmol), Pd(OAc)$_2$ (1.8 mg, 8.01 μmol), BINAP (7.4 mg, 11.9 μmol), Cs$_2$CO$_3$ (255 mg, 0.782 mmol), and anhydrous and degassed toluene (2 ml) and heated to 110° C. with stirring for 48 h. The cooled reaction mixture was treated with water and extracted with ethyl acetate. The combined organic layers were washed with brine, dried over MgSO$_4$, filtered and evaporated under reduced pressure before purification by column chromatography on SiO$_2$ using combiflash Companion®, eluting with cyclohexane/ethyl acetate 100/0 to 0/100. The solid obtained was then triturated in methanol, filtered and dried to afford the title compound as a yellow solid. $^1$H NMR (DMSO-d$_6$, 300 MHz): δ=9.74 (s, 1H), 9.15 (d, J=2.1 Hz, 1H), 8.68 (m, 1H), 8.59 (s, 1H), 8.31 (m, 1H), 8.10 (d, J=5.1 Hz, 1H), 7.93 (s, 1H), 7.72 (dd, J=8.2-7.6 Hz, 1H), 7.66-4.40 (m, 3H), 6.77 (d, J=4.9 Hz, 1H), 2.37 (s, 3H). (APCI+) m/z 346 (M+H)$^+$.

Example 021

Preparation of 2-Bromo-6-(2-[1,3]dioxolan-2-yl-thiazol-5-yl)-pyridine

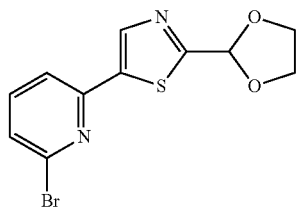 [SMILES: Brc1cccc(-c2cnc(C3OCCO3)s2)n1]

A sealed tube was charged with 2,6-dibromopyridine (525 mg, 2.21 mmol), 2-[1,3]dioxolan-2-yl-5-tributylstannanyl-thiazole (*J. Med. Chem.* 2007, 50, 6303) (990 mg, 2.21 mmol), Pd(PPh$_3$)$_4$ (256 mg, 0.22 mmol), [1,1-Bis(diphenylphosphino)ferrocene]palladium(II) chloride. CH$_2$Cl$_2$ (30 mg, 0.036 mmol) and anhydrous and degassed toluene (8 ml) and heated to 110° C. with stirring for 48 h. The cooled reaction mixture was treated with water and extracted with ethyl acetate. The combined organic layers were washed with brine, dried over MgSO$_4$, filtered and evaporated under reduced pressure before purification by column chromatography on SiO$_2$ using combiflash Companion®, eluting with cyclohexane/ethyl acetate 100/0 to 44/56 to afford the title compound as a white solid (370 mg, 54%). $^1$H NMR (DMSO-d$_6$, 300 MHz): δ=8.55 (s, 1H), 8.06 (dd, J=7.7-0.7 Hz, 1H), 7.85 (dd, J=7.9-7.7 Hz, 1H), 7.61 (dd, J=7.9-0.7 Hz, 1H), 6.08 (s, 1H), 4.15-4.00 (m, 4H).

Example 022

Preparation of [6-(2-[1,3]Dioxolan-2-yl-thiazol-5-yl)-pyridin-2-yl]-(4

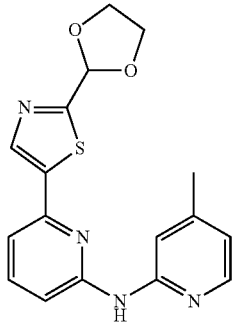 [SMILES: Cc1ccnc(Nc2cccc(-c3cnc(C4OCCO4)s3)n2)c1]

A sealed tube was charged with 2-bromo-6-(2-[1,3]dioxolan-2-yl-thiazol-5-yl)-pyridine (350 mg, 1.11 mmol), 2-amino-4-methylpyridine (145 mg, 1.34 mmol), Pd(OAc)$_2$ (5 mg, 22.2 μmol), BINAP (21 mg, 33.7 μmol), Cs$_2$CO$_3$ (728 mg, 2.23 mmol), and anhydrous and degassed toluene (3 ml) and heated to 110° C. with stirring for 24 h. The cooled reaction mixture was treated with water and extracted with ethyl acetate. The combined organic layers were washed with brine, dried over MgSO$_4$, filtered and evaporated under reduced pressure before purification by column chromatography on SiO$_2$ using combiflash Companion®, eluting with cyclohexane/ethyl acetate 100/0 to 20/80 to afford the title compound as a white solid (276 mg, 73%). $^1$H NMR (DMSO-d$_6$, 300 MHz): δ=9.72 (s, 1H), 8.44 (s, 1H), 8.11 (d, J=4.9 Hz, 1H), 7.92 (s, 1H), 7.72 (dd, J=8.2-7.6 Hz, 1H), 7.46 (dd, J=8.9-7.6 Hz, 1H), 6.78 (d, J=4.9 Hz, 1H), 6.08 (s, 1H), 4.20-4.00 (m, 4H), 2.34 (s, 3H).

Example 023

Preparation of 5-[6-(4-Methyl-pyridin-2-ylamino)-pyridin-2-yl]-thiazole-2-carbaldehyde

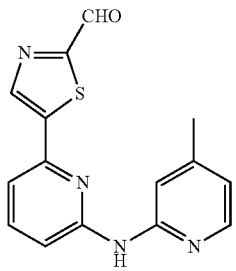 [SMILES: Cc1ccnc(Nc2cccc(-c3cnc(C=O)s3)n2)c1]

To a stirred solution of [6-(2-[1,3]dioxolan-2-yl-thiazol-5-yl)-pyridin-2-yl]-(4-methyl-pyridin-2-yl)-amine (270 mg, 0.793 mmol) in THF (8 mL) was added 2N HCl (2 mL). The mixture was heated at 60° C. overnight. After cooling, saturated NaHCO$_3$ was added to basic pH then the aqueous phase was extracted with ethyl acetate. The combined organic layers were washed with brine, dried over MgSO$_4$, filtered and evaporated under reduced pressure to afford the title compound as a yellow solid (220 mg, 94%). $^1$H NMR (DMSO-d$_6$, 300 MHz): δ=9.94 (s, 1H), 9.83 (s, 1H), 8.87 (s, 1H), 8.12 (d, J=4.9 Hz, 1H), 7.90 (s, 1H), 7.78 (m, 1H), 7.64 (d, J=7.6 Hz, 1H), 7.53 (d, J=8.4 Hz, 1H), 6.80 (d, J=5.1 Hz, 1H), 2.35 (s, 3H).

Example 024

Preparation of E-(4-Methyl-pyridin-2-yl)-[6-(2-styryl-thiazol-5-yl)-pyridin-2-yl]-amine

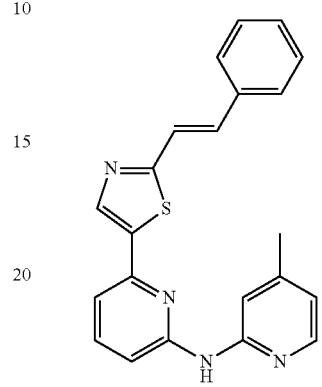

To a suspension of benzyltriphenylphosphonium bromide (176 mg, 0.406 mmol) in dry THF cooled at 0° C. under inert atmosphere was added potassium tot-butoxide (1.0M in THF) (675 μL, 675 μmol). The mixture was stirred at 0° C. for 30 mins, then 5-[6-(4-methyl-pyridin-2-ylamino)-pyridin-2-yl]-thiazole-2-carbaldehyde was added in one portion. After stirring at room temperature for 3 hours, the reaction mixture was treated with water and extracted with ethyl acetate. The combined organic layers were washed with brine, dried over MgSO$_4$, filtered and evaporated under reduced pressure before purification by column chromatography on SiO$_2$ using combiflash Companion®, eluting with cyclohexane/ethyl acetate. The E-isomer was then further purified by preparative chromatography on silica plate, eluting with 5% methanol in dichloromethane to afford the title compound as a yellow solid. $^1$H NMR (Acetone-d$_6$, 300 MHz): δ=8.41 (s, 1H), 8.16 (d, J=5.1 Hz, 1H), 8.00 (s, 1H), 7.80-7.70 (m, 3H), 7.65-7.55 (m, 2H), 7.53-7.36 (m, 4H), 7.50 (s, 1H), 6.84 (d, J=5.1 Hz, 1H), 2.47 (s, 3H). (APCI+) m/z 371 (M+H)$^+$.

Example 049

Preparation of 6-(2-(4-methoxyphenyl)thiazol-5-yl)-N-(4-methylpyridin-2-yl)pyridin-2-amine

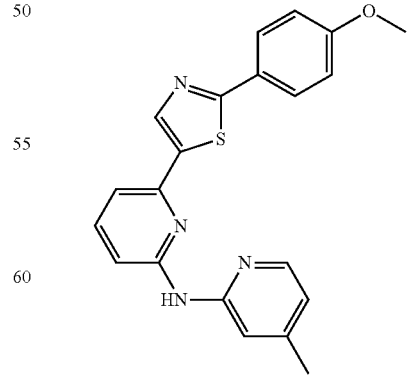

Palladium triphenylphosphine (0.35 mg, 0.29 mmol) was added to a degassed solution of 2-bromothiazole (0.54 ml, 6.00 mmol), (4-methoxyphenyl)boronic acid (1.00 g, 6.60 mmol) and K$_2$CO$_3$ (2.50 g, 18.08 mmol) in 20 ml of dioxane in a sealed tube The reaction mixture was heated at 120° C. under N$_2$ for 16 hours. The reaction mixture was cooled down and filtered over Celite®. The cake was washed with DCM/EtOH and the filtrate was concentrated. The 2-(4-methoxyphenyl)thiazole was purified by dry flash chromatography eluting with EtOAc/Cyclohexane 10/90 (0.96 g, 83%). $^1$H NMR (300 MHz, DMSO-d$_6$) δ 7.97 (d, J=7.9 Hz, 2H), 7.93 (d, J=3.3, 1H), 7.77 (d, J=3.3, 1H), 7.13 (d, J=8.1 Hz, 2H), 3.90 (s, 3H).

By following essentially the same procedure in preparative example 019 and starting with 2-(4-methoxyphenyl)thiazole (960 mg, 5.01 mmol), the 2-(4-methoxyphenyl)-5-(tributylstannyl)thiazole was obtained and purified by dry flash chromatography over SiO$_2$ eluting with EtOAc/Cyclohexane 10/90 (1.76 g, 80%). $^1$H NMR (300 MHz, DMSO-d$_6$) δ 7.91 (d, J=8.3 Hz, 2H), 7.79 (s, 1H), 7.07 (d, J=8.5 Hz, 2H), 3.84 (s, 3H), 1.63-1.51 (m, 6H), 1.40-1.25 (m, 6H), 1.21-1.12 (m, 6H), 0.89 (t, J=7.3 Hz, 9H).

A sealed tube was charged with 2,6-dibromopyridine (474 mg, 2.00 mmol), 2-(4-methoxyphenyl)-5-(tributylstannyl)thiazole (920 mg, 2.00 mmol), Pd(PPh$_3$)$_4$ (231 mg, 0.20 mmol), and anhydrous and degazed toluene (9 ml) and heated to 120° C. with stirring for 24 hours. The cooled reaction mixture was treated with water and extracted with ethyl acetate. The combined organic layers were dried over MgSO$_4$, filtered and evaporated under reduced pressure before purification by dry flash chromatography over SiO$_2$ eluting with EtOAc/cyclohexane 20/80 to give 5-(6-bromopyridin-2-yl)-2-(4-methoxyphenyl)thiazole (410 mg, 59%). $^1$H NMR (300 MHz, DMSO-d$_6$) δ 8.55 (s, 1H), 8.06 (d, J=7.2 Hz, 1H), 7.96 (d, J=8.3 Hz, 2H), 7.82 (t, J=7.8 Hz, 1H), 7.57 (d, J=7.3 Hz, 1H), 7.07 (d, J=8.5 Hz, 2H), 3.83 (s, 3H).

By following essentially the same procedure in example 020 and starting with 5-(6-bromopyridin-2-yl)-2-(4-methoxyphenyl)thiazole (130 mg, 0.37 mmol), the 6-(2-(4-methoxyphenythiazol-5-yl)-N-(4-methylpyridin-2-yl)pyridin-2-amine was obtained and purified by thin layer chromatography over SiO$_2$ eluting with EtOAc/MeOH (3%)—NEt$_3$ (0.5%) (111 mg, 80%). $^1$H NMR (300 MHz, DMSO-d$_6$) δ 9.72 (s, 1H), 8.48 (s, 1H), 8.12 (d, J=5.1 Hz, 1H), 7.97 (s, 1H), 7.94 (d, J=8.8 Hz, 2H), 7.72 (t, J=7.9 Hz, 1H), 7.48 (d, J=7.4 Hz, 1H), 7.44 (d, J=8.3 Hz, 1H), 7.11 (d, J=8.8 Hz, 2H), 6.80 (d, J=5.2 Hz, 1H), 3.85 (s, 3H), 2.39 (s, 3H). (APCI+) m/z 375 (M+H)$^+$.

Example 050

Preparation of N-(3-(2-(4-methoxyphenythiazol-5-yl)phenyl)-4-methylpyridin-2-amine

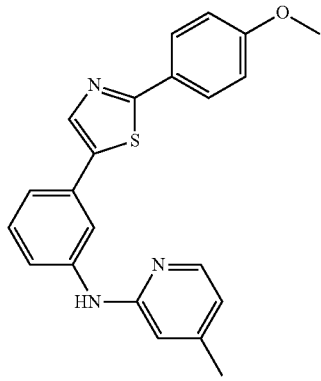 [SMILES: COc1ccc(-c2ncc(-c3cccc(Nc4cc(C)ccn4)c3)s2)cc1]

By following essentially the same procedure in example 019 and starting with 1,3-dibromobenzene (0.250 ml, 2.00 mmol) and the 2-(4-methoxyphenyl)-5-(tributylstannyl)thiazole (880 mg, 2.00 mmol), the 5-(3-bromophenyl)-2-(4-methoxyphenyl)thiazole was obtained and purified by dry flash chromatography over SiO$_2$ eluting with EtOAc/Cyclohexane 20/80 (406 mg, 58%). $^1$H NMR (300 MHz, DMSO-d$_6$) δ 8.36 (s, 1H), 7.96 (t, J=1.8 Hz, 1H), 7.92 (d, J=8.9 Hz, 2H), 7.72-7.67 (m, 1H), 7.56 (dd, J=4.9, 4.0 Hz, 1H), 7.42 (t, J=7.9 Hz, 2H), 7.10 (d, J=8.9 Hz, 2H), 3.84 (s, 3H).

By following essentially the same procedure in example 020 and starting with 5-(3-bromophenyl)-2-(4-methoxyphenyl)thiazole (130 mg, 0.37 mmol), the N-(3-(2-(4-methoxyphenypthiazol-5-yl)phenyl)-4-methylpyridin-2-amine was obtained and purified by thin layer chromatography over SiO$_2$ eluting with EtOAc/cyclohexane 50/50 (26 mg, 18%). $^1$H NMR (300 MHz, DMSO) δ 9.10 (br s, 1H), 8.15 (s, 1H), 8.07 (d, J=5.1 Hz, 1H), 8.01 (br s, 1H), 7.92 (d, J=8.6 Hz, 2H), 7.71 (d, J=7.5 Hz, 1H), 7.33 (t, J=7.8 Hz, 1H), 7.22 (d, J=6.9 Hz, 1H), 7.08 (d, J=8.7 Hz, 2H), 6.70-6.61 (m, 2H), 3.83 (s, 3H), 2.25 (s, 3H). (APCI+) m/z 374 (M+H)$^+$.

Example 051

Preparation of 4-(5-(6-(4-methylpyridin-2-ylamino)pyridin-2-yl)thiazol-2-yl)benzonitrile

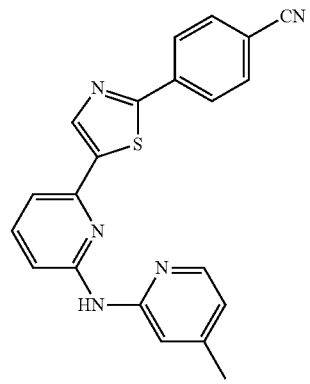 [SMILES: Cc1ccnc(Nc2cccc(-c3cnc(-c4ccc(C#N)cc4)s3)n2)c1]

Palladium triphenylphosphine (0.35 mg, 0.29 mmol) was added to a degassed solution of 2-bromothiazole (0.63 ml, 7.00 mmol) and (4-cyanophenyl)boronic acid (1.00 g, 6.80 mmol) in 75 ml of CH$_3$CN in a sealed tube. Aqueous Na$_2$CO$_3$ (0.4 M, 35 ml) was added and the reaction mixture was heated at 90° C. under N$_2$ for 24 hours. The reaction mixture was cooled and the aqueous layer was separated and extracted once with EtOAc (100 ml). The combined organic phases were dried over MgSO$_4$. After filtration and evaporation, 4-(thiazol-2-yl)benzonitrile was purified by dry flash chromatography eluting with EtOAc/Cyclohexane 20/80 (1.13 g, 89%). $^1$H NMR (300 MHz, DMSO-d$_6$) δ 8.14 (d, J=8.3 Hz, 2H), 8.03 (d, J=3.2 Hz, 1H), 8.00-7.93 (m, 3H).

By following essentially the same procedure in preparative example 019 and starting with 4-(thiazol-2-yl)benzonitrile (600 mg, 3.22 mmol), the 4-(5-(tributylstannyl)thiazol-2-yl)benzonitrile was purified by dry flash chromatography over SiO$_2$ eluting with EtOAc/Cyclohexane 10/90 (1.10 g, 79%). $^1$H NMR (300 MHz, DMSO-d$_6$) δ 8.14 (d, J=8.3 Hz, 2H), 7.99-7.92 (m, 3H), 1.62-1.47 (m, 6H), 1.38-1.23 (m, 6H), 1.21-1.14 (m, 6H), 0.87 (t, J=7.3 Hz, 9H).

By following essentially the same procedure in preparative example 020 and starting with 6-bromo-N-(4-methylpyridin-2-yl)pyridin-2-amine (100 mg 0.38 mmol) and 4-(5-(tributylstannyl)thiazol-2-yl)benzonitrile (328 mg, 0.69 mmol), the 4-(5-(6-(4-methylpyridin-2-ylamino)pyridin-2-yl)thiazol-2-yl)benzonitrile was obtained and purified by dry flash chromatography over SiO$_2$ eluting with EtOAc/Cyclohexane 50/50-MeOH (5%) and by trituration with Et$_2$O (51 mg, 37%). $^1$H NMR (300 MHz, DMSO-d$_6$) δ 9.77 (br s, 1H), 8.65 (s, 1H), 8.20-8.10 (m, 3H), 8.00 (d, J=8.4 Hz, 2H), 7.93 (br s, 1H), 7.75 (t, J=7.9 Hz, 1H), 7.55 (d, J=7.4 Hz, 1H), 7.50 (d, J=8.3 Hz, 1H), 6.80 (d, J=5.1 Hz, 1H), 2.39 (s, 3H). (APCI+) m/z 370 (M+H)$^+$.

Example 052

Preparation of 4-(5-(6-(4-methylpyridin-2-ylamino)pyridin-2-yl)thiazol-2-yl)benzamide

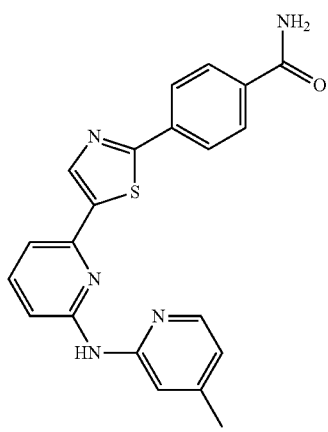 [SMILES: Cc1ccnc(Nc2cccc(-c3cnc(-c4ccc(C(N)=O)cc4)s3)n2)c1]

4-(5-(6-(4-methylpyridin-2-ylamino)pyridin-2-yl)thiazol-2-yl)benzonitrile (Example 51, 40 mg, 0.11 mmol) was suspended in EtOH (8 ml). Aqueous ammonia (28-30%, 4 ml) was added followed by H$_2$O$_2$ (35%, 1 ml). The reaction mixture was stirred at 40° C. for 2.5 days. Aqueous ammonia (2 ml) and H$_2$O$_2$ (0.250 ml) were added and the reaction mixture was stirred a further 24 hours at 40° C. The reaction was partitioned between H$_2$O (30 ml) and EtOAc (70 ml). After separation, the aqueous phase was extracted again with EtOAc (70 ml). After evaporation, and purification of the crude product by dry flash chromatography over SiO$_2$ eluting with EtOAc/MeOH (5%-10%)/NEt$_3$ (0.5%), 4-(5-(6-(4-methylpyridin-2-ylamino)pyridin-2-yl)thiazol-2-yl)benzamide was obtained as a yellow solid (46 mg, 74%). $^1$H NMR (300 MHz, DMSO-d$_6$) δ 9.72 (br s, 1H), 8.59 (br s, 1H), 8.20-7.98 (m, 6H), 7.95 (d, J=8.6 Hz, 1H), 7.78-7.70 (m, 1H), 7.66 (d, J=8.8 Hz, 1H), 7.57-7.45 (m, 3H), 2.25 (s, 3H). (APCI+) m/z 388 (M+H)$^+$.

Example 053

Preparation of 6-(2-(4-methoxyphenyl)thiazol-5-yl)-N-(5-methylpyridin-2-yl)pyridin-2-amine

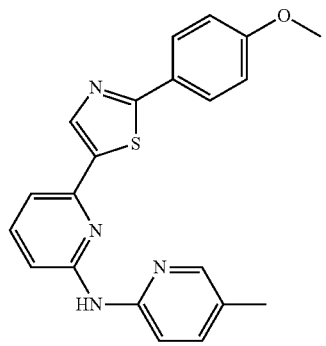 [SMILES: COc1ccc(-c2ncc(-c3cccc(Nc4ccc(C)cn4)n3)s2)cc1]

By following essentially the same procedure in preparative example 050 and starting with 5-(6-bromopyridin-2-yl)-2-(4-methoxyphenyl)thiazole (100 mg, 0.29 mmol), the 6-(2-(4-methoxyphenyl)thiazol-5-yl)-N-(5-methylpyridin-2-yl)pyridin-2-amine was obtained and purified by trituration in Et$_2$O/DCM (66 mg, 61%). $^1$H NMR (300 MHz, DMSO-d$_6$) δ 9.67 (s, 1H), 8.09 (d, J=2.3 Hz, 1H), 7.98-7.91 (m, 3H), 7.71 (t, J=7.9 Hz, 1H), 7.63 (dd, J=8.5, 2.4 Hz, 1H), 7.45 (d, J=7.9 Hz, 1H), 7.09 (d, J=8.3 Hz, 1H), 3.85 (s, 3H), 2.25 (s, 3H). (APCI+) m/z 374 (M+H)$^+$. Retention time=2.66 mins (method 2).

Example 054

Preparation of 3-(5-(6-(4-methylpyrimidin-2-ylamino)pyridin-2-yl)thiazol-2-yl)benzonitrile

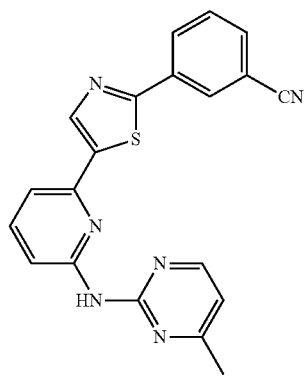 [SMILES: Cc1ccnc(Nc2cccc(-c3cnc(-c4cccc(C#N)c4)s3)n2)n1]

A solution of 2-amino-4-methylpyrimidine (980 mg, 8.86 mmol) in THF (10 ml) was added dropwise to a cooled suspension of NaH (60% on oil, 1 g, 25.32 mmol) in THF (15 ml) under inert atmosphere. The reaction mixture was heated at 55° C. for 2 hours. The reaction was cooled down to 0° C. and a solution of 2,6-dibromopyridine (2 g, 8.44 mmol) in THF (20 ml) was added. The reaction mixture was heated at 80° C. for 5 hours. The reaction was cooled down to 0° C. and hydrolysed carefully with water (50 ml). After extraction with EtOAc (2×100 ml), the combined extractions were dried over MgSO$_4$. After filtration and evaporation, N-(6-bromopyridin- 2-yl)-4-methylpyrimidin-2-amine was obtained and purified by dry flash chromatography over SiO$_2$ eluting with DCM/MeOH(1%)/NEt$_3$ (0.5%) (0.846 g, 38%). $^1$H NMR (300 MHz, DMSO-d$_6$) δ 10.12 (br s, 1H), 8.44 (d, J=5.0 Hz, 1H), 8.36 (d, J=8.3 Hz, 1H), 7.69 (t, J=8.0 Hz, 1H), 7.18 (dd, J=7.6, 0.6 Hz, 1H), 6.91 (d, J=5.0 Hz, 1H), 2.42 (s, 3H).

By following essentially the same procedure in preparative example 019 and starting with N-(6-bromopyridin-2-yl)-4-methylpyrimidin-2-amine (215 mg 0.81 mmol) and 3-(5-(tributylstannyl)thiazol-2-yl)benzonitrile (656 mg, 1.38 mmol), the 3-(5-(6-(4-methylpyrimidin-2-ylamino)pyridin-2-yl)thiazol-2-yl)benzonitrile was obtained and purified by dry flash chromatography over SiO$_2$ eluting with DCM/MeOH (5%)/NEt$_3$ (0.5%), by precipitation in DCM/MeOH and by trituration with Et$_2$O (119 mg, 39%). $^1$H NMR (300 MHz, DMSO-d$_6$) δ 9.60 (br s, 1H), 8.62 (s, 1H), 8.43 (d, J=5.0 Hz, 1H), 8.38 (d, J=2.3 Hz, 1H), 8.31-8.23 (m, 2H), 8.01-7.95 (m, 1H), 7.86 (t, J=8.0 Hz, 1H), 7.75 (t, J=7.9 Hz, 1H), 7.64 (d, J=7.5 Hz, 1H), 6.89 (d, J=5.0 Hz, 1H), 2.42 (s, 3H). (APCI+) m/z 371 (M+H)$^+$.

By repeating the methods described above using the appropriate starting materials and conditions, the following additional analogues in Table 1 were prepared and characterized.

TABLE 1

| Ex # | Chemical structure | Name | $^1$H NMR/LCMS |
|---|---|---|---|
| 055 | 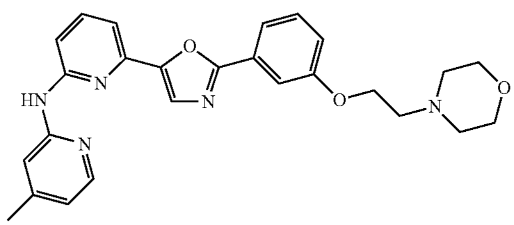 [SMILES: Cc1ccnc(Nc2cccc(-c3cnc(-c4cccc(OCCN5CCOCC5)c4)o3)n2)c1] | (4-Methyl-pyridin-2-yl)-[6-{2-[3-(2-morpholin-4-yl-ethoxy)-phenyl]-oxazol-5-y}-pyridin-2-yl]-amine | (400 MHz, DMSO-d$_6$) δ 9.79 (s, 1H), 8.12 (d, J = 5.0 Hz, 1H), 7.91 (s, 1H), 7.85 (s, 1H), 7.77 (t, J = 7.9 Hz, 1H), 7.70 (d, J = 7.7 Hz, 1H), 7.62 (s, 1H), 7.58 (d, J = 8.4 Hz, 1H), 7.49 (t, J = 7.9 Hz, 1H), 7.43 (d, J = 7.4 Hz, 1H), 7.17 (d, J = 8.3 Hz, 1H), 6.78 (d, J = 4.8 Hz, 1H), 4.20 (t, J = 5.5 Hz, 2H), 3.69-3.44 (m, 4H), 2.73 (t, J = 5.5 Hz, 2H), 2.61-2.42 (m, 4H), 2.36 (s, 3H). (ESI+) m/z 458 (M + H)$^+$ Retention time = 1.94 mins (method 1) |
| 056 | 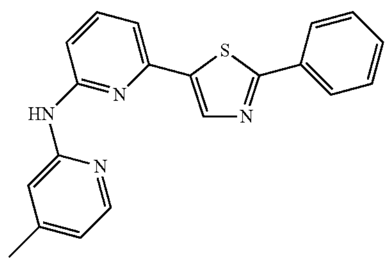 | (4-Methyl-pyridin-2-yl)-[6-(2-phenyl-thiazol-5-yl)-pyridin-2-yl]-amine | (300 MHz, DMSO-d$_6$) δ 8.27 (s, 1H), 8.11 (d, J = 5.2 Hz, 1H), 8.00 (dd, J = 7.3, 2.0 Hz, 2H), 7.82 (s, 1H), 7.64 (t, J = 7.9 Hz, 1H), 7.53-7.41 (m, 3H), 7.34-7.23 (m, 2H), 6.77 (d, J = 5.2 Hz, 1H), 2.44 (s, 3H). (APCI+) m/z 423 (M + H)$^+$ Retention time = 2.70 mins (method 2) |
| 057 | 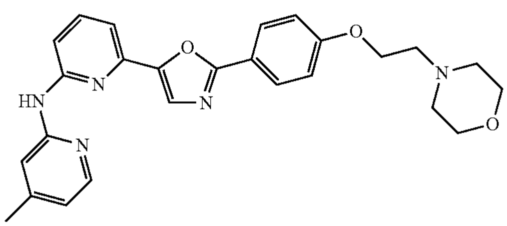 [SMILES: Cc1ccnc(Nc2cccc(-c3cnc(-c4ccc(OCCN5CCOCC5)cc4)o3)n2)c1] | (4-Methyl-pyridin-2-yl)-(6-{2-[4-(2-morpholin-4-yl-ethoxy)-phenyl]-oxazol-5-yl}-pyridin-2-yl)-amine | (400 MHz, DMSO-d$_6$) δ 9.77 (s, 1H), 8.11 (d, J = 5.1 Hz, 1H), 8.04 (d, J = 8.2 Hz, 2H), 7.91 (s, 1H), 7.84-7.65 (m, 2H), 7.57 (d, J = 8.4 Hz, 1H), 7.37 (d, J = 7.4 Hz, 1H), 7.14 (d, J = 8.3 Hz, 2H), 6.78 (d, J = 5.0 Hz, 1H), 4.18 (t, J = 5.5 Hz, 2H), 3.65-3.49 (m, 4H), 2.81-2.60 (m, 2H), 2.50-2.44 (m, 4H), 2.35 (s, 3H). (ESI+) m/z 458 (M + H)$^+$ Retention time = 1.88 mins (method 1) |
| 058 | 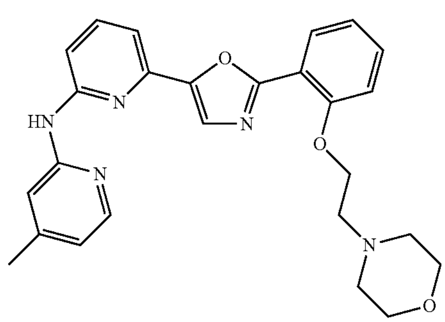 [SMILES: Cc1ccnc(Nc2cccc(-c3cnc(-c4ccccc4OCCN4CCOCC4)o3)n2)c1] | (4-Methyl-pyridin-2-yl)-(6-{2-[2-(2-morpholin-4-yl-ethoxy)-phenyl]-oxazol-5-yl}-pyridin-2-yl)-amine | (400 MHz, DMSO-d$_6$) δ 9.78 (s, 1H), 8.11 (d, J = 5.1 Hz, 1H), 7.97 (dd, J = 7.7, 1.4 Hz, 1H), 7.86 (s, 1H), 7.82-7.74 (m, 2H), 7.61 (d, J = 8.4 Hz, 1H), 7.53 (dd, J = 11.4, 4.3 Hz, 1H), 7.29 (dd, J = 12.6, 7.9 Hz, 2H), 7.12 (t, J = 7.5 Hz, 1H), 6.77 (d, J = 4.9 Hz, 1H), 4.26 (t, J = 5.5 Hz, 2H), 3.50 (t, J = 4.4 Hz, 4H), 2.85-2.74 (m, 2H), 2.49-2.44 (m, 3H), 2.33 (s, 3H). (ESI+) m/z 458 (M + H)$^+$ Retention time = 1.94 mins (method 1) |

TABLE 1-continued

| Ex # | Chemical structure | Name | ¹H NMR/LCMS |
|---|---|---|---|
| 059 | 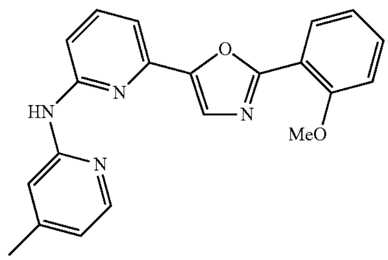 [SMILES: COc1ccccc1-c1ncc(-c2cccc(Nc3cc(C)ccn3)n2)o1] | {6-[2-(2-Methoxy-phenyl)-oxazol-5-yl]-pyridin-2-yl}-(4-methyl-pyridin-2-yl)-amine | (400 MHz, DMSO-$d_6$) δ 9.78 (s, 1H), 8.12 (d, J = 5.1 Hz, 1H), 7.98 (dd, J = 7.7, 1.7 Hz, 1H), 7.85 (s, 1H), 7.83-7.74 (m, 2H), 7.62 (d, J = 8.4 Hz, 1H), 7.59-7.52 (m, 1H), 7.29 (dd, J = 19.3, 7.8 Hz, 2H), 7.13 (t, J = 7.6 Hz, 1H), 6.77 (d, J = 4.9 Hz, 1H), 3.94 (s, 3H), 2.33 (s, 3H). (ESI+) m/z 359 (M + H)⁺ Retention time = 2.73 mins (method 1) |
| 060 | 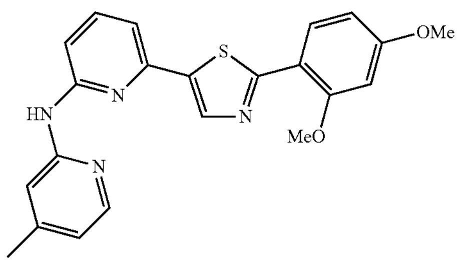 [SMILES: COc1ccc(-c2ncc(-c3cccc(Nc4cc(C)ccn4)n3)s2)c(OC)c1] | {6-[2-(2,4-Dimethoxy-phenyl)-thiazol-5-yl]-pyridin-2-yl}-(4-methyl-pyridin-2-yl)-amine | (300 MHz, DMSO-$d_6$) δ 9.70 (s, 1H), 8.47 (s, 1H), 8.25 (d, J = 8.8 Hz, 1H), 8.12 (d, J = 5.1 Hz, 1H), 8.07 (s, 1H), 7.76-7.64 (m, 1H), 7.46 (d, J = 7.5 Hz, 1H), 7.36 (d, J = 8.2 Hz, 1H), 6.91-6.69 (m, 3H), 4.05 (s, 3H), 3.86 (s, 3H), 2.41 (s, 3H). (APCI+) m/z 405 (M + H)⁺ Retention time = 2.58 mins (method 2) |
| 061 | 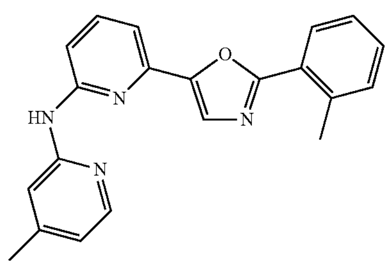 [SMILES: Cc1ccnc(Nc2cccc(-c3cnc(-c4ccccc4C)o3)n2)c1] | (4-Methyl-pyridin-2-yl)-[6-(2-o-tolyl-oxazol-5-yl)-pyridin-2-yl]-amine | (400 MHz, DMSO-$d_6$) δ 9.76 (s, 1H), 8.12 (d, J = 5.2 Hz, 2H), 7.93 (s, 1H), 7.88 (s, 1H), 7.78 (t, J = 8.0 Hz, 1H), 7.57 (d, J = 8.4 Hz, 1H), 7.49-7.35 (m, 4H), 6.78 (d, J = 5.0 Hz, 1H), 2.73 (s, 3H), 2.35 (s, 3H). (ESI+) m/z 343 (M + H)⁺ Retention time = 3.12 mins (method 1) |
| 062 | 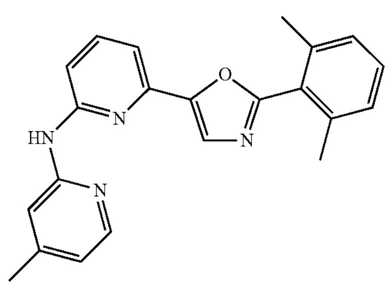 [SMILES: Cc1ccnc(Nc2cccc(-c3cnc(-c4c(C)cccc4C)o3)n2)c1] | {6-[2-(2,6-Dimethyl-phenyl)-oxazol-5-yl]-pyridin-2-yl}-(4-methyl-pyridin-2-yl)-amine | (400 MHz, DMSO) δ 9.78 (s, 1H), 8.10 (d, J = 5.1 Hz, 1H), 7.88 (s, 1H), 7.84 (s, 1H), 7.75 (t, J = 7.8 Hz, 1H), 7.60 (d, J = 8.4 Hz, 1H), 7.37 (t, J = 7.7 Hz, 1H), 7.29 (d, J = 7.4 Hz, 1H), 7.23 (d, J = 7.6 Hz, 2H), 6.76 (d, J = 5.3 Hz, 1H), 2.28 (s, 9H). (ESI+) m/z 357 (M + H)⁺ Retention time = 3.18 mins (method 1) |
| 063 | 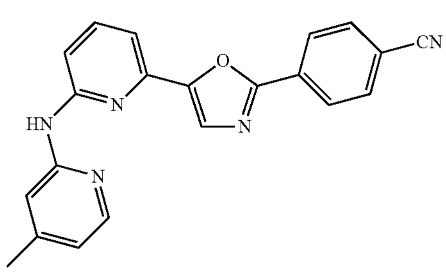 | 4-{5-[6-(4-Methyl-pyridin-2-ylamino)-pyridin-2-yl]-oxazol-2-yl}-benzonitrile | (400 MHz, DMSO) δ 9.77 (s, 1H), 8.26 (d, J = 8.4 Hz, 2H), 8.11 (d, J = 5.1 Hz, 1H), 8.06 (d, J = 8.4 Hz, 2H), 7.92 (s, 1H), 7.89 (s, 1H), 7.79 (t, J = 7.9 Hz, 1H), 7.61 (d, J = 8.3 Hz, 1H), 7.45 (d, J = 7.4 Hz, 1H), 6.78 (d, J = 4.9 Hz, 1H), 2.35 (s, 3H). (ESI+) m/z 354 (M + H)⁺ Retention time = 2.82 mins (method 1) |
| 064 | 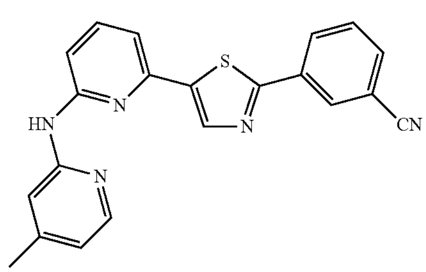 [SMILES: Cc1ccnc(Nc2cccc(-c3cnc(-c4cccc(C#N)c4)s3)n2)c1] | 3-{5-[6-(4-Methyl-pyridin-2-ylamino)-pyridin-2-yl]-thiazol-2-yl}-benzonitrile | (300 MHz, DMSO-$d_6$) δ 9.76 (br s, 1H), 8.63 (br s, 1H), 8.39 (br s, 1H), 8.29 (d, J = 8.0 Hz, 1H), 8.13 (d, J = 5.1 Hz, 1H), 7.99 (d, J = 7.7 Hz, 1H), 7.92 (s, 1H), 7.76 (td, J = 7.8, 3.3 Hz, 2H), 7.54 (d, J = 7.4 Hz, 1H), 7.50 (d, J = 8.3 Hz, 1H), 6.80 (d, J = 5.1 Hz, 1H), 2.40 (s, 3H). (APCI+) m/z 370 (M + H)⁺ Retention time = 2.53 mins (method 2) |

TABLE 1-continued

| Ex # | Chemical structure | Name | ¹H NMR/LCMS |
|---|---|---|---|
| 065 | 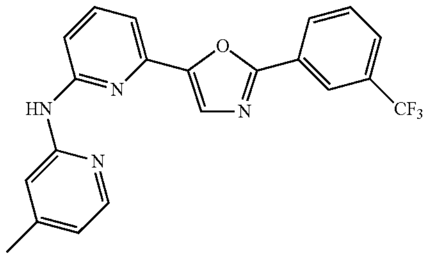 | (4-Methyl-pyridin-2-yl)-{6-[2-(3-trifluoromethyl-phenyl)-oxazol-5-yl]-pyridin-2-yl}-amine | (400 MHz, DMSO-$d_6$) δ 9.77 (s, 1H), 8.41 (d, J = 7.8 Hz, 1H), 8.38-8.33 (m, 1H), 8.12 (d, J = 5.1 Hz, 1H), 7.99-7.75 (m, 5H), 7.61 (d, J = 8.3 Hz, 1H), 7.48 (d, J = 7.4 Hz, 1H), 6.79 (d, J = 4.9 Hz, 1H), 2.35 (s, 3H). (ESI+) m/z 397 (M + H)$^+$ Retention time = 3.44 mins (method 1) |
| 066 | 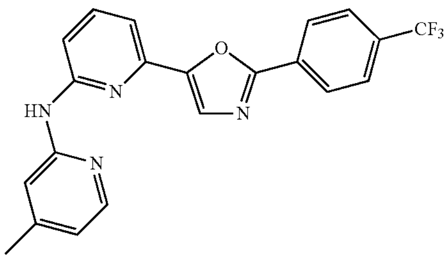 [SMILES: Cc1ccnc(Nc2cccc(-c3cnc(-c4ccc(C(F)(F)F)cc4)o3)n2)c1] | (4-Methyl-pyridin-2-yl)-{6-[2-(4-trifluoromethyl-phenyl)-oxazol-5-yl]-pyridin-2-yl}-amine | (400 MHz, DMSO-$d_6$) δ 9.78 (s, 1H), 8.32 (d, J = 8.1 Hz, 2H), 8.12 (d, J = 5.0 Hz, 1H), 8.01-7.88 (m, 4H), 7.80 (t, J = 7.9 Hz, 1H), 7.62 (d, J = 8.4 Hz, 1H), 7.44 (d, J = 7.4 Hz, 1H), 6.78 (d, J = 4.9 Hz, 1H), 2.36 (s, 3H). (ESI+) m/z 397 (M + H)$^+$ Retention time = 3.41 mins (method 1) |
| 067 | 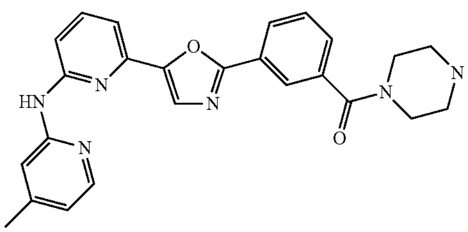 | (4-Methyl-piperazin-1-yl)-(3-{5-[6-(4-methyl-pyridin-2-ylamino)-pyridin-2-yl]-oxazol-2-yl}-phenyl)-methanone | (400 MHz, DMSO-$d_6$) δ 9.80-9.73 (m, 1H), 8.18 (d, J = 7.8 Hz, 1H), 8.12 (d, J = 5.1 Hz, 1H), 8.07 (s, J = 1.4 Hz, 1H), 7.92 (s, 1H), 7.88 (s, 1H), 7.78 (d, J = 8.0 Hz, 1H), 7.66 (t, J = 7.7 Hz, 1H), 7.60-7.55 (m, 2H), 7.44 (d, J = 7.4 Hz, 1H), 6.78 (d, J = 4.9 Hz, 1H), 3.82-3.53 (m, 2H), 3.45-3.21 (m, 2H), 2.34 (s, 3H), 2.33 (br s, 4H), 2.21 (s, 3H). (ESI+) m/z 455 (M + H)$^+$ Retention time = 180 mins (method 1) |
| 068 | 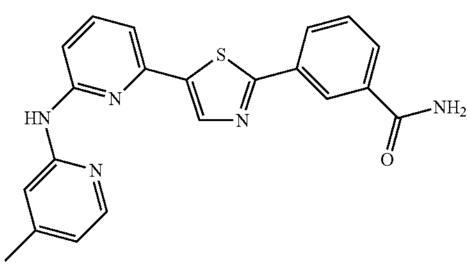 [SMILES: Cc1ccnc(Nc2cccc(-c3cnc(-c4cccc(C(N)=O)c4)s3)n2)c1] | 3-{5-[6-(4-Methyl-pyridin-2-ylamino)-pyridin-2-yl]-thiazol-2-yl}-benzamide | (300 MHz, DMSO-$d_6$) δ 9.75 (br s, 1H), 8.59 (s, 1H), 8.50 (br s, 1H), 8.22 (br s, 1H), 8.13 (d, J = 6.1 Hz, 2H), 8.00 (d, J = 7.6 Hz, 1H), 7.95 (br s, 1H), 7.75 (t, J = 7.7 Hz, 1H), 7.64 (t, J = 7.6 Hz, 1H), 7.58-7.45 (m, 3H), 6.80 (d, J = 4.9 Hz, 1H), 2.40 (s, 3H). (APCI+) m/z 388 (M + H)$^+$ Retention time = 2.28 mins (method 2) |
| 069 | 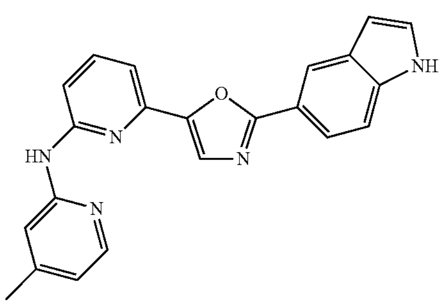 [SMILES: Cc1ccnc(Nc2cccc(-c3cnc(-c4ccc5[nH]ccc5c4)o3)n2)c1] | {6-[2-(1H-Indol-5-yl)-oxazol-5-yl]-pyridin-2-yl}-(4-methyl-pyridin-2-yl)-amine | (400 MHz, DMSO-$d_6$) δ 11.46 (s, 1H), 9.76 (s, 1H), 8.38 (s, 1H), 8.13 (d, J = 5.1 Hz, 1H), 8.00 (s, 1H), 7.89 (dd, J = 8.6, 1.5 Hz, 1H), 7.83-7.73 (m, 2H), 7.55 (dd, J = 12.7, 8.4 Hz, 2H), 7.49 (t, J = 2.7 Hz, 1H), 7.39 (d, J = 7.4 Hz, 1H), 6.79 (d, J = 4.9 Hz, 1H), 6.60 (s, 1H), 2.40 (s, 3H). (ESI+) m/z 368 (M + H)$^+$ Retention time = 2.78 mins (method 1) |
| 070 | 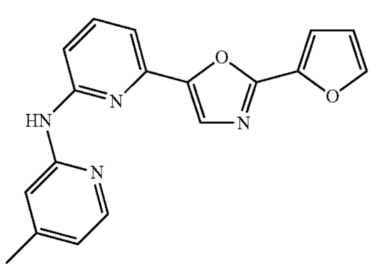 | [6-(2-Furan-2-yl-oxazol-5-yl)-pyridin-2-yl]-(4-methyl-pyridin-2-yl)-amine | (400 MHz, DMSO-$d_6$) δ 9.78 (s, 1H), 8.11 (d, J = 5.1 Hz, 1H), 7.99 (d, J = 1.1 Hz, 1H), 7.85 (s, 1H), 7.83 (s, 1H), 7.79-7.72 (m, 1H), 7.63 (d, J = 8.3 Hz, 1H), 7.32 (d, J = 7.4 Hz, 1H), 7.26 (dd, J = 3.4, 0.3 Hz, 1H), 6.82-6.72 (m, 2H), 2.32 (s, 3H). (ESI+) m/z 319 (M + H)$^+$ Retention time = 2.48 mins (method 1) |

TABLE 1-continued

| Ex # | Chemical structure | Name | $^1$H NMR/LCMS |
|---|---|---|---|
| 071 | 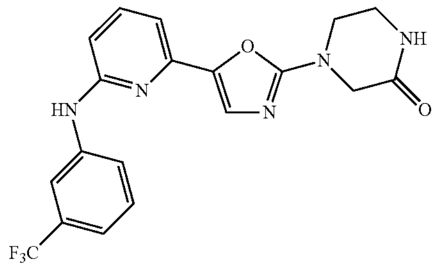 [SMILES: O=C1CN(c2ncc(-c3cccc(Nc4cccc(C(F)(F)F)c4)n3)o2)CCN1] | 4-{5-[6-(3-Trifluoromethyl-phenylamino)-pyridin-2-yl]-oxazol-2-yl}-piperazin-2-one | (400 MHz, DMSO-$d_6$) δ 9.57 (s, 1H), 8.60 (s, 1H), 8.19 (s, 1H), 7.77 (d, J = 8.2 Hz, 1H), 7.65 (t, J = 7.9 Hz, 1H), 7.51 (t, J = 8.0 Hz, 1H), 7.37 (s, 1H), 7.22 (d, J = 7.6 Hz, 1H), 7.05 (d, J = 7.5 Hz, 1H), 6.71 (d, J = 8.3 Hz, 1H), 4.07 (s, 2H), 3.74 (t, J = 5.3 Hz, 2H), 3.41-3.35 (m, 2H). (ESI+) m/z 404 (M + H)$^+$ Retention time = 3.58 mins (method 1) |
| 072 | 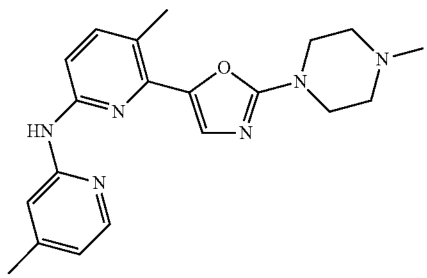 | {5-Methyl-6-[2-(4-methyl-piperazin-1-yl)-oxazol-5-yl]-pyridin-2-yl}-(4-methyl-pyridin-2-yl)-amine | (400 MHz, DMSO-$d_6$) δ 9.47 (s, 1H), 8.13-7.98 (m, 2H), 7.49 (d, J = 8.4 Hz, 1H), 7.30 (s, 1H), 7.22 (d, J = 8.3 Hz, 1H), 6.71 (d, J = 4.8 Hz, 1H), 3.55 (t, J = 5.0 Hz, 4H), 2.44 (t, J = 5.0 Hz, 4H), 2.32 (s, 3H), 2.29 (s, 3H), 2.24 (s, 3H). (ESI+) m/z 365 (M + H)$^+$ Retention time = 1.53 mins (method 1) |
| 073 | 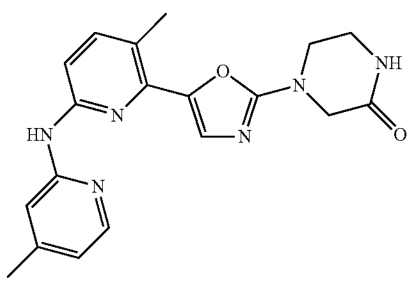 [SMILES: Cc1ccnc(Nc2ccc(C)c(-c3cnc(N4CCNC(=O)C4)o3)n2)c1] | 4-{5-[3-Methyl-6-(4-methyl-pyridin-2-ylamino)-pyridin-2-yl]-oxazol-2-yl}-piperazin-2-one | (400 MHz, DMSO-$d_6$) δ 9.48 (s, 1H), 8.18 (s, 1H), 8.07 (d, J = 5.0 Hz, 1H), 8.00 (s, 1H), 7.51 (d, J = 8.4 Hz, 1H), 7.33 (s, 1H), 7.26 (d, J = 8.3 Hz, 1H), 6.72 (d, J = 4.8 Hz, 1H), 4.09 (s, 2H), 3.82-3.64 (m, 2H), 3.44-3.33 (m, 2H), 2.34 (s, 3H), 2.31 (s, 3H). (ESI+) m/z 365 (M + H)$^+$ Retention time = 1.99 mins (method 1) |
| 074 | 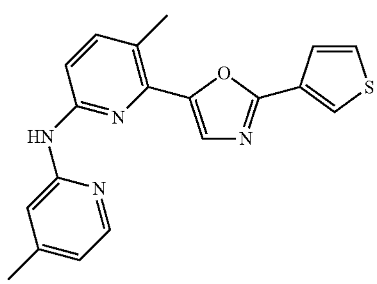 [SMILES: Cc1ccnc(Nc2ccc(C)c(-c3cnc(-c4ccsc4)o3)n2)c1] | (4-Methyl-pyridin-2-yl)-[5-methyl-6-(2-thiophen-3-yl-oxazol-5-yl)-pyridin-2-yl]-amine | (400 MHz, DMSO-$d_6$) δ 9.61 (s, 1H), 8.26 (d, J = 1.8 Hz, 1H), 8.10 (d, J = 5.1 Hz, 1H), 7.93 (s, 1H), 7.80 (dd, J = 5.0, 2.9 Hz, 1H), 7.71 (s, 1H), 7.66 (dd, J = 4.9, 0.7 Hz, 1H), 7.62 (d, J = 8.5 Hz, 1H), 7.50 (d, J = 8.4 Hz, 1H), 6.74 (d, J = 5.0 Hz, 1H), 2.49 (s, 3H), 2.32 (s, 3H). (ESI+) m/z 349 (M + H)$^+$ Retention time = 2.92 mins (method 1) |
| 075 | 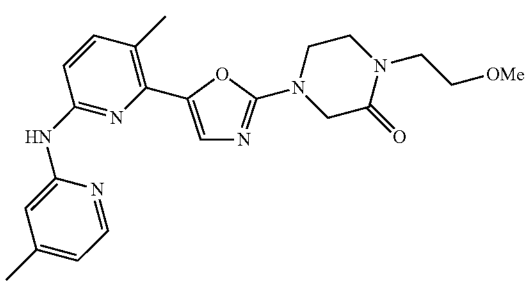 [SMILES: COCCN1CCN(c2ncc(-c3nc(Nc4cc(C)ccn4)ccc3C)o2)CC1=O] | 1-(2-Methoxy-ethyl)-4-{5-[3-methyl-6-(4-methyl-pyridin-2-ylamino)-pyridin-2-yl]-oxazol-2-yl}-piperazin-2-one | (400 MHz, DMSO-$d_6$) δ 9.51 (s, 1H), 8.07 (d, J = 5.0 Hz, 1H), 7.99 (s, 1H), 7.51 (d, J = 8.4 Hz, 1H), 7.34 (s, 1H), 7.26 (d, J = 8.4 Hz, 1H), 6.72 (d, J = 5.0 Hz, 1H), 4.16 (s, 2H), 3.81 (t, J = 5.4 Hz, 2H), 3.59-3.46 (m, 6H), 3.25 (s, 3H), 2.34 (s, 3H), 2.31 (s, 3H). (ESI+) m/z 423 (M + H)$^+$ Retention time = 2.27 mins (method 1) |

TABLE 1-continued

| Ex # | Chemical structure | Name | $^1$H NMR/LCMS |
|---|---|---|---|
| 076 | 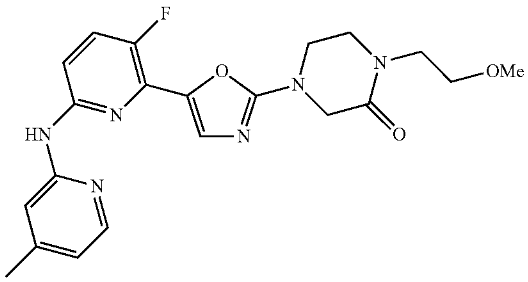 [SMILES: COCCN1CCN(c2ncc(-c3nc(Nc4cc(C)ccn4)ccc3F)o2)CC1=O] | 4-{5-[3-Fluoro-6-(4-methyl-pyridin-2-ylamino)-pyridin-2-yl]-oxazol-2-yl}-1-(2-methoxy-ethyl)-piperazin-2-one | (400 MHz, DMSO-d$_6$) δ 9.75 (s, 1H), 8.09 (d, J = 5.1 Hz, 1H), 7.95 (s, 1H), 7.66 (t, J = 9.9 Hz, 1H), 7.43 (d, J = 3.2 Hz, 1H), 7.38 (dd, J = 9.0, 3.0 Hz, 1H), 6.76 (d, J = 4.9 Hz, 1H), 4.19 (s, 2H), 3.82 (t, J = 5.5 Hz, 2H), 3.61-3.45 (m, 6H), 3.25 (s, 3H), 2.32 (s, 3H). (ESI+) m/z 427 (M + H)$^+$ Retention time = 2.17 mins (method 1) |
| 077 | 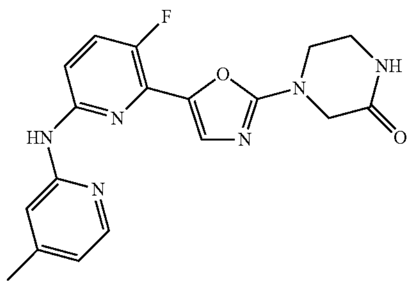 [SMILES: Cc1ccnc(Nc2ccc(F)c(-c3cnc(N4CCNC(=O)C4)o3)n2)c1] | 4-{5-[3-Fluoro-6-(4-methyl-pyridin-2-ylamino)-pyridin-2-yl]-oxazol-2-yl}-piperazin-2-one | (400 MHz, DMSO-d$_6$) δ 9.69 (s, 1H), 8.19 (s, 1H), 8.08 (d, J = 5.0 Hz, 1H), 7.96 (s, 1H), 7.64 (t, J = 9.8 Hz, 1H), 7.42 (d, J = 3.1 Hz, 1H), 7.38 (dd, J = 9.1, 3.0 Hz, 1H), 4.11 (s, 2H), 3.76 (t, J = 5.2 Hz, 2H), 3.36 (s, 2H), 2.31 (s, 3H). (ESI+) m/z 369 (M + H)$^+$ Retention time = 1.92 mins (method 1) |
| 078 | 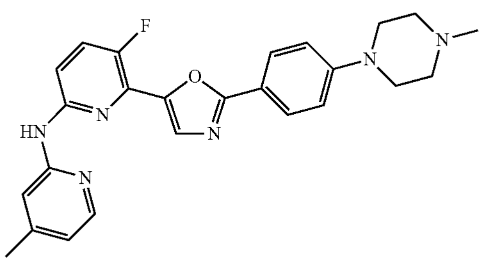 | (5-Fluoro-6-{2-[4-(4-methyl-piperazin-1-yl)-phenyl]-oxazol-5-yl}-pyridin-2-yl)-(4-methyl-pyridin-2-yl)-amine | (400 MHz, DMSO-d$_6$) δ 9.83 (s, 1H), 8.12 (d, J = 4.9 Hz, 1H), 8.03 (s, 1H), 7.94 (d, J = 8.6 Hz, 2H), 7.81-7.68 (m, 2H), 7.55 (d, J = 7.2 Hz, 1H), 7.10 (d, J = 8.6 Hz, 2H), 6.79 (d, J = 4.7 Hz, 1H), 3.31-3.23 (m, 4H), 2.46 (s, 4H), 2.39 (s, 3H), 2.26 (d, J = 19.9 Hz, 3H). (ESI+) m/z 445 (M + H)$^+$ Retention time = 1.99 mins (method 1) |
| 079 | 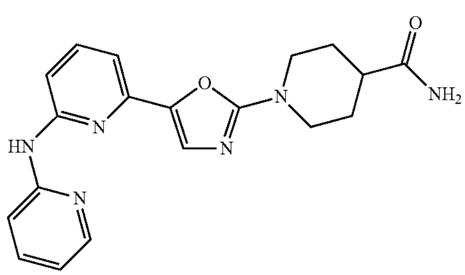 [SMILES: NC(=O)C1CCN(c2ncc(-c3cccc(Nc4ccccn4)n3)o2)CC1] | 1-{5-[6-(Pyridin-2-ylamino)-pyridin-2-yl]-oxazol-2-yl}-piperidine-4-carboxylic acid amide | (300 MHz, DMSO-d$_6$) δ 9.70 (s, 1H), 8.22 (d, J = 3.8 Hz, 1H), 7.93 (d, J = 8.4 Hz, 1H), 7.74-7.61 (m, 2H), 7.45 (d, J = 8.3 Hz, 1H), 7.42 (s, 1H), 7.33 (s, 1H), 7.03 (d, J = 7.4 Hz, 1H), 6.92-6.82 (m, 2H), 4.07 (d, J = 13.0 Hz, 2H), 3.12-3.00 (m, 2H), 2.43-2.24 (m, 1H), 1.82 (d, J = 10.7 Hz, 2H), 1.58 (dq, J = 12.5, 4.0 Hz, 2H). (ESI+) m/z 365 (M + H)$^+$ |
| 080 | 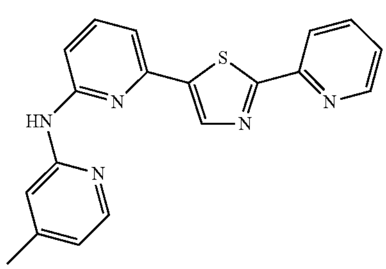 | (4-Methyl-pyridin-2-yl)-[6-(2-pyridin-2-yl-thiazol-5-yl)-pyridin-2-yl]-amine | (300 MHz, DMSO-d$_6$) δ 9.74 (br s, 1H), 8.71-8.65 (m, 1H), 8.60 (s, 1H), 8.18 (d, J = 7.9 Hz, 1H), 8.13 (d, J = 5.1 Hz, 1H), 8.04-7.93 (m, 2H), 7.75 (t, J = 7.6 Hz, 1H), 7.57-7.44 (m, 3H), 6.80 (d, J = 5.1 Hz, 1H), 2.38 (s, 3H). (APCI+) m/z 346 (M + H)$^+$ Retention time = 2.37 mins (method 2) |

TABLE 1-continued

| Ex # | Chemical structure | Name | ¹H NMR/LCMS |
|---|---|---|---|
| 081 | 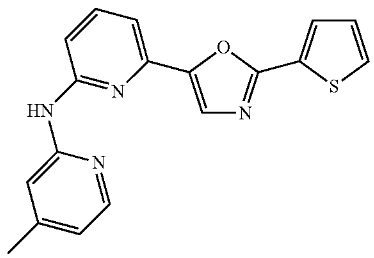 [SMILES: Cc1ccnc(Nc2cccc(-c3cnc(-c4cccs4)o3)n2)c1] | (4-Methyl-pyridin-2-yl)-[6-(2-thiophen-2-yl-oxazol-5-yl)-pyridin-2-yl]-amine | (400 MHz, DMSO-$d_6$) δ 9.80 (s, 1H), 8.12 (d, J = 5.0 Hz, 1H), 7.92-7.74 (m, 5H), 7.61 (d, J = 8.4 Hz, 1H), 7.35 (d, J = 7.4 Hz, 1H), 7.31-7.26 (m, 1H), 6.79 (d, J = 5.0 Hz, 1H), 2.36 (s, 3H). (ESI+) m/z 335 (M + H)⁺ Retention time = 2.74 mins (method 1) |
| 082 | 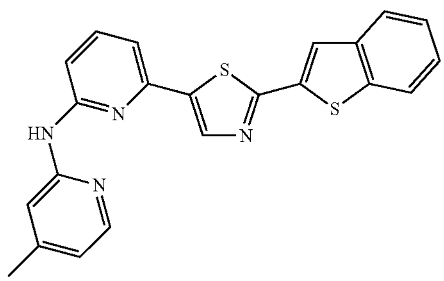 [SMILES: Cc1ccnc(Nc2cccc(-c3cnc(-c4cc5ccccc5s4)s3)n2)c1] | [6-(2-Benzo[b]-thiophen-2-yl-thiazol-5-yl)-pyridin-2-yl]-(4-methyl-pyridin-2-yl)-amine | (300 MHz, DMSO-$d_6$) δ 8.55 (s, 1H), 8.2-8.14 (m, 1H), 8.09 (s, 1H), 8.07-8.01 (m, 1H), 8.00-7.94 (m, 1H), 7.87-7.82 (m, 1H), 7.80-7.73 (m, 1H), 7.60-7.53 (m, 1H), 7.48-7.40 (m, 2H), 6.88-6.83 (m, 1H), 2.42 (s, 3H). (APCI+) m/z 401 (M + H)⁺ Retention time = 2.88 mins (method 2) |
| 083 | 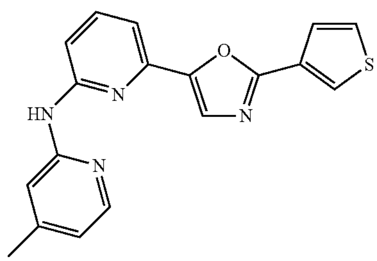 [SMILES: Cc1ccnc(Nc2cccc(-c3cnc(-c4ccsc4)o3)n2)c1] | (4-Methyl-pyridin-2-yl)-[6-(2-thiophen-3-yl-oxazol-5-yl)-pyridin-2-yl]-amine | (400 MHz, DMSO-$d_6$) δ 9.78 (s, 1H), 8.36-8.28 (m, 1H), 8.12 (d, J = 5.1 Hz, 1H), 7.85 (s, 1H), 7.82-7.74 (m, 3H), 7.68 (d, J = 5.1 Hz, 1H), 7.62 (d, J = 8.4 Hz, 1H), 7.36 (d, J = 7.4 Hz, 1H), 6.78 (d, J = 5.0 Hz, 1H), 2.35 (s, 3H). (ESI+) m/z 335 (M + H)⁺ Retention time = 2.72 mins (method 1) |
| 084 | 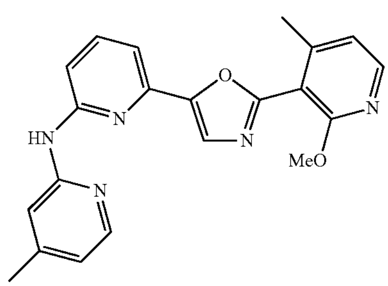 [SMILES: COc1nccc(C)c1-c1ncc(-c2cccc(Nc3cc(C)ccn3)n2)o1] | {6-[2-(2-Methoxy-4-methyl-pyridin-3-yl)-oxazol-5-yl]-pyridin-2-yl}-(4-methyl-pyridin-2-yl)-amine | (400 MHz, CDCl₃) δ 9.78 (s, 1H), 8.24 (d, J = 5.2 Hz, 1H), 8.11 (d, J = 5.1 Hz, 1H), 7.88 (s, 1H), 7.83-7.72 (m, 2H), 7.66 (d, J = 8.4 Hz, 1H), 7.28 (d, J = 7.3 Hz, 1H), 7.08 (d, J = 5.2 Hz, 1H), 6.76 (d, J = 5.0 Hz, 1H), 3.89 (s, 3H), 2.32 (s, 3H), 2.29 (s, 3H). (ESI+) m/z 374 (M + H)⁺ Retention time = 2.57 mins (method 1) |
| 085 | 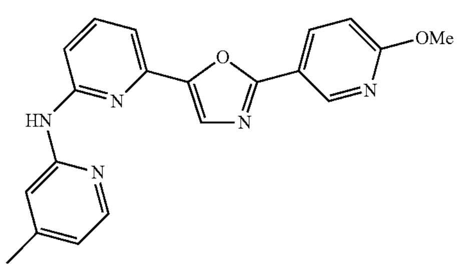 [SMILES: COc1ccc(-c2ncc(-c3cccc(Nc4cc(C)ccn4)n3)o2)cn1] | {6-[2-(6-Methoxy-pyridin-3-yl)-oxazol-5-yl]-pyridin-2-yl}-(4-methyl-pyridin-2-yl)-amine | (400 MHz, DMSO-$d_6$) δ 9.79 (s, 1H), 8.93 (d, J = 2.3 Hz, 1H), 8.35 (dd, J = 8.7, 2.4 Hz, 1H), 8.12 (d, J = 5.0 Hz, 1H), 7.87 (s, 1H), 7.84-7.74 (m, 2H), 7.60 (d, J = 8.4 Hz, 1H), 7.41 (d, J = 7.4 Hz, 1H), 7.05 (d, J = 8.7 Hz, 1H), 6.78 (d, J = 5.0 Hz, 1H), 3.96 (s, 3H), 2.35 (s, 3H). (ESI+) m/z 360 (M + H)⁺ Retention time = 2.72 mins (method 1) |

TABLE 1-continued

| Ex # | Chemical structure | Name | ¹H NMR/LCMS |
|---|---|---|---|
| 086 | 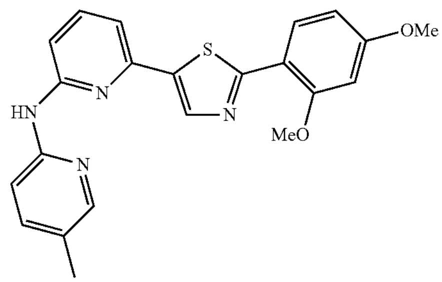 [SMILES: COc1ccc(-c2ncc(-c3cccc(Nc4ccc(C)cn4)n3)s2)c(OC)c1] | {6-[2-(2,4-Dimethoxy-phenyl)-thiazol-5-yl]-pyridin-2-yl}-(5-methyl-pyridin-2-yl)-amine | (300 MHz, DMSO-$d_6$) δ 9.64 (s, 1H), 8.45 (s, 1H), 8.24 (d, J = 8.8 Hz, 1H), 8.09 (s, 1H), 7.94 (d, J = 8.5 Hz, 1H), 7.80-7.63 (m, 1H), 7.58 (d, J = 8.6 Hz, 1H), 7.50-7.40 (m, 2H), 6.81 (d, J = 2.1 Hz, 1H), 6.78-6.68 (m, 1H), 4.08 (s, 3H), 3.86 (s, 3H), 2.25 (s, 3H). (APCI+) m/z 405 (M + H)⁺ Retention time = 2.61 mins (method 2) |
| 087 | 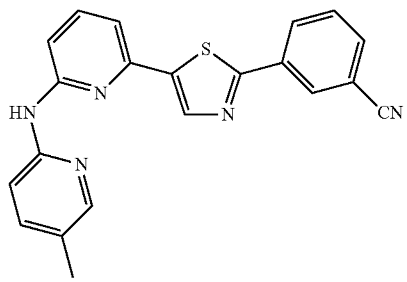 [SMILES: Cc1ccc(Nc2cccc(-c3cnc(-c4cccc(C#N)c4)s3)n2)nc1] | 3-{5-[6-(5-Methyl-pyridin-2-ylamino)-pyridin-2-yl]-thiazol-2-yl}-benzonitrile | (300 MHz, DMSO-$d_6$) δ 9.81 (br s, 1H), 8.62 (s, 1H), 8.43 (s, 1H), 8.39-8.31 (m, 1H), 8.12 (s, 1H), 7.98 (t, J = 7.5 Hz, 2H), 7.80-7.71 (m, 2H), 7.69 (d, J = 8.8 Hz, 1H), 7.53 (d, J = 7.5 Hz, 1H), 7.43 (d, J = 8.3 Hz, 1H), 2.26 (s, 3H). (APCI+) m/z 370 (M + H)⁺ Retention time = 2.63 mins (method 2) |
| 088 | 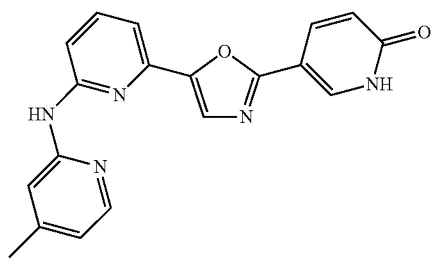 [SMILES: Cc1ccnc(Nc2cccc(-c3cnc(-c4ccc(=O)[nH]c4)o3)n2)c1] | 5-{5-[6-(4-Methyl-pyridin-2-ylamino)-pyridin-2-yl]-oxazol-2-yl}-1H-pyridin-2-one | (400 MHz, DMSO-$d_6$) δ 12.25 (s, 1H), 9.76 (s, 1H), 8.19 (s, 1H), 8.11 (d, J = 5.2 Hz, 1H), 8.07-7.99 (m, 1H), 7.84 (s, 1H), 7.79-7.70 (m, 2H), 7.59 (d, J = 8.4 Hz, 1H), 7.39 (d, J = 7.4 Hz, 1H), 6.77 (d, J = 4.4 Hz, 1H), 6.53 (d, J = 9.5 Hz, 1H), 2.34 (s, 3H). (ESI+) m/z 346 (M + H)⁺ Retention time = 1.92 mins (method 1) |
| 089 | 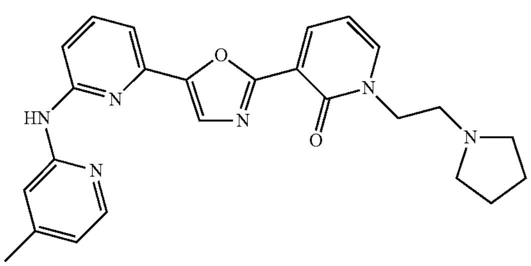 [SMILES: Cc1ccnc(Nc2cccc(-c3cnc(-c4cccn(CCN5CCCC5)c4=O)o3)n2)c1] | 3-{5-[6-(4-Methyl-pyridin-2-ylamino)-pyridin-2-yl]-oxazol-2-yl}-1-(2-pyrrolidin-1-yl-ethyl)-1H-pyridin-2-one | (400 MHz, DMSO-$d_6$) δ 9.75 (s, 1H), 8.22 (dd, J = 7.2, 2.0 Hz, 1H), 8.11 (d, J = 5.1 Hz, 1H), 7.95 (dd, J = 6.6, 1.9 Hz, 1H), 7.89 (s, 1H), 7.83-7.69 (m, 2H), 7.58 (d, J = 8.3 Hz, 1H), 7.29 (d, J = 7.4 Hz, 1H), 6.77 (d, J = 4.9 Hz, 1H), 6.42 (t, J = 6.9 Hz, 1H), 4.12 (t, J = 6.3 Hz, 2H), 2.74 (t, J = 6.3 Hz, 2H), 2.35 (s, 3H), 1.77-1.58 (m, 4H). (ESI+) m/z 343 (M + H)⁺ Retention time = 1.67 mins (method 1) |
| 090 | 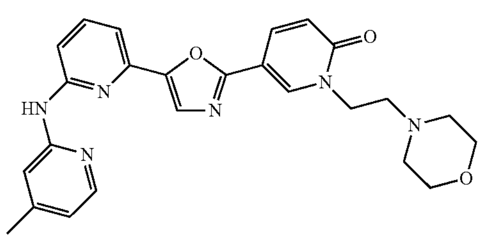 [SMILES: Cc1ccnc(Nc2cccc(-c3cnc(-c4ccc(=O)n(CCN5CCOCC5)c4)o3)n2)c1] | 5-{5-[6-(4-Methyl-pyridin-2-ylamino)-pyridin-2-yl]-oxazol-2-yl}-1-(2-morpholin-4-yl-ethyl)-1H-pyridin-2-one | (400 MHz, DMSO-$d_6$) δ 9.71 (s, 1H), 8.57 (d, J = 2.5 Hz, 1H), 8.11 (d, J = 5.1 Hz, 1H), 8.01 (dd, J = 9.4, 2.5 Hz, 1H), 7.86-7.70 (m, 3H), 7.60 (d, J = 8.4 Hz, 1H), 7.35 (d, J = 7.4 Hz, 1H), 6.77 (d, J = 5.0 Hz, 1H), 6.57 (d, J = 9.5 Hz, 1H), 4.15 (t, J = 6.1 Hz, 2H), 3.56 (t, J = 4.4 Hz, 4H), 2.62 (t, J = 6.1 Hz, 2H), 2.49-2.45 (m, 4H), 2.34 (s, 3H). (ESI+) m/z 459 (M + H)⁺ Retention time = 1.63 mins (method 1) |

TABLE 1-continued

| Ex # | Chemical structure | Name | $^1$H NMR/LCMS |
|---|---|---|---|
| 091 | 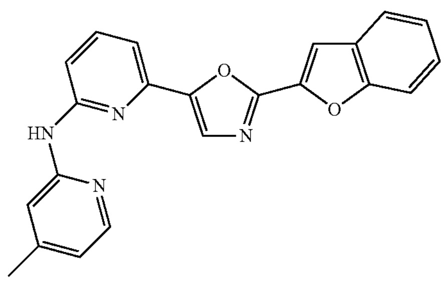 [SMILES: Cc1ccnc(Nc2cccc(-c3cnc(-c4cc5ccccc5o4)o3)n2)c1] | [6-(2-Benzofuran-2-yl-oxazol-5-yl)-pyridin-2-yl]-(4-methyl-pyridin-2-yl)-amine | (400 MHz, DMSO-d$_6$) δ 9.81 (s, 1H), 8.13 (d, J = 5.0 Hz, 1H), 7.96 (s, 1H), 7.92 (s, 1H), 7.86-7.69 (m, 4H), 7.65 (d, J = 8.4 Hz, 1H), 7.50 (t, J = 7.6 Hz, 1H), 7.43-7.34 (m, 2H), 6.79 (d, J = 4.9 Hz, 1H), 2.39 (s, 3H). (ESI+) m/z 369 (M + H)$^+$ Retention time = 3.21 mins (method 1) |
| 092 | 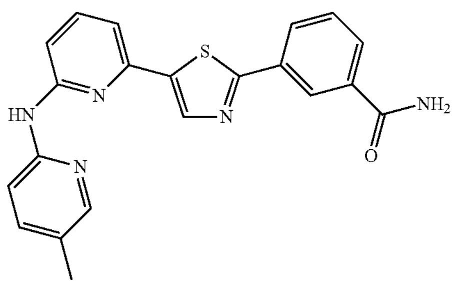 [SMILES: Cc1ccc(Nc2cccc(-c3cnc(-c4cccc(C(N)=O)c4)s3)n2)nc1] | 3-{5-[6-(5-Methyl-pyridin-2-ylamino)-pyridin-2-yl]-thiazol-2-yl}-benzamide | (300 MHz, DMSO-d$_6$) δ 9.71 (br s, 1H), 8.58 (s, 1H), 8.49 (br s, 1H), 8.24 (br s, 1H), 8.16 (d, J = 7.7 Hz, 1H), 8.11 (br s, 1H), 8.01 (d, J = 7.6 Hz, 1H), 7.94 (d, J = 8.5 Hz, 1H), 7.74 (t, J = 8.0 Hz, 1H), 7.68-7.59 (m, 2H), 7.58-7.45 (m, 3H), 2.25 (s, 3H). (APCI+) m/z 388 (M + H)$^+$ Retention time = 2.35 mins (method 2) |
| 093 | 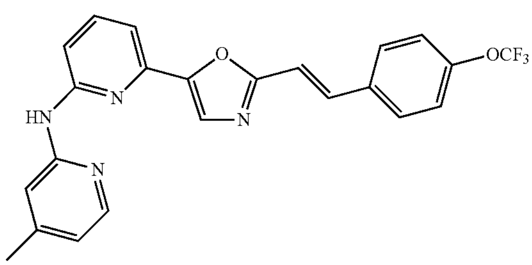 [SMILES: Cc1ccnc(Nc2cccc(-c3cnc(/C=C/c4ccc(OC(F)(F)F)cc4)o3)n2)c1] | (4-Methyl-pyridin-2-yl)-(6-{2-[2-(4-trifluoromethoxy-phenyl)-vinyl]-oxazol-5-yl}-pyridin-2-yl)-amine | (300 MHz, DMSO-d$_6$) δ 9.78 (s, 1H), 8.12 (d, J = 5.0 Hz, 1H), 7.90-7.53 (m, 8H), 7.44-7.31 (m, 3H), 6.78 (d, J = 5.1 Hz, 1H), 2.35 (s, 3H). (ESI+) m/z 439 (M + H)$^+$ |
| 094 | 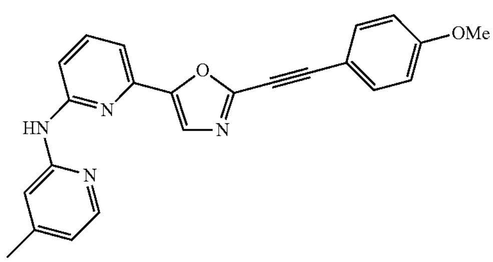 [SMILES: COc1ccc(C#Cc2ncc(-c3cccc(Nc4cc(C)ccn4)n3)o2)cc1] | {6-[2-(4-Methoxy-phenylethynyl)-oxazol-5-yl]-pyridin-2-yl}-(4-methyl-pyridin-2-yl)-amine | (400 MHz, DMSO-d$_6$) δ 9.79 (s, 1H), 8.11 (d, J = 5.1 Hz, 1H), 7.84 (s, 1H), 7.80-7.64 (m, 5H), 7.31 (d, J = 7.1 Hz, 1H), 7.20-6.91 (m, 2H), 6.77 (d, J = 5.0 Hz, 1H), 3.84 (s, 3H), 2.33 (s, 3H). (ESI+) m/z 383 (M + H)$^+$ Retention time = 3.35 mins (method 1) |
| 095 | 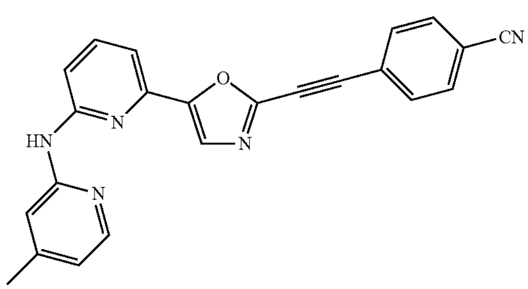 [SMILES: Cc1ccnc(Nc2cccc(-c3cnc(C#Cc4ccc(C#N)cc4)o3)n2)c1] | 4-{5-[6-(4-Methyl-pyridin-2-ylamino)-pyridin-2-yl]-oxazol-2-ylethynyl}-benzonitrile | (ESI+) m/z 378 (M + H)$^+$ Retention time = 3.12 mins (method 1) |

TABLE 1-continued

| Ex # | Chemical structure | Name | ¹H NMR/LCMS |
|---|---|---|---|
| 096 | 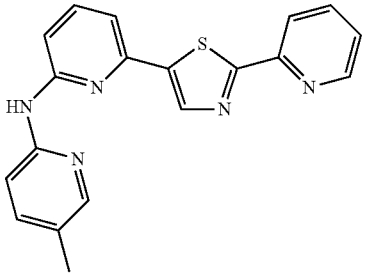 [SMILES: Cc1ccc(Nc2cccc(-c3cnc(-c4ccccn4)s3)n2)nc1] | (5-Methyl-pyridin-2-yl)-[6-(2-pyridin-2-yl-thiazol-5-yl)-pyridin-2-yl]-amine | (300 MHz, DMSO-d$_6$) δ 9.71 (br s, 1H), 8.69 (d, J = 4.8 Hz, 1H), 8.60 (s, 1H), 8.18 (d, J = 7.3 Hz, 1H), 8.11 (br s, 1H), 8.05-7.93 (m, 2H), 7.73 (t, J = 7.9 Hz, 1H), 7.62 (dd, J = 8.5, 2.1 Hz, 1H), 7.57-7.48 (m, 2H), 7.44 (d, J = 8.3 Hz, 1H), 2.26 (s, 3H). (APCI+) m/z 346 (M + H)$^+$ Retention time = 2.39 mins (method 2) |
| 097 | 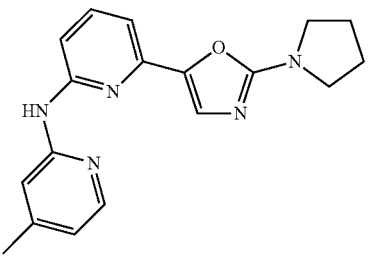 [SMILES: Cc1ccnc(Nc2cccc(-c3cnc(N4CCCC4)o3)n2)c1] | (4-Methyl-pyridin-2-yl)-[6-(2-pyrrolidin-1-yl-oxazol-5-yl)-pyridin-2-yl]-amine | (400 MHz, DMSO) δ 9.55 (d, J = 12.2 Hz, 1H), 8.08 (d, J = 5.1 Hz, 1H), 7.86 (s, 1H), 7.62 (t, J = 7.9 Hz, 1H), 7.37 (t, J = 4.1 Hz, 2H), 6.97 (d, J = 7.5 Hz, 1H), 6.73 (d, J = 5.0 Hz, 1H), 3.54-3.48 (m, 4H), 2.30 (s, J = 8.0 Hz, 3H), 1.98-1.93 (m, 4H). (ESI+) m/z 322 (M + H)$^+$ |
| 098 | 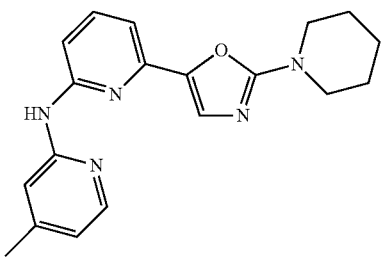 [SMILES: Cc1ccnc(Nc2cccc(-c3cnc(N4CCCCC4)o3)n2)c1] | (4-Methyl-pyridin-2-yl)-[6-(2-piperidin-1-yl-oxazol-5-yl)-pyridin-2-yl]-amine | (300 MHz, DMSO-d$_6$) δ 9.61 (s, 1H), 8.09 (d, J = 5.1 Hz, 1H), 7.90 (s, 1H), 7.62 (t, J = 8.1 Hz, 1H), 7.43-7.30 (m, 2H), 7.02 (d, J = 7.3 Hz, 1H), 6.74 (d, J = 4.0 Hz, 1H), 3.53 (s, 4H), 2.30 (s, 3H), 1.61 (s, 6H). (ESI+) m/z 336 (M + H)$^+$ |
| 099 | 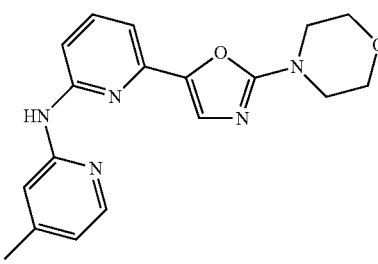 | (4-Methyl-pyridin-2-yl)-[6-(2-morpholin-4-yl-oxazol-5-yl)-pyridin-2-yl]-amine | (300 MHz, DMSO-d$_6$) δ 9.63 (s, 1H), 8.08 (d, J = 5.0 Hz, 1H), 7.84 (s, 1H), 7.64 (t, J = 7.9 Hz, 1H), 7.44-7.38 (m, 2H), 7.04 (d, J = 7.4 Hz, 1H), 6.74 (d, J = 4.7 Hz, 1H), 3.76-3.68 (m, 4H), 3.56-3.47 (m, 4H), 2.29 (s, 3H). (ESI+) m/z 338 (M + H)$^+$ |
| 100 | 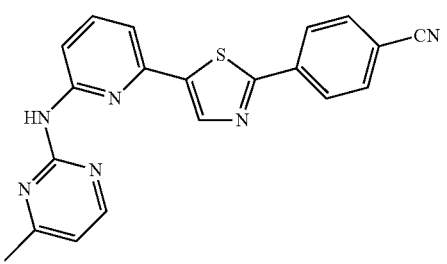 [SMILES: Cc1ccnc(Nc2cccc(-c3cnc(-c4ccc(C#N)cc4)s3)n2)n1] | 4-{5-[6-(4-Methylpyrimidin-2-ylamino)-pyridin-2-yl]-thiazol-2-yl}-benzonitrile | (300 MHz, DMSO-d$_6$) δ 9.65 (s, 1H), 8.67 (s, 1H), 8.44 (d, J = 5.0 Hz, 1H), 8.27 (d, J = 8.3 Hz, 1H), 8.17 (d, J = 8.2 Hz, 2H), 8.01 (d, J = 8.4 Hz, 2H), 7.87 (t, J = 7.9 Hz, 1H), 7.66 (d, J = 7.6 Hz, 1H), 6.90 (d, J = 5.0 Hz, 1H), 2.43 (s, 3H). (APCI+) m/z 371 (M + H)$^+$ Retention time = 3.94 mins (method 2) |
| 101 | 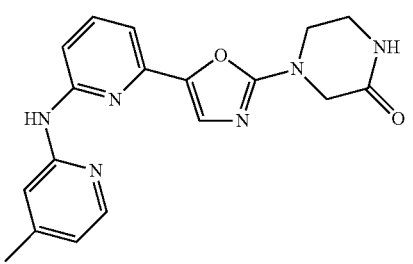 [SMILES: Cc1ccnc(Nc2cccc(-c3cnc(N4CCNC(=O)C4)o3)n2)c1] | 4-{5-[6-(4-Methyl-pyridin-2-ylamino)-pyridin-2-yl]-oxazol-2-yl}-piperazin-2-one | ¹H NMR (300 MHz, DMSO-d$_6$) δ 11.65 (br s, 1H), 8.35 (d, J = 6.2 Hz, 1H), 8.22 (s, 1H), 7.94-7.80 (m, 2H), 7.44 (s, 1H), 7.37 (d, J = 7.3 Hz, 1H), 7.19-7.10 (m, 2H), 4.12 (s, 2H), 3.81-3.72 (m, 2H), 3.36 (s, 2H), 2.47 (s, 3H). (ESI+) m/z 351 (M + H)$^+$ |

TABLE 1-continued

| Ex # | Chemical structure | Name | ¹H NMR/LCMS |
|---|---|---|---|
| 102 | 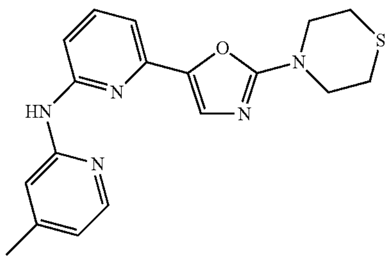 [SMILES: Cc1ccnc(Nc2cccc(-c3cnc(N4CCSCC4)o3)n2)c1] | (4-Methyl-pyridin-2-yl)-[6-(2-thiomorpholin-4-yl-oxazol-5-yl)-pyridin-2-yl]-amine | (300 MHz, DMSO-$d_6$) δ 9.62 (s, 1H), 8.08 (d, J = 4.3 Hz, 1H), 7.86 (s, 1H), 7.62 (t, J = 7.4 Hz, 1H), 7.49-7.25 (m, 2H), 7.04 (d, J = 7.4 Hz, 1H), 6.73 (s, 1H), 3.84 (s, 4H), 2.71 (s, 4H), 2.30 (s, 3H).<br>(ESI+) m/z 354 (M + H)⁺ |
| 103 | 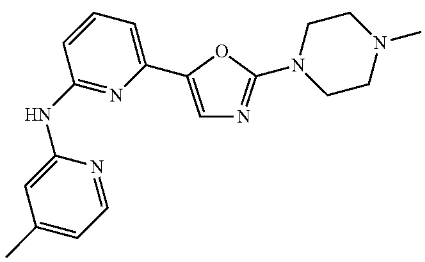 | {6-[2-(4-Methyl-piperazin-1-yl)-oxazol-5-yl]-pyridin-2-yl}-(4-methyl-pyridin-2-yl)-amine | (300 MHz, DMSO) δ 9.61 (s, 1H), 8.08 (d, J = 5.1 Hz, 1H), 7.87 (s, 1H), 7.63 (t, J = 7.9 Hz, 1H), 7.38 (d, J = 6.5 Hz, 2H), 7.03 (d, J = 7.5 Hz, 1H), 6.74 (d, J = 5.0 Hz, 1H), 3.55-3.50 (m, 4H), 2.46-2.36 (m, 4H), 2.29 (s, 3H), 2.23 (s, 3H).<br>(ESI+) m/z 351 (M + H)⁺ |
| 104 | 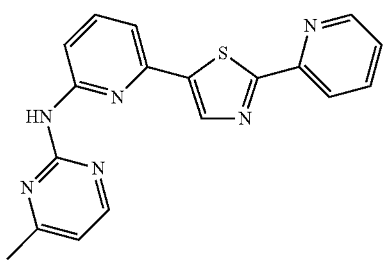 [SMILES: Cc1ccnc(Nc2cccc(-c3cnc(-c4ccccn4)s3)n2)n1] | (4-Methyl-pyrimidin-2-yl)-[6-(2-pyridin-2-yl-thiazol-5-yl)-pyridin-2-yl]-amine | (300 MHz, DMSO-$d_6$) δ 9.74 (s, 1H), 8.68 (d, J = 4.7 Hz, 1H), 8.40 (d, J = 5.0 Hz, 1H), 8.31 (s, 1H), 8.29 (s, 1H), 8.16 (d, J = 7.9 Hz, 1H), 8.00 (t, J = 7.0 Hz, 1H), 7.80 (d, J = 6.6 Hz, 1H), 7.55-7.48 (m, 1H), 7.45-7.33 (m, 2H), 6.80 (d, J = 5.0 Hz, 1H), 2.41 (s, 3H).<br>(APCI+) m/z 346 (M + H)⁺<br>Retention time = 3.71 mins (method 2) |
| 105 | 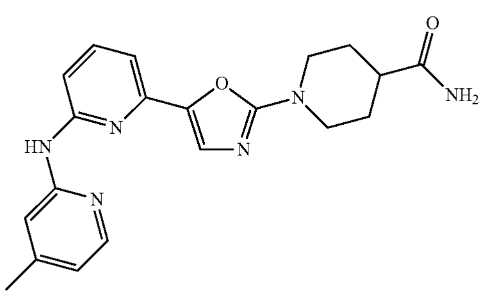 [SMILES: Cc1ccnc(Nc2cccc(-c3cnc(N4CCC(C(N)=O)CC4)o3)n2)c1] | 1-{5-[6-(4-Methyl-pyridin-2-ylamino)-pyridin-2-yl]-oxazol-2-yl}-piperidine-4-carboxylic acid amide | (300 MHz, DMSO-$d_6$) δ 9.61 (s, 1H), 8.08 (d, J = 5.1 Hz, 1H), 7.89 (s, 1H), 7.63 (t, J = 7.9 Hz, 1H), 7.40-7.31 (m, 3H), 7.03 (d, J = 7.4 Hz, 1H), 6.84 (s, 1H), 6.74 (d, J = 5.0 Hz, 1H), 4.08 (d, J = 12.8 Hz, 2H), 3.06 (t, J = 11.4 Hz, 2H), 2.42-2.32 (m, 1H), 2.30 (s, 3H), 1.81 (d, J = 10.6 Hz, 2H), 1.67-1.51 (m, 2H).<br>(ESI+) m/z 379 (M + H)⁺ |
| 106 | 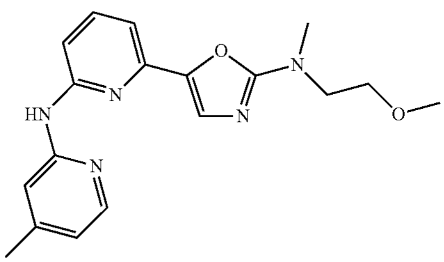 | (4-Methyl-pyridin-2-yl)-{6-[2-(2-methoxyethylamino)oxazol-5-yl])-pyridin-2-yl}-amine | ¹H NMR (300 MHz, DMSO-$d_6$) δ 9.59 (s, 1H), 8.08 (d, J = 5.3 Hz, 1H), 7.86 (s, 1H), 7.62 (t, J = 8.1 Hz, 1H), 7.40-7.24 (m, 2H), 6.99 (d, J = 7.4 Hz, 1H), 6.73 (d, J = 5.3 Hz, 1H), 3.71-3.60 (m, J = 5.1 Hz, 2H), 3.60-3.49 (m, J = 4.5 Hz, 2H), 3.27 (s, 3H), 3.12 (s, 3H), 2.30 (s, 3H).<br>(ESI+) m/z 340 (M + H)⁺ |

TABLE 1-continued

| Ex # | Chemical structure | Name | $^1$H NMR/LCMS |
|------|-------------------|------|----------------|
| 107 | 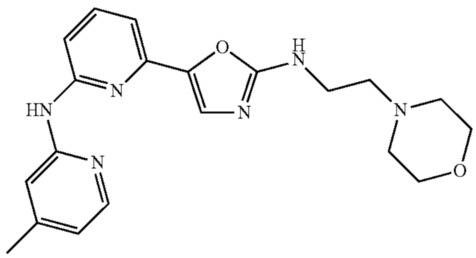 [SMILES: Cc1ccnc(Nc2cccc(-c3cnc(NCCN4CCOCC4)o3)n2)c1] | (4-Methyl-pyridin-2-yl)-{6-[2-(2-morpholin-4-yl-ethyl)-amino-oxazol-5-yl])-pyridin-2-yl}-amine | (300 MHz, DMSO-$d_6$) δ 9.59 (s, 1H), 8.08 (d, J = 5.0 Hz, 1H), 7.76 (s, 1H), 7.63 (t, J = 7.9 Hz, 1H), 7.50-7.40 (m, 2H), 7.30 (s, 1H), 6.91 (d, J = 7.5 Hz, 1H), 6.73 (d, J = 4.8 Hz, 1H), 3.61-3.51 (m, 4H), 3.42-3.34 (m, 2H), 2.49-2.44 (m, 2H), 2.46-2.38 (m, 4H), 2.31 (s, 3H). (ESI+) m/z 381 (M + H)$^+$ |
| 108 | 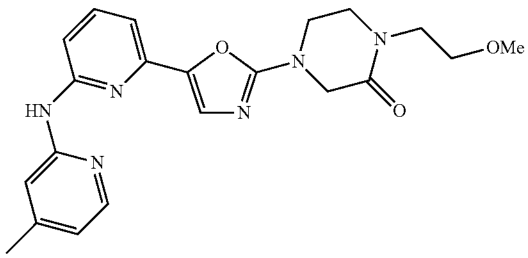 [SMILES: COCCN1CCN(c2ncc(-c3cccc(Nc4cc(C)ccn4)n3)o2)CC1=O] | 1-(2-Methoxy-ethyl)-4-{5-[6-(4-methyl-pyridin-2-ylamino)-pyridin-2-yl]-oxazol-2-yl}-piperazin-2-one | (400 MHz, DMSO-$d_6$) δ 9.60 (s, 1H), 8.08 (d, J = 5.1 Hz, 1H), 7.84 (s, 1H), 7.65 (t, J = 8.0 Hz, 1H), 7.42 (t, J = 4.1 Hz, 2H), 7.08 (d, J = 7.5 Hz, 1H), 6.74 (d, J = 4.9 Hz, 1H), 4.14 (s, 2H), 3.82-3.78 (m, 2H), 3.56 (d, J = 6.0 Hz, 4H), 3.49 (d, J = 4.7 Hz, 2H), 3.25 (s, 3H), 2.31 (s, 3H). (ESI+) m/z 409 (M + H)$^+$ Retention time = 2.10 mins (method 1) |
| 109 | 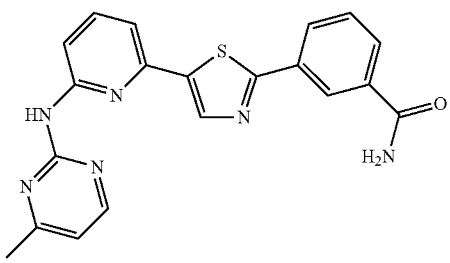 [SMILES: Cc1ccnc(Nc2cccc(-c3cnc(-c4cccc(C(N)=O)c4)s3)n2)n1] | 3-{5-[6-(4-Methyl-pyrimidin-2-ylamino)-pyridin-2-yl]-thiazol-2-yl}-benzamide | (300 MHz, DMSO-$d_6$) δ 9.60 (br s, 1H), 8.60 (s, 1H), 8.49-8.39 (m, 2H), 8.29-8.20 (m, 2H), 8.13 (d, J = 8.0 Hz, 1H), 8.00 (d, J = 7.4 Hz, 1H), 7.86 (t, J = 8.0 Hz, 1H), 7.67-7.59 (m, 2H), 7.53 (br s, 1H), 6.89 (d, J = 4.9 Hz, 1H), 2.42 (s, 3H). (APCI+) m/z 389 (M + H)$^+$ Retention time = 3.28 mins (method 2) |
| 110 | 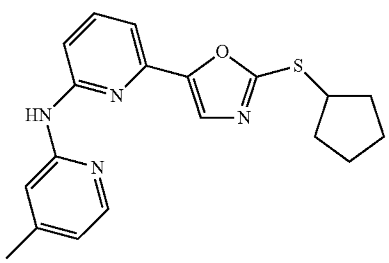 [SMILES: Cc1ccnc(Nc2cccc(-c3cnc(SC4CCCC4)o3)n2)c1] | [6-(2-Cyclopentyl-sulfanyl-oxazol-5-yl)-pyridin-2-yl]-(4-methyl-pyridin-2-yl)-amine | (300 MHz, DMSO) δ 9.75 (s, 1H), 8.10 (d, J = 5.0 Hz, 1H), 7.68 (m, 4H), 7.18 (d, J = 7.3, 1H), 6.76 (d, J = 4.6 Hz, 1H), 4.01 (m, 1H), 3.33 (s, 3H), 2.31 (s, 3H), 2.24 (m, 3H), 1.55-1.78 (m, 6H). |
| 111 | 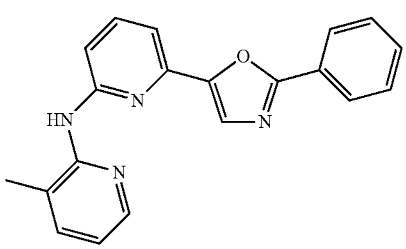 [SMILES: Cc1cccnc1Nc1cccc(-c2cnc(-c3ccccc3)o2)n1] | (3-Methyl-pyridin-2-yl)-[6-(2-phenyl-oxazol-5-yl)-pyridin-2-yl]-amine | (400 MHz, DMSO-$d_6$) δ 8.48 (s, 1H), 8.23-8.06 (m, 3H), 7.95-7.76 (m, 3H), 7.69-7.54 (m, 4H), 7.44 (d, J = 7.3 Hz, 1H), 7.03-6.87 (m, 1H), 2.34 (s, 3H). |
| 112 | 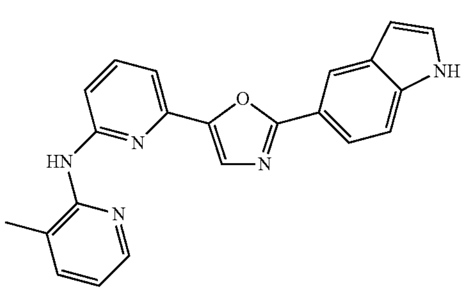 [SMILES: Cc1cccnc1Nc1cccc(-c2cnc(-c3ccc4[nH]ccc4c3)o2)n1] | {6-[2-(1H-Indol-5-yl)-oxazol-5-yl]-pyridin-2-yl}-(3-methyl-pyridin-2-yl)-amine | (400 MHz, DMSO-$d_6$) δ 11.46 (s, 1H), 8.46 (s, 1H), 8.39-8.33 (m, 1H), 8.15 (dd, J = 4.7, 1.5 Hz, 1H), 7.91-7.84 (m, 2H), 7.83-7.77 (m, 1H), 7.76 (s, 1H), 7.61-7.53 (m, 2H), 7.51-7.46 (m, 1H), 7.43 (d, J = 7.3 Hz, 1H), 6.95 (dd, J = 7.3, 4.9 Hz, 1H), 6.61 (d, J = 2.0 Hz, 1H), 2.35 (s, 3H). (ESI+) m/z 368 (M + H)$^+$ Retention time = 2.70 mins (method 1) |

TABLE 1-continued

| Ex # | Chemical structure | Name | $^1$H NMR/LCMS |
|---|---|---|---|
| 113 | 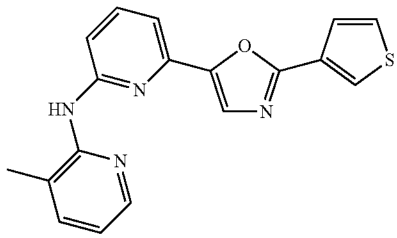 [SMILES: Cc1cccnc1Nc1cccc(-c2cnc(-c3ccsc3)o2)n1] | (3-Methyl-pyridin-2-yl)-[6-(2-thiophen-3-yl-oxazol-5-yl)-pyridin-2-yl]-amine | (400 MHz, DMSO-d$_6$) δ 8.46 (s, 1H), 8.33 (dd, J = 2.9, 1.3 Hz, 1H), 8.14 (dd, J = 4.8, 1.5 Hz, 1H), 7.88 (d, J = 8.2 Hz, 1H), 7.84-7.76 (m, 2H), 7.75 (s, 1H), 7.67 (dd, J = 5.1, 1.2 Hz, 1H), 7.58 (d, J = 7.2 Hz, 1H), 7.40 (d, J = 7.2 Hz, 1H), 6.95 (dd, J = 7.3, 4.9 Hz, 1H), 2.34 (s, 3H). (ESI+) m/z 336 (M + H)$^+$ Retention time = 2.63 mins (method 1) |
| 114 | 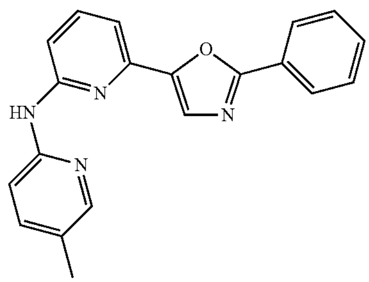 [SMILES: Cc1ccc(Nc2cccc(-c3cnc(-c4ccccc4)o3)n2)nc1] | (5-Methyl-pyridin-2-yl)-[6-(2-phenyl-oxazol-5-yl)-pyridin-2-yl]-amine | (400 MHz, DMSO-d$_6$) δ 9.76 (s, 1H), 8.19-8.07 (m, 3H), 7.94 (d, J = 8.4 Hz, 1H), 7.87 (s, 1H), 7.78 (t, J = 7.9 Hz, 1H), 7.66-7.56 (m, 5H), 7.38 (d, J = 7.4 Hz, 1H), 2.24 (s, 3H). (ESI+) m/z 329 (M + H)$^+$ Retention time = 2.91 mins (method 1) |
| 115 | 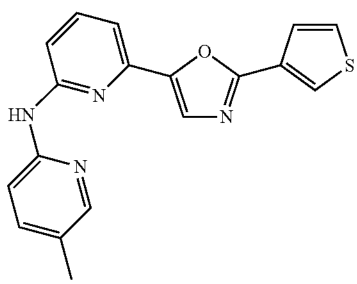 [SMILES: Cc1ccc(Nc2cccc(-c3cnc(-c4ccsc4)o3)n2)nc1] | (5-Methyl-pyridin-2-yl)-[6-(2-thiophen-3-yl-oxazol-5-yl)-pyridin-2-yl]-amine | (400 MHz, DMSO-d$_6$) δ 8.46 (s, 1H), 8.33 (dd, J = 2.9, 1.3 Hz, 1H), 8.14 (dd, J = 4.8, 1.5 Hz, 1H), 7.88 (d, J = 8.2 Hz, 1H), 7.84-7.76 (m, 2H), 7.75 (s, 1H), 7.67 (dd, J = 5.1, 1.2 Hz, 1H), 7.58 (d, J = 7.2 Hz, 1H), 7.40 (d, J = 7.2 Hz, 1H), 6.95 (dd, J = 7.3, 4.9 Hz, 1H), 2.34 (s, 3H). (ESI+) m/z 335 (M + H)$^+$ Retention time = 2.73 mins (method 1) |
| 116 | 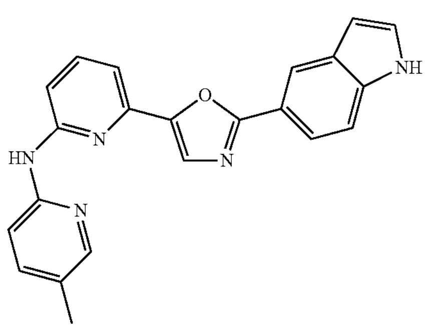 [SMILES: Cc1ccc(Nc2cccc(-c3cnc(-c4ccc5[nH]ccc5c4)o3)n2)nc1] | {6-[2-(1H-Indol-5-yl)-oxazol-5-yl]-pyridin-2-yl}-(5-methyl-pyridin-2-yl)-amine | (400 MHz, DMSO-d$_6$) δ 11.47 (s, 1H), 9.74 (s, 1H), 8.37 (s, 1H), 8.10 (d, J = 2.1 Hz, 1H), 7.94 (d, J = 8.5 Hz, 1H), 7.88 (dd, J = 8.6, 1.6 Hz, 1H), 7.81 (s, 1H), 7.80-7.73 (m, 1H), 7.63-7.54 (m, 3H), 7.51-7.47 (m, 1H), 7.37 (d, J = 7.4 Hz, 1H), 6.66-6.57 (m, 1H), 2.25 (s, 3H). (ESI+) m/z 368 (M + H)$^+$ Retention time = 2.76 mins (method 1) |
| 117 | 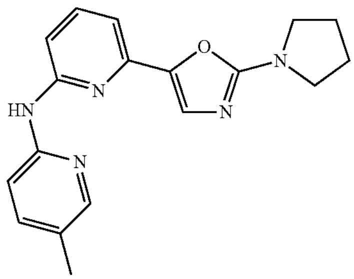 [SMILES: Cc1ccc(Nc2cccc(-c3cnc(N4CCCC4)o3)n2)nc1] | (5-Methyl-pyridin-2-yl)-[6-(2-pyrrolidin-1-yl-oxazol-5-yl)-pyridin-2-yl]-amine | (400 MHz, DMSO-d$_6$) δ 9.56 (s, 1H), 8.06 (s, 1H), 7.90 (d, J = 8.5 Hz, 1H), 7.62 (t, J = 7.9 Hz, 1H), 7.54 (dd, J = 8.5, 2.2 Hz, 1H), 7.42-7.32 (m, 2H), 6.94 (d, J = 7.5 Hz, 1H), 3.50 (t, J = 6.5 Hz, 4H), 2.22 (s, 3H), 1.96 (dd, J = 7.9, 5.2 Hz, 4H). (ESI+) m/z 322 (M + H)$^+$ Retention time = 2.20 mins (method 1) |

TABLE 1-continued

| Ex # | Chemical structure | Name | ¹H NMR/LCMS |
|---|---|---|---|
| 118 | 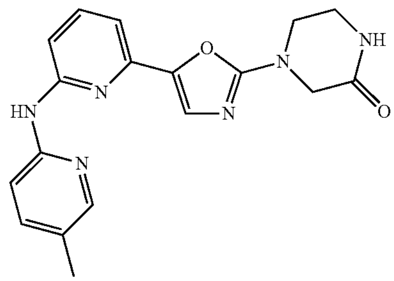 [SMILES: Cc1ccc(Nc2cccc(-c3cnc(N4CCNC(=O)C4)o3)n2)nc1] | 4-{5-[6-(5-Methyl-pyridin-2-ylamino)-pyridin-2-yl]-oxazol-2-yl}-piperazine-2-one | (400 MHz, DMSO-$d_6$) δ 9.61 (s, 1H), 8.20 (s, 1H), 8.07 (s, 1H), 7.88 (d, J = 8.5 Hz, 1H), 7.64 (t, J = 7.9 Hz, 1H), 7.54 (d, J = 8.5 Hz, 1H), 7.48-7.39 (m, 2H), 7.04 (d, J = 7.5 Hz, 1H), 4.07 (s, 2H), 3.73 (t, J = 5.2 Hz, 2H), 3.44 (q, J = 6.9 Hz, 2H), 2.22 (s, 3H). |
| 119 | 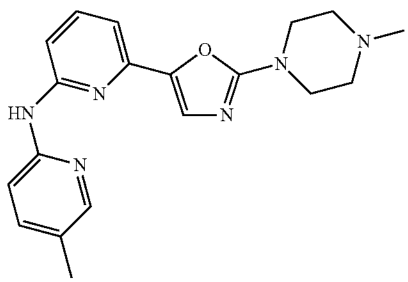 [SMILES: Cc1ccc(Nc2cccc(-c3cnc(N4CCN(C)CC4)o3)n2)nc1] | {6-[2-(4-Methyl-piperazin-1-yl)-oxazol-5-yl]-pyridin-2-yl}-(5-methyl-pyridin-2-yl)-amine | (400 MHz, DMSO-$d_6$) δ 9.41 (s, 1H), 8.06 (s, 1H), 7.86 (d, J = 8.5 Hz, 1H), 7.62 (t, J = 7.9 Hz, 1H), 7.52 (dd, J = 8.5, 2.2 Hz, 1H), 7.40 (d, J = 8.4 Hz, 1H), 7.38 (s, 1H), 7.00 (d, J = 7.5 Hz, 1H), 3.58-3.47 (m, 4H), 2.47-2.39 (m, 4H), 2.25 (s, 3H), 2.23 (s, 3H). (ESI+) m/z 351 (M + H)⁺ Retention time = 1.78 mins (method 1) |
| 120 | 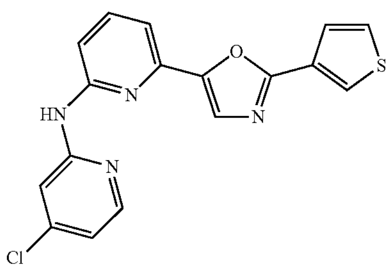 [SMILES: Clc1ccnc(Nc2cccc(-c3cnc(-c4ccsc4)o3)n2)c1] | (4-Chloro-pyridin-2-yl)-[6-(2-thiophen-3-yl-oxazol-5-yl)-pyridin-2-yl]-amine | (400 MHz, DMSO-$d_6$) δ 10.17 (s, 1H), 8.38 (d, J = 1.7 Hz, 1H), 8.32 (d, J = 2.8 Hz, 1H), 8.25 (d, J = 5.4 Hz, 1H), 7.85-7.77 (m, 3H), 7.70 (d, J = 5.0 Hz, 1H), 7.45 (dd, J = 13.3, 7.9 Hz, 2H), 7.05 (dd, J = 5.4, 1.8 Hz, 1H). (ESI+) m/z 355 (M + H)⁺ Retention time = 3.73 mins (method 1) |
| 121 | 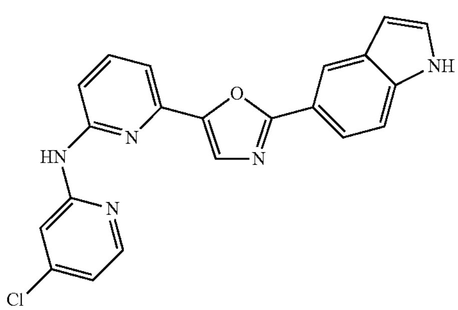 [SMILES: Clc1ccnc(Nc2cccc(-c3cnc(-c4ccc5[nH]ccc5c4)o3)n2)c1] | (4-Chloro-pyridin-2-yl)-{6-[2-(1H-indol-5-yl)-oxazol-5-yl]-pyridin-2-yl}-amine | (400 MHz, DMSO-$d_6$) δ 11.47 (s, 1H), 10.19 (s, 1H), 8.59 (d, J = 1.7 Hz, 1H), 8.43 (s, 1H), 8.27 (d, J = 5.4 Hz, 1H), 7.92 (dd, J = 8.5, 1.5 Hz, 1H), 7.87-7.77 (m, 2H), 7.56 (d, J = 8.6 Hz, 1H), 7.50 (t, J = 2.7 Hz, 1H), 7.46 (d, J = 7.5 Hz, 1H), 7.39 (d, J = 8.3 Hz, 1H), 7.08 (dd, J = 5.4, 1.9 Hz, 1H), 6.62-6.53 (m, 1H). (ESI+) m/z 388 (M + H)⁺ Retention time = 3.51 mins (method 1) |
| 122 | 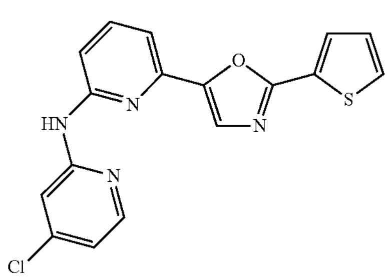 [SMILES: Clc1ccnc(Nc2cccc(-c3cnc(-c4cccs4)o3)n2)c1] | (4-Chloro-pyridin-2-yl)-[6-(2-thiophen-2-yl-oxazol-5-yl)-pyridin-2-yl]-amine | (400 MHz, DMSO) δ 10.18 (s, 1H), 8.38 (s, 1H), 8.24 (d, J = 5.4 Hz, 1H), 7.89-7.85 (m, 2H), 7.83-7.78 (m, 2H), 7.46 (d, J = 8.3 Hz, 1H), 7.42 (d, J = 7.5 Hz, 1H), 7.29 (t, J = 4.3 Hz, 1H), 7.05 (dd, J = 5.3, 1.5 Hz, 1H). (ESI+) m/z 355 (M + H)⁺ Retention time = 3.73 mins (method 1) |

TABLE 1-continued

| Ex # | Chemical structure | Name | ¹H NMR/LCMS |
|---|---|---|---|
| 123 | 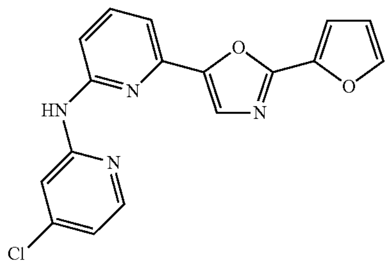 [SMILES: Clc1ccnc(Nc2cccc(-c3cnc(-c4ccco4)o3)n2)c1] | (4-Chloro-pyridin-2-yl)-[6-(2-furan-2-yl-oxazol-5-yl)-pyridin-2-yl]-amine | (400 MHz, DMSO) δ 10.19 (s, 1H), 8.31 (d, J = 1.6 Hz, 1H), 8.25 (d, J = 5.4 Hz, 1H), 8.02 (s, 1H), 7.85 (s, 1H), 7.82 (t, J = 7.9 Hz, 1H), 7.53 (d, J = 8.3 Hz, 1H), 7.41 (d, J = 7.5 Hz, 1H), 7.29 (d, J = 3.4 Hz, 1H), 7.05 (dd, J = 5.4, 1.8 Hz, 1H), 6.79 (dd, J = 3.4, 1.7 Hz, 1H). (ESI+) m/z 339 (M + H)+ Retention time = 3.27 mins (method 1) |
| 124 | 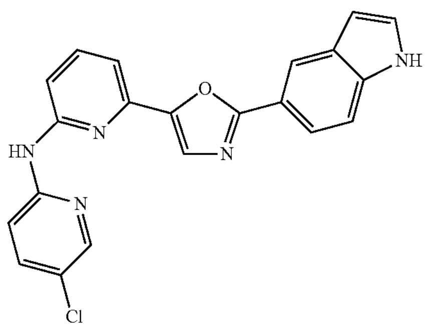 [SMILES: Clc1ccc(Nc2cccc(-c3cnc(-c4ccc5[nH]ccc5c4)o3)n2)nc1] | (5-Chloro-pyridin-2-yl)-{6-[2-(1H-indol-5-yl)-oxazol-5-yl]-pyridin-2-yl}-amine | (400 MHz, CDCl3) δ 11.48 (s, 1H), 10.08 (s, 1H), 8.37 (s, 1H), 8.29 (d, J = 2.6 Hz, 1H), 8.13 (d, J = 9.0 Hz, 1H), 7.91-7.85 (m, 3H), 7.84-7.78 (m, 1H), 7.58 (d, J = 8.5 Hz, 1H), 7.53 (d, J = 8.3 Hz, 1H), 7.51-7.48 (m, 1H), 7.43 (d, J = 7.4 Hz, 1H), 6.65-6.58 (m, 1H). (ESI+) m/z 388 (M + H)+ Retention time = 3.86 mins (method 1) |
| 125 | 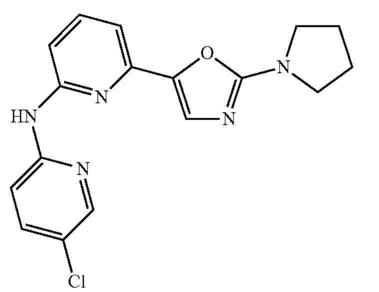 [SMILES: Clc1ccc(Nc2cccc(-c3cnc(N4CCCC4)o3)n2)nc1] | (5-Chloro-pyridin-2-yl)-[6-(2-pyrrolidin-1-yl-oxazol-5-yl)-pyridin-2-yl]-amine | (400 MHz, DMSO-d6) δ 9.88 (s, 1H), 8.25 (d, J = 2.6 Hz, 1H), 8.11 (d, J = 9.0 Hz, 1H), 7.81 (dd, J = 9.0, 2.7 Hz, 1H), 7.66 (t, J = 7.9 Hz, 1H), 7.44 (s, 1H), 7.31 (d, J = 8.3 Hz, 1H), 7.01 (d, J = 7.5 Hz, 1H), 3.51 (t, J = 6.6 Hz, 4H), 1.96 (t, J = 6.6 Hz, 4H). ESI+) m/z 342 (M + H)+ Retention time = 2.76 mins (method 1) |
| 126 | 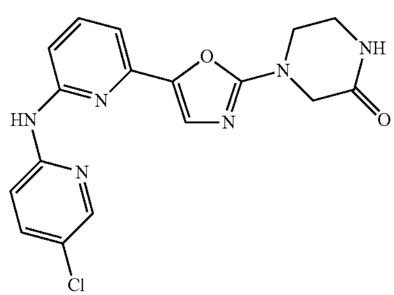 [SMILES: O=C1CN(c2ncc(-c3cccc(Nc4ccc(Cl)cn4)n3)o2)CCN1] | 4-{5-[6-(5-Chloro-pyridin-2-ylamino)-pyridin-2-yl]-oxazol-2-yl}-piperazine-2-one | (400 MHz, DMSO-d6) δ 9.95 (s, 1H), 8.26 (d, J = 2.6 Hz, 1H), 8.20 (s, 1H), 8.09 (d, J = 9.1 Hz, 1H), 7.81 (dd, J = 9.0, 2.7 Hz, 1H), 7.69 (t, J = 7.9 Hz, 1H), 7.50 (s, 1H), 7.36 (d, J = 8.3 Hz, 1H), 7.11 (d, J = 7.5 Hz, 1H), 4.07 (s, 2H), 3.74 (t, J = 5.3 Hz, 2H), 3.40-3.37 (m, 2H). (ESI+) m/z 371 (M + H)+ Retention time = 2.12 mins (method 1) |
| 127 | 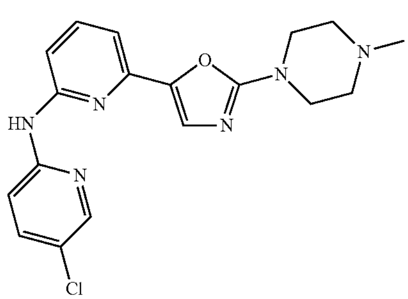 | (5-Chloro-pyridin-2-yl)-{6-[2-(4-methyl-piperazin-1-yl)-oxazol-5-yl]-pyridin-2-yl}-amine | (400 MHz, DMSO-d6) δ 9.88 (s, 1H), 8.24 (d, J = 2.6 Hz, 1H), 8.06 (d, J = 9.0 Hz, 1H), 7.80 (dd, J = 9.0, 2.7 Hz, 1H), 7.66 (t, J = 7.9 Hz, 1H), 7.45 (s, 1H), 7.34 (d, J = 8.3 Hz, 1H), 7.05 (d, J = 7.5 Hz, 1H), 3.52 (t, J = 4.9 Hz, 4H), 2.43 (t, J = 4.9 Hz, 4H), 2.23 (s, 3H). (ESI+) m/z 371 (M + H)+ Retention time = 1.89 mins (method 1) |

TABLE 1-continued

| Ex # | Chemical structure | Name | ¹H NMR/LCMS |
|---|---|---|---|
| 128 | 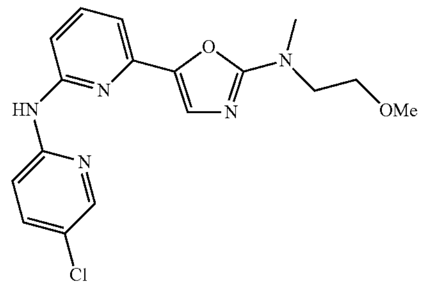 [SMILES: COCCN(C)c1ncc(-c2cccc(Nc3ccc(Cl)cn3)n2)o1] | (5-Chloro-pyridin-2-yl)-{6-[2-(2-methoxyethyl)-methyl-amino-oxazol-5-yl]-pyridin-2-yl}-amine | (400 MHz, DMSO-$d_6$) δ 9.87 (s, 1H), 8.24 (d, J = 2.6 Hz, 1H), 8.12 (d, J = 9.0 Hz, 1H), 7.79 (dd, J = 9.0, 2.7 Hz, 1H), 7.65 (t, J = 8.0 Hz, 1H), 7.42 (s, 1H), 7.29 (d, J = 8.3 Hz, 1H), 7.02 (d, J = 7.5 Hz, 1H), 3.63 (t, J = 5.0 Hz, 2H), 3.58 (t, J = 4.8 Hz, 2H), 3.28 (s, 3H), 3.12 (s, 3H). (ESI+) m/z 360 (M + H)⁺ Retention time = 2.67 mins (method 1) |
| 129 | 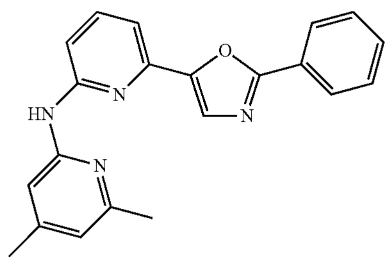 [SMILES: Cc1cc(C)nc(Nc2cccc(-c3cnc(-c4ccccc4)o3)n2)c1] | (4,6-Dimethyl-pyridin-2-yl)-[6-(2-phenyl-oxazol-5-yl)-pyridin-2-yl]-amine | (400 MHz, DMSO) δ 9.75 (s, 1H), 8.14-8.12 (m, 2H), 7.88 (s, 1H), 7.86 (s, 1H), 7.78-7.74 (m, 1H), 7.70-7.60 (m, 3H), 7.50 (d, J = 8.4 Hz, 1H), 7.39 (d, J = 7.4 Hz, 1H), 6.66 (s, 1H), 2.37 (s, 3H), 2.33 (s, 3H). (ESI+) m/z 343 (M + H)⁺ Retention time = 3.01 mins (method 1) |
| 130 | 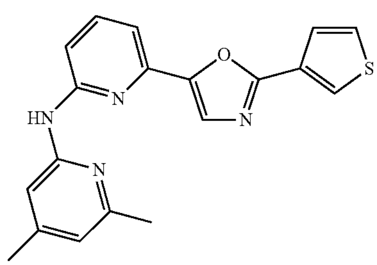 [SMILES: Cc1cc(C)nc(Nc2cccc(-c3cnc(-c4ccsc4)o3)n2)c1] | (4,6-Dimethyl-pyridin-2-yl)-[6-(2-thiophen-3-yl-oxazol-5-yl)-pyridin-2-yl]-amine | (400 MHz, DMSO-$d_6$) δ 9.73 (s, 1H), 8.31 (dd, J = 2.9, 1.1 Hz, 1H), 7.82-7.71 (m, 4H), 7.67 (dd, J = 5.1, 1.1 Hz, 1H), 7.53 (d, J = 8.3 Hz, 1H), 7.34 (d, J = 7.4 Hz, 1H), 6.64 (s, 1H), 2.36 (s, 3H), 2.31 (s, 3H). (ESI+) m/z 349 (M + H)⁺ Retention time = 2.82 mins (method 1) |
| 131 | 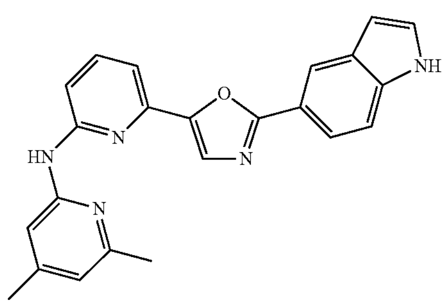 [SMILES: Cc1cc(C)nc(Nc2cccc(-c3cnc(-c4ccc5[nH]ccc5c4)o3)n2)c1] | (4,6-Dimethyl-pyridin-2-yl)-{6-[2-(1H-indol-5-yl)-oxazol-5-yl]-pyridin-2-yl}-amine | (400 MHz, DMSO-$d_6$) δ 11.45 (s, 1H), 9.70 (s, 1H), 8.37 (s, 1H), 7.94 (s, 1H), 7.89 (dd, J = 8.6, 1.6 Hz, 1H), 7.80 (s, 1H), 7.78-7.70 (m, 1H), 7.57 (d, J = 8.6 Hz, 1H), 7.51-7.48 (m, 1H), 7.46 (d, J = 8.4 Hz, 1H), 7.37 (d, J = 7.4 Hz, 1H), 6.67 (s, 1H), 6.62-6.55 (m, 1H), 2.38 (s, 3H), 2.37 (s, 3H). (ESI+) m/z 382 (M + H)⁺ Retention time = 2.82 mins (method 1) |
| 132 | 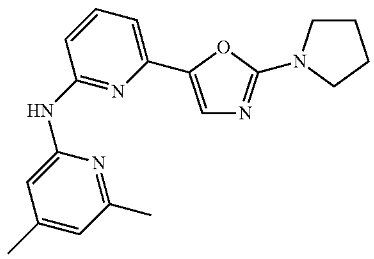 [SMILES: Cc1cc(C)nc(Nc2cccc(-c3cnc(N4CCCC4)o3)n2)c1] | (4,6-Dimethyl-pyridin-2-yl)-[6-(2-pyrrolidin-1-yl-oxazol-5-yl)-pyridin-2-yl]-amine | (400 MHz, DMSO-$d_6$) δ 9.53 (s, 1H), 7.81 (s, 1H), 7.60 (t, J = 7.9 Hz, 1H), 7.37 (s, 1H), 7.30 (d, J = 8.3 Hz, 1H), 6.96 (d, J = 7.5 Hz, 1H), 6.61 (s, 1H), 3.52 (t, J = 6.5 Hz, 4H), 2.35 (s, 3H), 2.27 (s, 3H), 2.01-1.92 (m, 4H). (ESI+) m/z 336 (M + H)⁺ Retention time = 2.34 mins (method 1) |

TABLE 1-continued

| Ex # | Chemical structure | Name | ¹H NMR/LCMS |
|---|---|---|---|
| 133 | 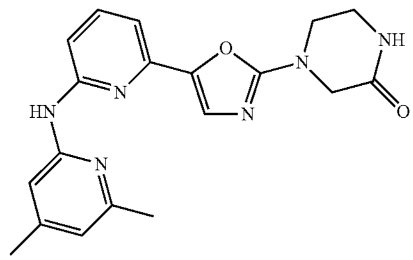 [SMILES: Cc1cc(C)nc(Nc2cccc(-c3cnc(N4CCNC(=O)C4)o3)n2)c1] | 4-{5-[6-(4,6-Dimethyl-pyridin-2-ylamino)-pyridin-2-yl]-oxazol-2-yl}-piperazine-2-one | (400 MHz, DMSO-$d_6$) δ 9.56 (s, 1H), 8.17 (s, 1H), 7.78 (s, 1H), 7.63 (t, J = 7.9 Hz, 1H), 7.42 (s, 1H), 7.34 (d, J = 8.3 Hz, 1H), 7.06 (d, J = 7.5 Hz, 1H), 6.62 (s, 1H), 4.08 (s, 2H), 3.74 (t, J = 5.4 Hz, 2H), 3.38-3.34 (m, 2H), 2.35 (s, 3H), 2.28 (s, 3H). (ESI+) m/z 365 (M + H)⁺ Retention time = 1.88 mins (method 1) |
| 134 | 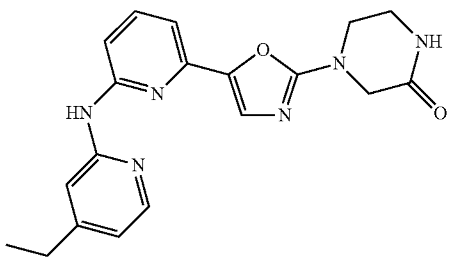 [SMILES: CCc1ccnc(Nc2cccc(-c3cnc(N4CCNC(=O)C4)o3)n2)c1] | 4-{5-[6-(4-Ethyl-pyridin-2-ylamino)-pyridin-2-yl]-oxazol-2-yl}-piperazine-2-one | (400 MHz, DMSO-$d_6$) δ 9.64 (s, 1H), 8.18 (s, 1H), 8.11 (d, J = 5.1 Hz, 1H), 7.90 (s, 1H), 7.65 (t, J = 8.0 Hz, 1H), 7.41-7.37 (m, 2H), 7.07 (d, J = 7.5 Hz, 1H), 6.77 (dd, J = 5.2, 0.9 Hz, 1H), 4.07 (s, 2H), 3.76-3.71 (m, 2H), 3.34 (s, 2H), 2.61 (q, J = 7.6 Hz, 2H), 1.22 (t, J = 7.6 Hz, 3H). (ESI+) m/z 365 (M + H)⁺ Retention time = 2.02 mins (method 1) |
| 135 | 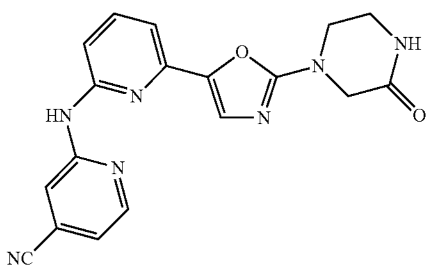 [SMILES: N#Cc1ccnc(Nc2cccc(-c3cnc(N4CCNC(=O)C4)o3)n2)c1] | 2-{6-[2-(3-Oxo-piperazin-1-yl)-oxazol-5-yl]-pyridin-2-ylamino}-isonicotinonitrile | (400 MHz, DMSO-$d_6$) δ 10.23 (s, 1H), 8.58 (s, 1H), 8.47 (d, J = 5.0 Hz, 1H), 8.16 (s, 1H), 7.72 (t, J = 7.9 Hz, 1H), 7.48 (s, 1H), 7.35-7.23 (m, 2H), 7.19 (d, J = 7.6 Hz, 1H), 4.06 (s, 2H), 3.88-3.63 (m, 2H), 3.42-3.33 (m, 2H). (ESI+) m/z 362 (M + H)⁺ Retention time = 2.23 mins (method 1) |
| 136 | 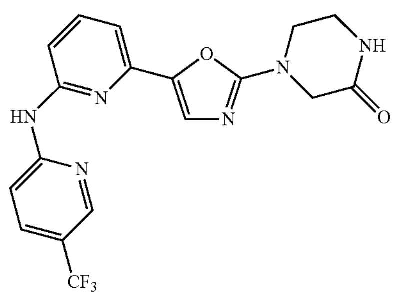 [SMILES: O=C1CN(c2ncc(-c3cccc(Nc4ccc(C(F)(F)F)cn4)n3)o2)CCN1] | 4-{5-[6-(5-Trifluoromethyl-pyridin-2-ylamino)-pyridin-2-yl]-oxazol-2-yl}-piperazine-2-one | (400 MHz, DMSO $d_6$) δ 10.27 (s, 1H), 8.59 (s, 1H), 8.21-8.13 (m, 2H), 8.06 (dd, J = 9.0, 2.1 Hz, 1H), 7.74 (t, J = 8.0 Hz, 1H), 7.53 (s, 1H), 7.47 (d, J = 8.3 Hz, 1H), 7.18 (d, J = 7.5 Hz, 1H), 4.08 (s, 2H), 3.75 (t, J = 5.2 Hz, 2H), 3.40-3.33 (m, 2H). (ESI+) m/z 405 (M + H)⁺ Retention time = 2.71 mins (method 1) |
| 137 | 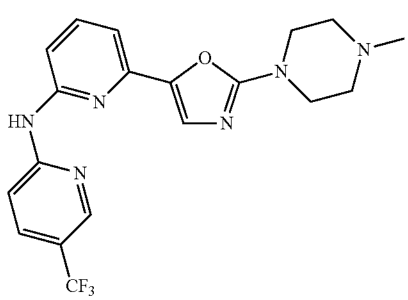 [SMILES: CN1CCN(c2ncc(-c3cccc(Nc4ccc(C(F)(F)F)cn4)n3)o2)CC1] | 4-{5-[6-(5-Trifluoromethyl-pyridin-2-ylamino)-pyridin-2-yl]-oxazol-2-yl}-piperazin-2-one | (400 MHz, DMSO-$d_6$) δ 10.24 (s, 1H), 8.58 (s, 1H), 8.15 (d, J = 8.9 Hz, 1H), 8.05 (dd, J = 8.9, 2.4 Hz, 1H), 7.72 (t, J = 7.9 Hz, 1H), 7.49 (s, 1H), 7.45 (d, J = 8.3 Hz, 1H), 7.12 (d, J = 7.5 Hz, 1H), 3.56-3.51 (m, 4H), 2.45-2.41 (m, 4H), 2.23 (s, 3H). (ESI+) m/z 405 (M + H)⁺ Retention time = 2.45 mins (method 1) |

TABLE 1-continued

| Ex # | Chemical structure | Name | ¹H NMR/LCMS |
|---|---|---|---|
| 138 | 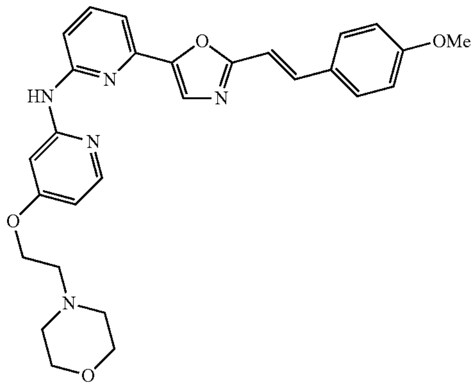 [SMILES: COc1ccc(/C=C/c2ncc(-c3cccc(Nc4cc(OCCN5CCOCC5)ccn4)n3)o2)cc1] | (6-{2-[2-(4-Methoxy-phenyl)-vinyl]-oxazol-5-yl}-pyridin-2-yl)-[4-(2-morpholin-4-yl-ethoxy)-pyridin-2-yl]-amine | (400 MHz, DMSO-d$_6$) δ 9.75 (s, 1H), 8.06 (d, J = 5.8 Hz, 1H), 7.80-7.68 (m, 5H), 7.61 (d, J = 16.3 Hz, 1H), 7.53 (d, J = 8.4 Hz, 1H), 7.33 (d, J = 7.4 Hz, 1H), 7.14-6.86 (m, 3H), 6.56 (dd, J = 5.8, 2.0 Hz, 1H), 4.22 (t, J = 5.7 Hz, 2H), 3.81 (s, 3H), 3.56 (t, J = 4.6 Hz, 4H), 2.71 (t, J = 5.7 Hz, 2H), 2.49-2.42 (m, 4H). (ESI+) m/z 500 (M + H)⁺ Retention time = 2.47 mins (method 1) |
| 139 | 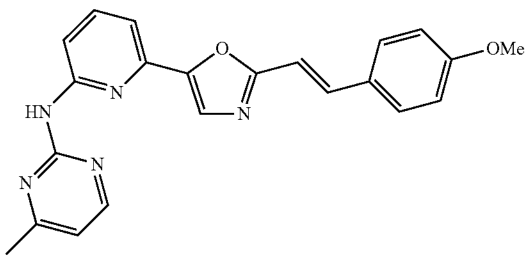 [SMILES: COc1ccc(/C=C/c2ncc(-c3cccc(Nc4nccc(C)n4)n3)o2)cc1] | (6-{2-[2-(4-Methoxy-phenyl)-vinyl]-oxazol-5-yl}-pyridin-2-yl)-(4-methyl-pyrimidin-2-yl)-amine | (300 MHz, DMSO-d$_6$) δ 9.64 (s, 1H), 8.43 (d, J = 4.5 Hz, 1H), 8.28 (d, J = 8.2 Hz, 1H), 7.92-7.83 (m, 1H), 7.79-7.66 (m, 3H), 7.62 (d, J = 16.6 Hz, 1H), 7.44 (d, J = 7.5 Hz, 1H), 7.07 (d, J = 16.5 Hz, 1H), 7.00 (d, J = 8.5 Hz, 2H), 6.88 (d, J = 5.1 Hz, 1H), 3.81 (s, 3H), 2.42 (s, 3H). (ESI+) m/z 386 (M + H)⁺ Retention time = 3.93 mins (method 1) |
| 140 | 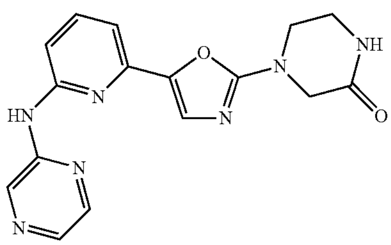 [SMILES: O=C1CN(c2ncc(-c3cccc(Nc4cnccn4)n3)o2)CCN1] | 4-{5-[6-(Pyrazin-2-ylamino)-pyridin-2-yl]-oxazol-2-yl}-piperazine-2-one | (400 MHz, DMSO-d$_6$) δ 10.08 (s, 1H), 9.18 (s, 1H), 8.26 (s, 1H), 8.18 (s, 1H), 8.12 (d, J = 2.6 Hz, 1H), 7.74 (t, J = 7.9 Hz, 1H), 7.53 (d, J = 8.3 Hz, 1H), 7.45 (s, 1H), 7.18 (d, J = 7.6 Hz, 1H), 4.08 (s, 2H), 3.81-3.65 (m, 2H), 3.42-3.33 (m, 2H). (ESI+) m/z 338 (M + H)⁺ Retention time = 1.81 mins (method 1) |
| 141 | 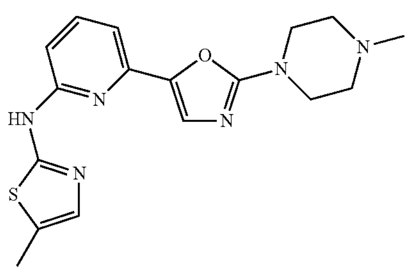 [SMILES: Cc1cnc(Nc2cccc(-c3cnc(N4CCN(C)CC4)o3)n2)s1] | {6-[2-(4-Methyl-piperazin-1-yl)-oxazol-5-yl]-pyridin-2-yl}-(5-methyl-thiazol-2-yl)-amine | (400 MHz, DMSO-d$_6$) δ 10.96 (s, 1H), 7.66 (t, J = 7.9 Hz, 1H), 7.54 (s, 1H), 7.06-7.01 (m, 2H), 6.83 (d, J = 8.2 Hz, 1H), 3.57 (dd, J = 5.9, 3.8 Hz, 4H), 2.45 (d, J = 4.9 Hz, 4H), 2.36 (s, 3H), 2.25 (s, 3H). (ESI+) m/z 357 (M + H)⁺ Retention time = 1.53 mins (method 1) |
| 142 | 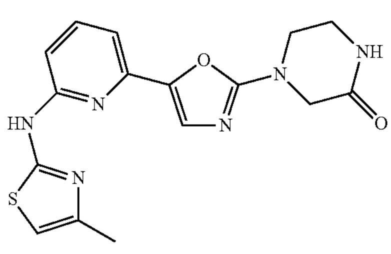 [SMILES: Cc1csc(Nc2cccc(-c3cnc(N4CCNC(=O)C4)o3)n2)n1] | 4-{5-[6-(4-Methyl-thiazol-2-ylamino)-pyridin-2-yl]-oxazol-2-yl}-piperazine-2-one | (400 MHz, CDCl3) δ 11.28 (s, 1H), 8.17 (s, 1H), 7.70 (t, J = 7.9 Hz, 1H), 7.56 (s, 1H), 7.09 (d, J = 7.5 Hz, 1H), 6.83 (d, J = 8.2 Hz, 1H), 6.58 (s, 1H), 4.09 (s, 2H), 3.80-3.68 (m, 2H), 3.43-3.34 (m, 2H), 2.26 (s, 3H). (ESI+) m/z 357 (M + H)⁺ Retention time = 1.98 mins (method 1) |

TABLE 1-continued

| Ex # | Chemical structure | Name | ¹H NMR/LCMS |
|------|-------------------|------|-------------|
| 143 | 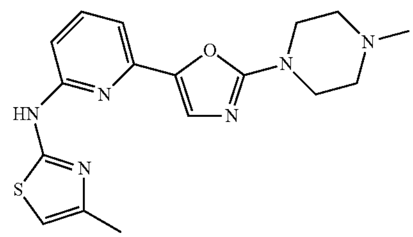 [SMILES: Cc1csc(Nc2cccc(-c3cnc(N4CCN(C)CC4)o3)n2)n1] | {6-[2-(4-Methyl-piperazin-1-yl)-oxazol-5-yl]-pyridin-2-yl}-(4-methyl-thiazol-2-yl)-amine | (400 MHz, DMSO-$d_6$) δ 11.27 (s, 1H), 7.68 (t, J = 7.9 Hz, 1H), 7.52 (s, 1H), 7.04 (d, J = 7.5 Hz, 1H), 6.81 (d, J = 8.2 Hz, 1H), 6.59 (s, 1H), 3.54 (t, J = 4.6 Hz, 4H), 2.43 (t, J = 4.6 Hz, 4H), 2.25 (s, 3H), 2.23 (s, 3H).<br>(ESI+) m/z 357 (M + H)⁺<br>Retention time = 1.53 mins (method 1) |
| 144 | 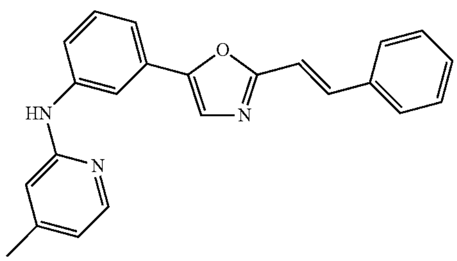 [SMILES: Cc1ccnc(Nc2cccc(-c3cnc(/C=C/c4ccccc4)o3)c2)c1] | (4-Methyl-pyridin-2-yl)-[3-(2-styryl-oxazol-5-yl)-phenyl]-amine | (360 MHz, DMSO-$d_6$) δ 9.09 (s, 1H), 8.09-8.05 (m, 2H), 7.77-7.72 (m, 3H), 7.69 (s, 1H), 7.58 (d, J = 16.4 Hz, 1H), 7.48-7.26 (m, 5H), 7.21 (d, J = 16.4 Hz, 1H), 6.68 (s, 1H), 6.64 (d, J = 5.1 Hz, 1H), 2.25 (s, 3H).<br>(ESI+) m/z 354 (M + H)⁺<br>Retention time = 3.35 mins (method 1) |
| 145 | 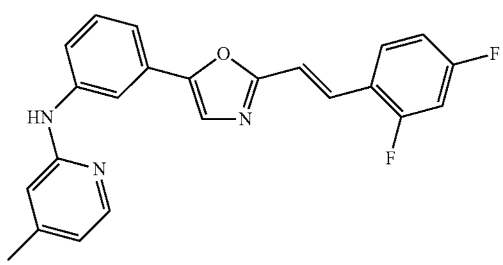 [SMILES: Cc1ccnc(Nc2cccc(-c3cnc(/C=C/c4ccc(F)cc4F)o3)c2)c1] | (3-{2-[2-(2,4-Difluoro-phenyl)-vinyl]-oxazol-5-yl}-phenyl)-(4-methyl-pyridin-2-yl)-amine | (400 MHz, DMSO-$d_6$) δ 9.14 (s, 1H), 8.11-8.01 (m, 3H), 7.77-7.72 (m, 2H), 7.59 (d, J = 16.5 Hz, 1H), 7.43-7.29 (m, 3H), 7.27 (d, J = 16.4 Hz, 1H), 7.20 (td, J = 8.5, 2.2 Hz, 1H), 6.68 (s, 1H), 6.64 (d, J = 5.2 Hz, 1H), 2.25 (s, 3H).<br>(ESI+) m/z 390 (M + H)⁺<br>Retention time = 3.51 mins (method 1) |
| 146 | 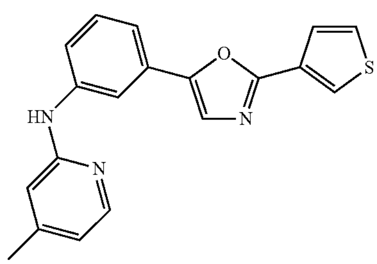 [SMILES: Cc1ccnc(Nc2cccc(-c3cnc(-c4ccsc4)o3)c2)c1] | (4-Methyl-pyridin-2-yl)-[3-(2-thiophen-3-yl-oxazol-5-yl)-phenyl]-amine | (400 MHz, DMSO-$d_6$) δ 9.12 (s, 1H), 8.24 (s, 1H), 8.15-8.03 (m, 2H), 7.80-7.76 (m, 1H), 7.73 (d, J = 7.7 Hz, 1H), 7.69-7.67 (m, 1H), 7.65-7.62 (m, 1H), 7.39-7.29 (m, 2H), 6.67 (s, 1H), 6.64 (s, 1H), 2.25 (s, 3H).<br>(ESI+) m/z 334 (M + H)⁺<br>Retention time = 2.89 mins (method 1) |
| 147 | 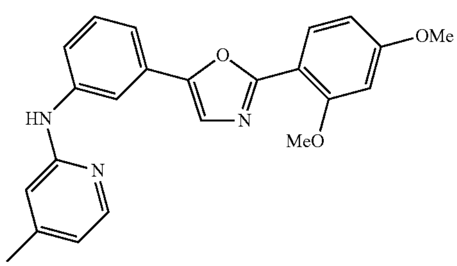 [SMILES: COc1ccc(-c2ncc(-c3cccc(Nc4cc(C)ccn4)c3)o2)c(OC)c1] | {3-[2-(2,4-Dimethoxy-phenyl)-oxazol-5-yl]-phenyl}-(4-methyl-pyridin-2-yl)-amine | (400 MHz, DMSO-$d_6$) δ 9.11 (s, 1H), 8.09-8.04 (m, 2H), 7.87 (d, J = 8.7 Hz, 1H), 7.69 (d, J = 7.8 Hz, 1H), 7.65 (s, 1H), 7.34 (t, J = 7.8 Hz, 1H), 7.27 (d, J = 7.5 Hz, 1H), 6.77-6.66 (m, 3H), 6.64 (d, J = 5.1 Hz, 1H), 3.94 (s, 3H), 3.86 (s, 3H), 2.25 (s, 3H).<br>(ESI+) m/z 388 (M + H)⁺<br>Retention time = 2.95 mins (method 1) |
| 148 | 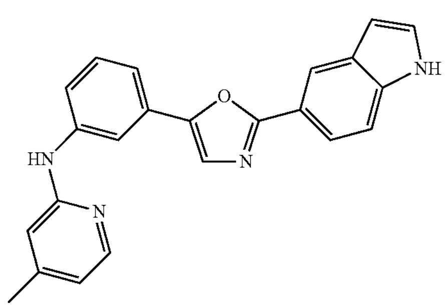 [SMILES: Cc1ccnc(Nc2cccc(-c3cnc(-c4ccc5[nH]ccc5c4)o3)c2)c1] | {3-[2-(1H-Indol-5-yl)-oxazol-5-yl]-phenyl}-(4-methyl-pyridin-2-yl)-amine | (400 MHz, DMSO) δ 11.43 (s, 1H), 9.11 (s, 1H), 8.30 (s, 1H), 8.09 (d, J = 5.2 Hz, 1H), 8.05 (s, 1H), 7.85-7.78 (m, 2H), 7.67 (s, 1H), 7.56 (d, J = 8.5 Hz, 1H), 7.47 (t, J = 2.6 Hz, 1H), 7.39-7.31 (m, 2H), 6.69 (s, 1H), 6.64 (d, J = 5.2 Hz, 1H), 6.61 (s, 1H), 2.26 (s, 3H).<br>(ESI+) m/z 367 (M + H)⁺<br>Retention time = 2.82 mins (method 1) |

TABLE 1-continued

| Ex # | Chemical structure | Name | ¹H NMR/LCMS |
|---|---|---|---|
| 149 | 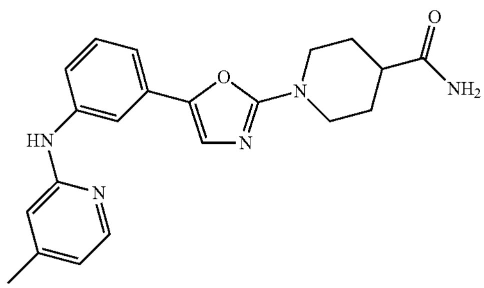 [SMILES: Cc1ccnc(Nc2cccc(-c3cnc(N4CCC(C(N)=O)CC4)o3)c2)c1] | 1-{5-[3-(4-Methyl-pyridin-2-ylamino)-phenyl]-oxazol-2-yl}-piperidine-4-carboxylic acid amide | (300 MHz, DMSO-$d_6$) δ 8.98 (s, 1H), 8.03 (d, J = 5.1 Hz, 1H), 7.73 (s, 1H), 7.65 (d, J = 9.1 Hz, 1H), 7.32 (s, 1H), 7.28-7.18 (m, 2H), 7.05 (d, J = 7.7 Hz, 1H), 6.83 (s, 1H), 6.64 (s, 1H), 6.60 (d, J = 5.0 Hz, 1H), 4.02 (d, J = 13.0 Hz, 2H), 3.02 (t, J = 11.3 Hz, 2H), 2.33 (t, J = 12.0 Hz, 1H), 2.23 (s, 3H), 1.87-1.70 (m, J = 11.3 Hz, 2H), 1.69-1.44 (m, 2H). (ESI+) m/z 378 (M + H)⁺ |
| 150 | 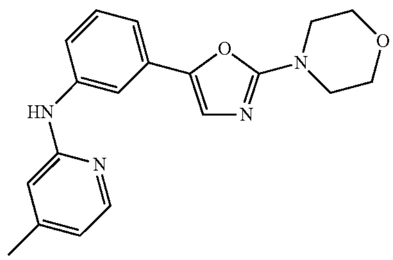 [SMILES: Cc1ccnc(Nc2cccc(-c3cnc(N4CCOCC4)o3)c2)c1] | (4-Methyl-pyridin-2-yl)-[3-(2-morpholin-4-yl-oxazol-5-yl)-phenyl]-amine | (300 MHz, DMSO-$d_6$) δ 8.97 (s, 1H), 8.03 (d, J = 5.2 Hz, 1H), 7.78 (s, 1H), 7.62 (d, J = 7.1 Hz, 1H), 7.28-7.21 (m, 2H), 7.06 (d, J = 7.8 Hz, 1H), 6.64 (s, 1H), 6.60 (d, J = 5.4 Hz, 1H), 3.72 (t, J = 4.6 Hz, 4H), 3.46 (t, J = 4.6 Hz, 4H), 2.23 (s, 3H). (ESI+) m/z 337 (M + H)⁺ |
| 151 | 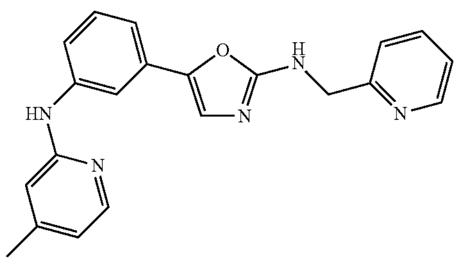 [SMILES: Cc1ccnc(Nc2cccc(-c3cnc(NCc4ccccn4)o3)c2)c1] | (4-Methyl-pyridin-2-yl)-(3-{2-[(pyridin-2-ylmethyl)-amino]-oxazol-5-yl}-phenyl)-amine | (400 MHz, DMSO-$d_6$) δ 8.96 (s, 1H), 8.52 (d, J = 4.6 Hz, 1H), 8.06-7.97 (m, 2H), 7.80-7.72 (m, 2H), 7.54 (d, J = 8.0 Hz, 1H), 7.40 (d, J = 7.8 Hz, 1H), 7.30-7.20 (m, 2H), 7.12 (s, 1H), 7.00 (d, J = 7.7 Hz, 1H), 6.65 (s, 1H), 6.60 (d, J = 5.2 Hz, 1H), 4.52 (d, J = 6.2 Hz, 2H), 4.33 (t, J = 5.1 Hz, 1H), 2.23 (s, 3H). (ESI+) m/z 358 (M + H)⁺ Retention time = 1.69 mins (method 1) |
| 152 | 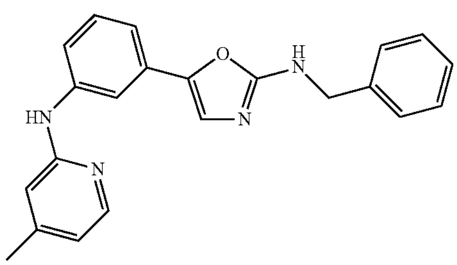 [SMILES: Cc1ccnc(Nc2cccc(-c3cnc(NCc4ccccc4)o3)c2)c1] | [3-(2-Benzylamino-oxazol-5-yl)-phenyl]-(4-methyl-pyridin-2-yl)-amine | (400 MHz, DMSO-$d_6$) δ 8.99 (s, 1H), 8.02 (d, J = 5.2 Hz, 1H), 7.98 (t, J = 6.3 Hz, 1H), 7.78 (s, 1H), 7.53 (d, J = 8.0 Hz, 1H), 7.41-7.28 (m, 4H), 7.24 (dd, J = 14.8, 7.3 Hz, 2H), 7.13 (s, 1H), 7.00 (d, J = 7.8 Hz, 1H), 6.64 (s, 1H), 6.60 (d, J = 5.3 Hz, 1H), 4.41 (d, J = 6.2 Hz, 2H), 2.23 (s, 3H). (ESI+) m/z 357 (M + H)⁺ Retention time = 2.47 mins (method 1) |
| 153 | 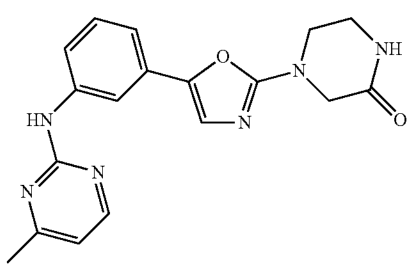 | 4-{5-[3-(4-Methyl-pyrimidin-2-ylamino)-phenyl]-oxazol-2-yl}-piperazine-2-one | (400 MHz, DMSO-$d_6$) δ 9.59 (s, 1H), 8.35 (d, J = 5.0 Hz, 1H), 8.17 (s, 1H), 8.11 (s, 1H), 7.64 (d, J = 8.0 Hz, 1H), 7.35-7.21 (m, 2H), 7.15 (d, J = 7.7 Hz, 1H), 6.76 (d, J = 5.0 Hz, 1H), 4.03 (s, 2H), 3.76-3.62 (m, 2H), 3.40-3.34 (m, 2H), 2.38 (s, 3H). (ESI+) m/z 351 (M + H)⁺ Retention time = 2.52 mins (method 1) |
| 154 | 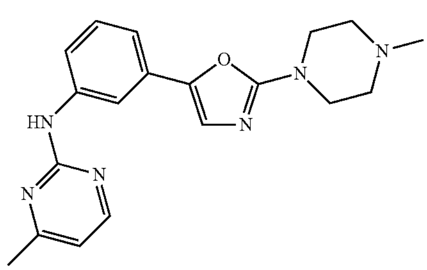 | {3-[2-(4-Methyl-piperazin-1-yl)-oxazol-5-yl]-phenyl}-(4-methyl-pyrimidin-2-yl)-amine | (400 MHz, DMSO-$d_6$) δ 9.58 (s, 1H), 8.35 (d, J = 5.0 Hz, 1H), 8.10 (s, 1H), 7.61 (d, J = 8.0 Hz, 1H), 7.27 (t, J = 8.0 Hz, 1H), 7.23 (s, 1H), 7.12 (d, J = 7.7 Hz, 1H), 6.76 (d, J = 5.0 Hz, 1H), 3.59-3.41 (m, 4H), 2.47-2.39 (m, 4H), 2.37 (s, 3H), 2.23 (s, 3H). (ESI+) m/z 351 (M + H)⁺ Retention time = 2.18 mins (method 1) |

TABLE 1-continued

| Ex # | Chemical structure | Name | ¹H NMR/LCMS |
|---|---|---|---|
| 155 | 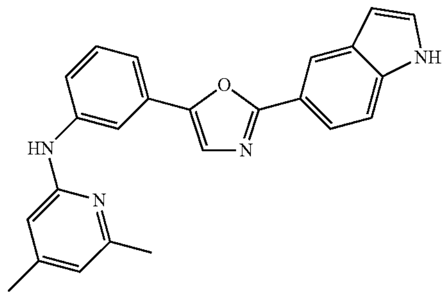 [SMILES: Cc1cc(C)nc(Nc2cccc(-c3cnc(-c4ccc5[nH]ccc5c4)o3)c2)c1] | (4,6-Dimethyl-pyridin-2-yl)-{3-[2-(1H-indol-5-yl)-oxazol-5-yl]-phenyl}-amine | (400 MHz, DMSO-d$_6$) δ 11.32 (s, 1H), 8.92 (s, 1H), 8.41 (s, 1H), 8.31 (s, 1H), 7.84 (dd, J = 8.5, 1.5 Hz, 1H), 7.63-7.57 (m, 2H), 7.55 (d, J = 8.5 Hz, 1H), 7.45 (s, 1H), 7.40-7.28 (m, 2H), 6.58 (d, J = 2.8 Hz, 1H), 6.52 (d, J = 3.7 Hz, 2H), 2.44 (s, 3H), 2.22 (s, 3H). (ESI+) m/z 381 (M + H)$^+$ Retention time = 2.97 mins (method 1) |
| 156 | 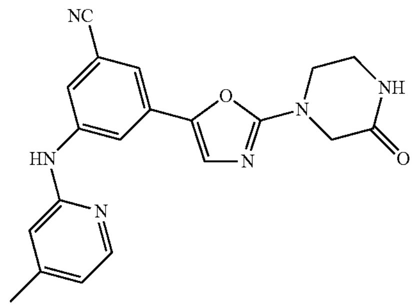 [SMILES: Cc1ccnc(Nc2cc(C#N)cc(-c3cnc(N4CCNC(=O)C4)o3)c2)c1] | 3-(4-Methyl-pyridin-2-ylamino)-5-[2-(3-oxo-piperazin-1-yl)-oxazol-5-yl]-benzonitrile | (400 MHz, DMSO-d$_6$) δ 9.31 (s, 1H), 8.22 (s, 1H), 8.12 (d, J = 5.1 Hz, 1H), 8.06 (s, 1H), 7.92 (s, 1H), 7.54 (s, 1H), 7.45 (s, 1H), 6.74-6.68 (m, 2H), 4.08 (s, 2H), 3.74 (t, J = 5.4 Hz, 2H), 3.40-3.34 (m, 2H), 2.28 (s, 3H). (ESI+) m/z 375 (M + H)$^+$ Retention time = 2.09 mins (method 1) |
| 157 | 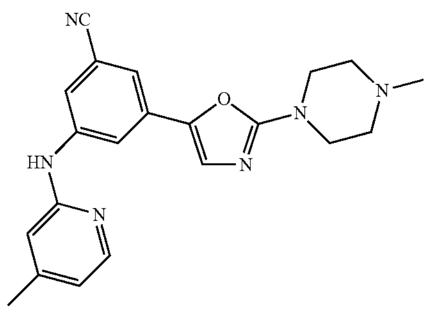 | 3-[2-(4-Methyl-piperazin-1-yl)-oxazol-5-yl]-5-(4-methyl-pyridin-2-ylamino)-benzonitrile | (400 MHz, DMSO-d$_6$) δ 9.38 (s, 1H), 8.23 (t, J = 1.7 Hz, 1H), 8.11 (d, J = 5.2 Hz, 1H), 7.87 (t, J = 1.7 Hz, 1H), 7.52 (t, J = 1.3 Hz, 1H), 7.43 (s, 1H), 6.70 (d, J = 5.3 Hz, 1H), 6.67 (s, 1H), 3.54-3.49 (m, 4H), 2.45-2.39 (m, 4H), 2.26 (s, 3H), 2.23 (s, 3H). (ESI+) m/z 375 (M + H)$^+$ Retention time = 1.78 mins (method 1) |
| 158 | 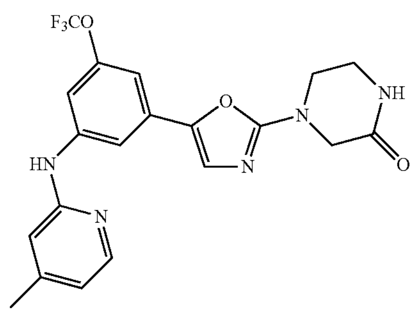 [SMILES: Cc1ccnc(Nc2cc(OC(F)(F)F)cc(-c3cnc(N4CCNC(=O)C4)o3)c2)c1] | 4-{5-[3-(4-Methyl-pyridin-2-ylamino)-5-trifluoromethoxy-phenyl]-oxazol-2-yl}-piperazin-2-one | (400 MHz, DMSO-d$_6$) δ 9.35 (s, 1H), 8.16 (s, 1H), 8.09 (d, J = 5.1 Hz, 1H), 7.94 (s, 1H), 7.65 (s, 1H), 7.43 (s, 1H), 7.04 (s, 1H), 6.70-6.66 (m, 2H), 4.06 (s, 2H), 3.71 (t, J = 5.2 Hz, 2H), 3.40-3.34 (m, 2H), 2.26 (s, 3H). (ESI+) m/z 434 (M + H)$^+$ Retention time = 2.74 mins (method 1) |
| 159 | 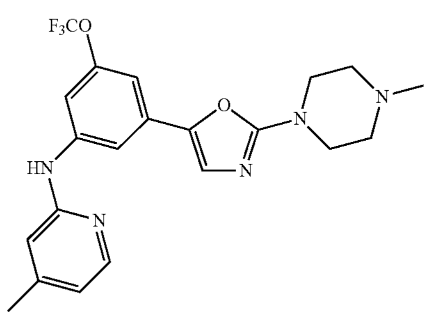 | {3-[2-(4-Methyl-piperazin-1-yl)-oxazol-5-yl]-5-trifluoromethoxy-phenyl}-(4-methyl-pyridin-2-yl)-amine | (400 MHz, DMSO) δ 9.32 (s, 1H), 8.08 (d, J = 5.1 Hz, 1H), 7.91 (s, 1H), 7.63 (s, 1H), 7.38 (s, 1H), 7.00 (s, 1H), 6.70-6.65 (m, 2H), 3.50 (t, J = 4.9 Hz, 4H), 2.43 (t, J = 4.9 Hz, 4H), 2.25 (s, 3H), 2.23 (s, 3H). (ESI+) m/z 434 (M + H)$^+$ Retention time = 2.36 mins (method 1) |

TABLE 1-continued

| Ex # | Chemical structure | Name | ¹H NMR/LCMS |
|---|---|---|---|
| 160 | 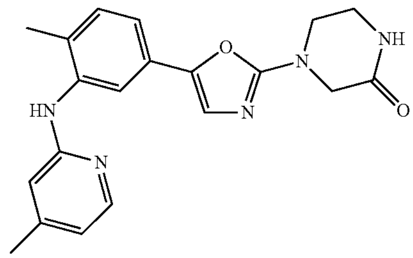 [SMILES: Cc1ccnc(Nc2cc(-c3cnc(N4CCNC(=O)C4)o3)ccc2C)c1] | 4-{5-[4-Methyl-3-(4-methyl-pyridin-2-ylamino)-phenyl]-oxazol-2-yl}-piperazin-2-one | (400 MHz, DMSO-d$_6$) δ 8.03-7.91 (m, 3H), 7.73 (s, 1H), 7.24-7.19 (m, 3H), 6.54 (s, 2H), 4.00 (s, 2H), 3.82-3.54 (m, 2H), 3.40-3.30 (m, 2H), 2.20 (s, 6H).<br>(ESI+) m/z 364 (M + H)$^+$<br>Retention time = 1.94 mins (method 1) |
| 161 | 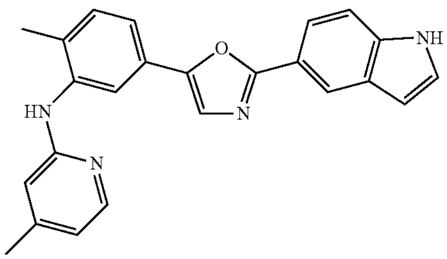 [SMILES: Cc1ccnc(Nc2cc(-c3cnc(-c4ccc5[nH]ccc5c4)o3)ccc2C)c1] | {5-[2-(1H-Indol-5-yl)-oxazol-5-yl]-2-methyl-phenyl}-(4-methyl-pyridin-2-yl)-amine | (400 MHz, DMSO-d$_6$) δ 11.39 (s, 1H), 8.28 (s, 1H), 8.14 (s, 1H), 8.01 (d, J = 1.4 Hz, 1H), 7.97 (d, J = 5.1 Hz, 1H), 7.81 (dd, J = 8.6, 1.5 Hz, 1H), 7.64 (s, 1H), 7.53 (d, J = 8.5 Hz, 1H), 7.45 (dd, J = 5.5, 2.4 Hz, 2H), 7.32 (d, J = 7.9 Hz, 1H), 6.62-6.56 (m, 3H), 2.25 (s, 3H), 2.22 (s, 3H).<br>(ESI+) m/z 381 (M + H)$^+$<br>Retention time = 2.95 mins (method 1) |
| 162 | 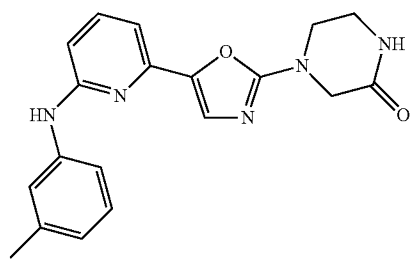 [SMILES: Cc1cccc(Nc2cccc(-c3cnc(N4CCNC(=O)C4)o3)n2)c1] | 4-[5-(6-m-Tolylamino-pyridin-2-yl)-oxazol-2-yl]-piperazine-2-one | (400 MHz, DMSO-d$_6$) δ 9.02 (t, J = 5.4 Hz, 1H), 8.15 (s, 1H), 7.69 (s, 1H), 7.57 (t, J = 7.8 Hz, 1H), 7.51 (d, J = 8.1 Hz, 1H), 7.38 (s, 1H), 7.17 (t, J = 7.8 Hz, 1H), 6.95 (d, J = 7.4 Hz, 1H), 6.73 (d, J = 7.4 Hz, 1H), 6.67 (d, J = 8.3 Hz, 1H), 4.07 (s, 2H), 3.74 (t, J = 5.4 Hz, 2H), 3.36 (t, J = 6.5 Hz, 2H), 2.31 (s, 3H).<br>(ESI+) m/z 350 (M + H)$^+$<br>Retention time = 3.03 mins (method 1) |
| 163 | 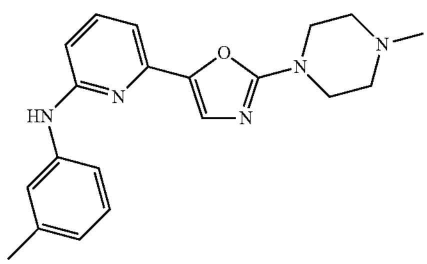 | {6-[2-(4-Methyl-piperazin-1-yl)-oxazol-5-yl]-pyridin-2-yl}-m-tolylamine | (400 MHz, DMSO-d$_6$) δ 9.01 (s, 1H), 7.72 (s, 1H), 7.55 (t, J = 7.9 Hz, 1H), 7.48 (d, J = 8.0 Hz, 1H), 7.35 (s, 1H), 7.16 (t, J = 7.8 Hz, 1H), 6.91 (d, J = 7.4 Hz, 1H), 6.72 (d, J = 7.4 Hz, 1H), 6.65 (d, J = 8.3 Hz, 1H), 3.53 (t, J = 5.0 Hz, 4H), 2.43 (t, J = 5.0 Hz, 4H), 2.30 (s, 3H), 2.24 (s, 3H).<br>(ESI+) m/z 350 (M + H)$^+$<br>Retention time = 2.65 mins (method 1) |
| 164 | 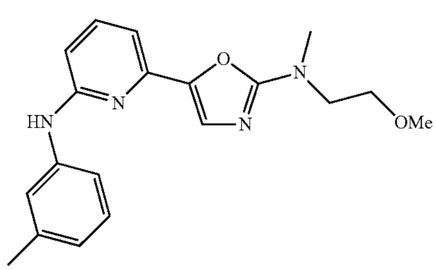 [SMILES: COCCN(C)c1ncc(-c2cccc(Nc3cccc(C)c3)n2)o1] | (6-{2-[(2-Methoxy-ethyl)-methyl-amino]-oxazol-5-yl}-pyridin-2-yl)-m-tolylamine | (400 MHz, DMSO-d$_6$) δ 8.99 (s, 1H), 7.67 (s, 1H), 7.54 (t, J = 7.9 Hz, 2H), 7.32 (s, 1H), 7.16 (t, J = 7.8 Hz, 1H), 6.87 (d, J = 7.4 Hz, 1H), 6.72 (d, J = 7.4 Hz, 1H), 6.63 (d, J = 8.3 Hz, 1H), 3.61 (dd, J = 17.1, 4.8 Hz, 4H), 3.28 (s, 4H), 3.12 (s, 3H), 2.30 (s, 3H).<br>(ESI+) m/z 339 (M + H)$^+$<br>Retention time = 3.50 mins (method 1) |
| 165 | 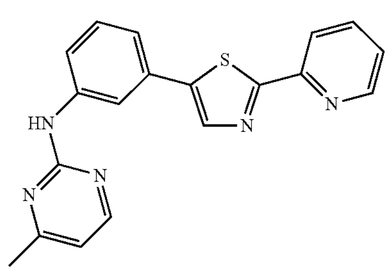 [SMILES: Cc1ccnc(Nc2cccc(-c3cnc(-c4ccccn4)s3)c2)n1] | (4-Methyl-pyrimidin-2-yl)-[3-(2-pyridin-2-yl-thiazol-5-yl)-phenyl]-amine | (300 MHz, DMSO) δ 9.74 (s, 1H), 8.68 (d, J = 4.7 Hz, 1H), 8.40 (d, J = 5.0 Hz, 1H), 8.31 (s, 1H), 8.29 (s, 1H), 8.16 (d, J = 7.9 Hz, 1H), 8.00 (t, J = 7.0 Hz, 1H), 7.80 (d, J = 6.6 Hz, 1H), 7.55-7.48 (m, 1H), 7.45-7.33 (m, 2H), 6.80 (d, J = 5.0 Hz, 1H), 2.41 (s, 3H).<br>(APCI+) m/z 346.1 (M + H).<br>Retention time: 3.71 mins (method 2) |

TABLE 1-continued

| Ex # | Chemical structure | Name | ¹H NMR/LCMS |
|---|---|---|---|
| 166 | 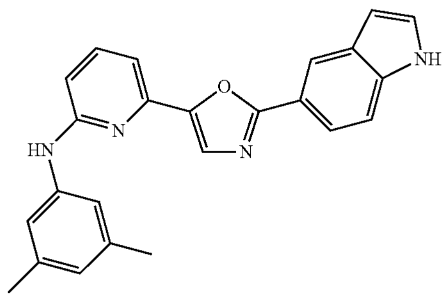 [SMILES: Cc1cc(C)cc(Nc2cccc(-c3cnc(-c4ccc5[nH]ccc5c4)o3)n2)c1] | (3,5-Dimethyl-phenyl)-{6-[2-(1H-indol-5-yl)-oxazol-5-yl]-pyridin-2-yl}-amine | (400 MHz, DMSO-$d_6$) δ 11.43 (s, 1H), 9.07 (s, 1H), 8.37 (s, 1H), 7.89 (dd, J = 8.6, 1.6 Hz, 1H), 7.74 (s, 1H), 7.67 (t, J = 7.8 Hz, 1H), 7.56 (d, J = 8.5 Hz, 1H), 7.52 (s, 2H), 7.48 (t, J = 2.7 Hz, 1H), 7.26 (d, J = 7.3 Hz, 1H), 6.79 (d, J = 8.3 Hz, 1H), 6.65-6.54 (m, 2H), 2.33 (s, 6H). (ESI+) m/z 381 (M + H)+ Retention time = 4.95 mins (method 1) |
| 167 | 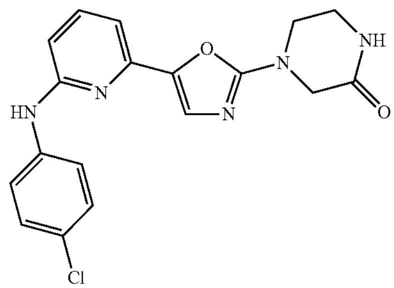 [SMILES: O=C1CN(c2ncc(-c3cccc(Nc4ccc(Cl)cc4)n3)o2)CCN1] | 4-{5-[6-(4-Chloro-phenylamino)-pyridin-2-yl]-oxazol-2-yl}-piperazine-2-one | (400 MHz, DMSO-$d_6$) δ 9.29 (s, 1H), 8.18 (s, 1H), 7.95-7.75 (m, 2H), 7.60 (t, J = 7.8 Hz, 1H), 7.46 (s, 1H), 7.41-7.25 (m, 2H), 6.98 (d, J = 7.4 Hz, 1H), 6.66 (d, J = 8.3 Hz, 1H), 4.07 (s, 2H), 3.86-3.61 (m, 2H), 3.40-3.33 (m, 4H). (ESI+) m/z 370 (M + H)+ Retention time = 3.36 mins (method 1) |
| 168 | 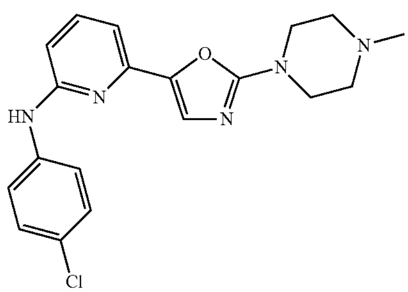 [SMILES: CN1CCN(c2ncc(-c3cccc(Nc4ccc(Cl)cc4)n3)o2)CC1] | (4-Chloro-phenyl)-{6-[2-(4-methyl-piperazin-1-yl)-oxazol-5-yl]-pyridin-2-yl}-amine | (400 MHz, DMSO-$d_6$) δ 9.24 (s, 1H), 7.81 (d, J = 8.7 Hz, 2H), 7.58 (t, J = 7.9 Hz, 1H), 7.41 (s, 1H), 7.32 (d, J = 8.7 Hz, 2H), 6.93 (d, J = 7.4 Hz, 1H), 6.65 (d, J = 8.2 Hz, 1H), 3.56-3.48 (m, 4H), 2.46-2.40 (m, 4H), 2.23 (s, 3H). (ESI+) m/z 370 (M + H)+ Retention time = 2.85 mins (method 1) |
| 169 | 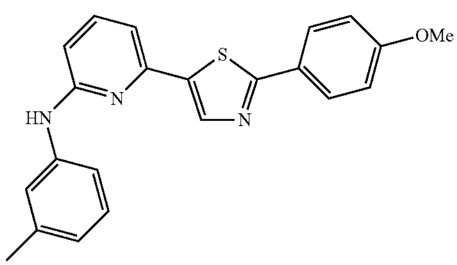 [SMILES: COc1ccc(-c2ncc(-c3cccc(Nc4cccc(C)c4)n3)s2)cc1] | {6-[2-(4-Methoxy-phenyl)-thiazol-5-yl]-pyridin-2-yl}-m-tolyl-amine | (300 MHz, DMSO-$d_6$) δ 9.16 (br s, 1H), 8.44 (s, 1H), 7.94 (d, J = 8.9 Hz, 2H), 7.79 (br s, 1H), 7.68-7.60 (m, 1H), 7.48 (d, J = 8.0 Hz, 1H), 7.37 (d, J = 7.3 Hz, 1H), 7.22 (t, J = 7.8 Hz, 1H), 7.10 (d, J = 8.9 Hz, 2H), 6.83-6.73 (m, 2H), 3.85 (s, 3H), 2.38 (s, 3H). (APCI+) m/z 374 (M + H). Retention time: 4.22 mins. (method 2) |
| 170 | 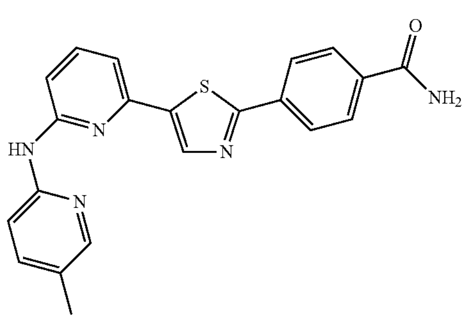 [SMILES: Cc1ccc(Nc2cccc(-c3cnc(-c4ccc(C(N)=O)cc4)s3)n2)nc1] | 4-{5-[6-(5-Methyl-pyridin-2-ylamino)-pyridin-2-yl]-thiazol-2-yl}-benzamide | (300 MHz, DMSO-$d_6$) δ 9.72 (br s, 1H), 8.59 (br s, 1H), 8.20-7.98 (m, 6H), 7.95 (d, J = 8.6 Hz, 1H), 7.78-7.70 (m, 1H), 7.66 (d, J = 8.8 Hz, 1H), 7.57-7.45 (m, 3H), 2.25 (s, 3H). (APCI+) m/z 388 (M + H). Retention time: 2.27 mins. (method 2) |

Example of In Vitro Proteine Kinase Inhibition Assays

Procedures
Flt-3 WT and Mutated Flt-3 Assay
Cell Lines

Ba/F3 human Flt-3 WT (Wild Type) and Flt-3 ITD (Internal Tandem Duplication) cell lines were derived from the murine IL-3 dependent Ba/F3 proB lymphoid cells. Ba/F3 human Flt-3 WT cells are grown in the presence of IL3, while Ba/F3 cells expressing human Flt-3 ITD are cytokine independent for their growth. The cell lines and human Flt-3 constructs were previously described (Casteran et al., Cell. Mol. Biol., 40, pp. 443-456, 1994). MV4-11 is a human leukemia cell lines derived from a patient with AML that express the mutant form Flt-3 ITD.

Cell-Based Proliferation and Viability Assay

Cell survival/proliferation assay (CellTiter-Blue Cell viability assay from Promega ref. G8081) was performed on all cell lines.

A total of $2.10^4$ cells/well/50 µl were seeded in a 96-wells plate. Treatment was initiated by addition of a 2× drug solution of ½ serial dilutions ranging from 0 to 10 µM. Cells were grown for 48 h at 37° C. and then incubated with 10 µl/well of CellTiter-Blue reagent for 4 h at 37° C. The assay is based on the conversion of resazurin to resorufin by metabolically active cells resulting in the generation of a fluorescent product. Fluorescence was measured following excitation at 544 nm and emission at 590 nm using a scanning multiwell spectrophotometer (POLARstar Omega, BMG labtech, France). A blank well without cells was used as a background control and all assays were performed in triplicates at least twice. The results are expressed as a percentage of the proliferation obtained in absence of treatment (DMSO control). All drugs were prepared as 20 mM stock solutions in DMSO and conserved at −80° C. Fresh dilutions were made in medium before each experiment.

Immunoprecipitation Assays and Western Blotting Analysis

For each assay, $5.10^6$ Ba/F3 Flt-3 ITD or MV4-11 cells were treated for 1 h30 with the indicated concentration of compounds according to table 1. Cells were collected, lysed and immunoprecipitated as described in Beslu et al., J. Biol. Chem., 271, pp. 20075-20081, 1996. Cell lysates were immunoprecipitated with rabbit immunsera directed against the Flt-3 (Santa Cruz SC-480). Western blots were hybridized either with the 4G10 anti-phosphotyrosine antibody (UBI) or with the rabbit immunsera anti-Flt-3. The membranes were then incubated either with HRP-conjugated goat anti-mouse IgG antibody or with HRP-conjugated goat anti rabbit IgG antibody (Immunotech). Proteins of interest were then visualized by incubation with ECL reagent (Amersham).

Syk Assay

SYK kinase was purified as a full length protein in a baculovirus system near homogeneity. JAKs kinases (JAK1, JAK2 and JAK3) were purchased either from Invitrogen or from Millipore. All kinases assays were performed with the Kinease TK (tyrosine kinase) HTRF (Homogeneous Time Resolved Fluorescence) assay developed by Cisbio international. These assays were carried out at room temperature in 96-wells half-area white plates in a final volume of 25 µl of kinase buffer (10 mM $MgCl_2$; 2 mM $MnCl_2$; 50 mM Sodium-HEPES pH 7.8; BRIJ-35 0.01%, 1 µM substrate) containing ATP at a concentration of at least twice the Km for each enzyme and an appropriate amount of recombinant enzyme to ensure a linear reaction rate. Reactions were initiated upon introduction of the enzyme and terminated with the addition of one reaction volume (25 µl) of HTRF detection buffer. Plates were incubated for one hour at room temperature and the time resolved Fluorescence resonance energy transfer signal was measured in a Pherastar FS microplate reader (BMG Labtech). All data are the average of triplicate results with a standard deviation<10%.

Experimental Results

The experimental results for various compounds according to the invention using above-described protocols are set forth at Table 2.

TABLE 2 in vitro inhibitions of various compounds against Flt-3 WT, Flt-3 ITD and/or Syk.

| Target | IC50 | Compounds of the invention (reference to the examples) |
|---|---|---|
| Flt-3 WT | IC50 < 1 µM | 005, 006, 007, 009, 018, 020, 024, 068 |
| | 1 µM < IC50 < 10 µM | 001, 010, 013, 014, 030 |
| Flt-3 ITD | IC50 < 1 µM | 003, 004, 005, 006, 007, 009, 010, 015, 016, 018, 020, 024, 036, 038, 052, 068, 069, 081, 085, 086, 095, 113, 131, 161, 155 |
| | 1 µM < IC50 < 10 µM | 001, 010, 013, 014, 034, 032, 037, 040, 074, 076, 119, 145, 152, 153, 159 |
| Syk | IC50 < 1 µM | 020, 045, 048, 056, 069, 080, 099, 118, 140 |
| | 1 µM < IC50 < 10 µM | 062, 064, 116, 120 |

IC50: Concentration inhibiting 50% of protein kinase receptors of the target cells.

Comments on the Experiments and Results

The inventors observed a very effective inhibition of a protein kinase, and in particular a tyrosine kinase, and more particularly of Flt-3 and/or Flt-3 ITD and/or syk by the class of compounds of formula I of the invention. The listed compounds in table 2 are well representing the class of compounds of formula I.

We claim:
1. A compound of formula I:

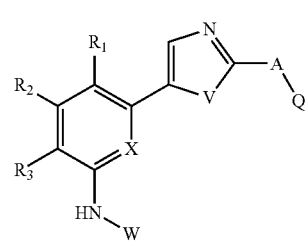

FORMULA I wherein substituents A, Q, X, R1, R2, R3, V and W in Formula I are defined as follows:

A is one of the following:
i) N(R4)(CH2)$_n$ where n is 0<n<3
ii) O(CH2)$_n$ where n is 0<n<3
iii) S(CH2)$_n$ where n is 0<n<3
iv) (CH2)$_n$ where n is 0≤n<4
v) C(O)(CH2)$_n$ where n is 0<n<3
vi) C(R4)=C(R5)
vii) C≡C R4 and R5 each independently are hydrogen, $C_{1-4}$alkyl, $C_{2-6}$alkenyl, $C_{2-6}$alkynyl, $C_{3-7}$cycloalkyl, $C_{1-4}$haloalkyl, $C_{1-4}$ alkoxy, $C_{1-4}$hydroxyalkyl, $C_{1-4}$ alkylamino;

X is CH or N;
V is O;
Q is selected from:
i) an alkyl$^1$ group, or
ii) an aryl$^1$ group, or
iii) an heteroaryl$^1$ group;

an alkyl$^1$ group is defined as a linear, branched or cycloalkyl group containing from 1 to 10 carbon atoms and optionally substituted with one or more hetereoatoms selected from halogen, oxygen, and nitrogen; trifluoromethyl, carboxyl, cyano, nitro, formyl; CO—R, COO—R, CONR—R', SO2-R, and SO2NR—R' wherein R and R' are a linear or branched alkyl group containing 1 to 10 carbon atoms and optionally substituted with at least one heteroatom selected from a halogen, oxygen, and nitrogen; and a cycloalkyl group;

an aryl$^1$ group is defined as phenyl or a substituted variant thereof bearing any combination, at any one ring position, of one or more substituents selected from
halogen;
an alkyl$^1$ group;
an aryl or heteroaryl group;
trifluoromethyl, O-alkyl, carboxyl, cyano, nitro, formyl, hydroxy, NH-alkyl, N(alkyl)(alkyl), and amino group;
NRCO—R' or NRCOO—R' or NRCONR'—R'' or NRSO2-R' or NRSO2NR'—R'' or CO—R or COO—R or CONR—R' or SO2-R or or SO2NRR' wherein R, R' and R'' each independently are selected from hydrogen, alkyl, aryl or heteroaryl group;

an heteroaryl$^1$ group is defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, benzoxazole, benzothiazole, quinolinyl group, which may additionally bear any combination, at any one ring position, of one or more substituents selected from
halogen;
an alkyl$^1$ group;
an aryl or heteroaryl group,
trifluoromethyl, O-alkyl, carboxyl, cyano, nitro, formyl, hydroxy, NH-alkyl, N(alkyl)(alkyl), and amino group;
NRCO—R' or NRCOO—R' or NRCONR'—R'' or NRSO2-R' or NRSO2NR'—R'' or CO—R or COO—R or CONR—R' or SO2-R or SO2NRR' wherein R, R' and R'' each independently are selected from hydrogen, alkyl, aryl or heteroaryl group;

R1, R2 and R3 each independently are selected from hydrogen, halogen, a linear or branched alkyl group containing from 1 to 10 carbon atoms and optionally substituted with one or more hetereoatoms selected from halogen, oxygen, and nitrogen; trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONR—R', SO2-R, and SO2NR—R' wherein R and R' corresponds to hydrogen, alkyl, aryl or heteroaryl group;

W is aryl$^1$ or heteroaryl$^1$.

2. A compound according to claim 1 of formula II:

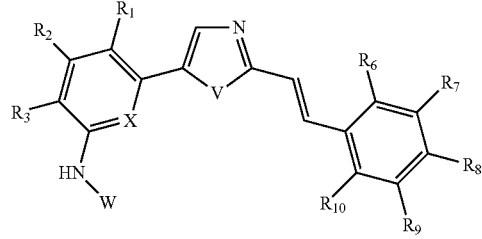

FORMULA II

Wherein R1, R2, R3, X, V and W have the meaning described in claim 1, and

Wherein R6, R7, R8, R9 and R10 each independently are selected from hydrogen, halogen, a linear or branched alkyl group containing from 1 to 10 carbon atoms and optionally substituted with one or more hetereoatoms selected from halogen, oxygen, and nitrogen; trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONR—R', SO2-R, and SO2NR—R' wherein R and R' each independently are selected from hydrogen, alkyl, aryl or heteroaryl group.

3. A compound according to claim 1 of formula III:

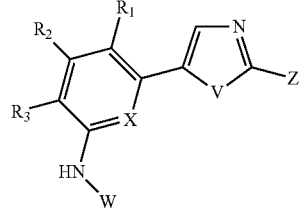

FORMULA III

Wherein Z is Aryl or heteroaryl$^1$, R1, R2, R3, X, V, W, Aryl$^1$ and heteroaryl$^1$ have the meaning described in claim 1.

4. The compound of claim 1 having the following formula Ia:

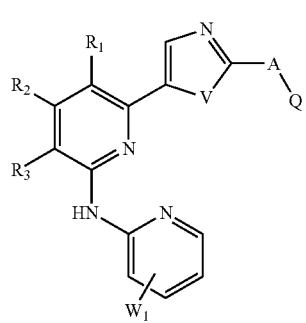

Formula Ia

Wherein, A, Q, R1, R2, R3, and V are as defined in claim 1, and W1 is selected from one or more of the following: hydrogen, halogen, a linear or branched alkyl group containing from 1 to 10 carbon atoms and optionally substituted with one or more hetereoatoms selected from halogen, oxygen, and nitrogen; trifluoromethyl, $C_{1-6}$alkyloxy, amino, $C_{1-6}$alkylamino, di($C_{1-6}$alkyl)amino, carboxyl, cyano, nitro, formyl, hydroxy, CO—R, COO—R, CONR—R', SO2-R, and SO2NR—R' wherein R and R' each independently are selected from hydrogen, alkyl, aryl or heteroaryl group.

5. The compound of claim 1 represented by formula IIa below:

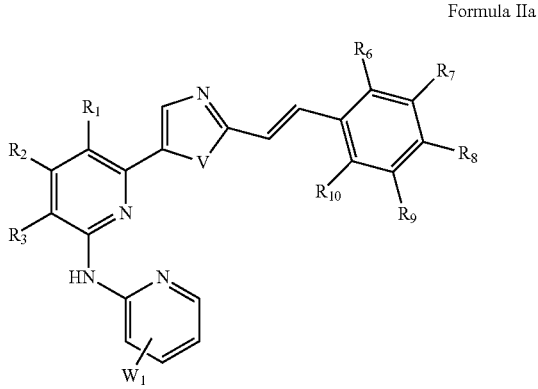

Formula IIa

Wherein, R1, R2, R3, R6, R7, R8, R9 and R10, V and W1 have the meaning described in claims 1 to 4.

6. The compound of claim 1 represented by formula IIIa below:

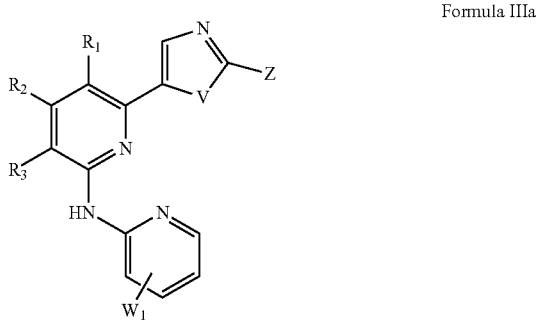

Formula IIIa

Wherein, R1, R2, R3, V, W1 and Z have the meaning described in claims 1 to 4.

7. A compound as claimed in claim 1 selected from:
(4-Methyl-pyridin-2-yl)-[6-(2-phenethyl-oxazol-5-yl)-pyridin-2-yl]-amine
(4-Methyl-pyridin-2-yl)-[3-(2-phenylsulfanyl-oxazol-5-yl)-phenyl]-amine
(3-{2-[2-(4-Methoxy-phenyl)-vinyl]-oxazol-5-yl}-phenyl)-(4-methyl-pyridin-2-yl)-amine
(6-{2-[2-(4-Methoxy-phenyl)-vinyl]-oxazol-5-yl}-pyridin-2-yl)-(4-methyl-pyridin-2-yl)-amine
(4-Methyl-pyridin-2-yl)-[6-(2-styryl-oxazol-5-yl)-pyridin-2-yl]-amine
Pyridin-2-yl-[6-(2-styryl-oxazol-5-yl)-pyridin-2-yl]amine
(6-{2-[2-(4-Methoxy-phenyl)-vinyl]-oxazol-5-yl}-pyridin-2-yl)-pyridin-2-yl-amine
(6-{2-[2,6-Dimethyl-4-(2-morpholin-4-yl-ethoxy)-phenyl]-oxazol-5-yl}-pyridin-2-yl)-(4-methyl-pyridin-2-yl)-amine
(5-Chloro-pyridin-2-yl)-[6-(2-phenyl-oxazol-5-yl)-pyridin-2-yl]-amine
(4-Methyl-piperazin-1-yl)-(3-{5-[3-(4-methyl-pyridin-2-ylamino)-phenyl]-oxazol-2-yl}-phenyl)-methanone
3-(4-Methyl-pyridin-2-ylamino)-5-(2-thiophen-3-yl-oxazol-5-yl)-benzonitrile
(4-Methyl-pyridin-2-yl)-{3-[2-(3-trifluoromethyl-phenyl)-oxazol-5-yl]-phenyl}-amine
4-(2-{5-[6-(4-Methyl-pyridin-2-ylamino)-pyridin-2-yl]-oxazol-2-yl}-vinyl)-benzonitrile
4-(2-{5-[6-(4-Methyl-pyridin-2-ylamino)-pyridin-2-yl]-oxazol-2-yl}-ethyl)-benzonitrile
(4-methyl-pyridin-2-yl)-[6-(2-pyridin-3-yl-oxazol-5-yl)-pyridin-2-yl]-amine
N-(2-Hydroxy-ethyl)-N-methyl-3-{5-[6-(4-methyl-pyridin-2-ylamino)-pyridin-2-yl]-oxazol-2-yl}-benzenesulfonamide
(4-methyl-pyridin-2-yl)-{6-[2-(3-pyrrolidin-1-ylmethyl-phenyl)-oxazol-5-yl]-pyridin-2-yl}-amine hydrochloride
(4-methyl-pyridin-2-yl)-{6-[2-(3-morpholin-4-ylmethyl-phenyl)-oxazol-5-yl]-pyridin-2-yl}-amine hydrochloride
(5-chloro-pyridin-2-yl)-[6-(2-thiophen-3-yl-oxazol-5-yl)-pyridin-2-yl]-amine
{6-[2-(1H-indol-5-yl)-oxazol-5-yl]-pyridin-2-yl}-pyrazin-2-yl-amine
{6-[2-(1H-indol-5-yl)-oxazol-5-yl]-5-methyl-pyridin-2-yl}-(4-methyl-pyridin-2-yl)-amine
[6-(2-Cylohexylsulfanyl-oxazol-5-yl)-pyridin-2-yl]-(4-methyl-pyridin-2-yl)-amine
5-[6-(4-methylpyridin-2-ylamino)pyridin-2-yl]-N-(pyridin-4-ylmethyl) oxazol-2-amine
N-(4-Methoxybenzyl)-5-[6-(4-methylpyridin-2-ylamino) pyridin-2-yl]oxazol-2-amine
4-{5-[6-(5-methyl-thiazol-2-ylamino)-pyridin-2yl]-oxazol-2-yl}-piperazine-2-one
{6-[2-(4-Methyl-piperazin-1-yl)-oxazol-5-yl]-pyridin-2-yl}-(3-trifluoromethyl-phenyl)-amine
(6-{2-[4-(2-Methoxy-ethyl)-piperazin-1-yl]-oxazol-5-yl}-pyridin-2-yl)-(4-methyl-pyridin-2-yl)-amine
1-(2-Methoxy-ethyl)-4-{5-[3-(4-methyl-pyrimidin-2-ylamino)-phenyl]-oxazol-2-yl}-piperazin-2-one
3-{2-[(2-methoxy-ethyl)-methyl-amino]-oxazol-5-yl}-5-(4-methyl-pyridin-2-ylamino)-benzonitrile
(4-Methyl-pyridin-2-yl)-[6-(2-pyridin-2-yl-oxazol-5-yl)-pyridin-2-yl]-amine
(4-Methyl-pyridin-2-yl)-[6-(2-phenyl-oxazol-5-yl)-pyridin-2-yl]-amine
(4-methyl-pyridin-2-yl)-(3-{2-[2-(3-trifluoromethyl-phenyl)-vinyl]-oxazol-5-yl}-phenyl)-amine
{6-[2-(2-Methoxy-pyridin-3-yl)-oxazol-5-yl]-pyridin-2-yl}-(4-methyl-pyridin-2-yl)-amine
3-{5-[6-(4-methyl-pyridin-2-ylamino)-pyridin-2-yl]-oxazol-2-yl}-1H-pyridin-2-one
3-{5-[6-(4-methyl-pyridin-2-ylamino)-pyridin-2-yl]-oxazol-2-yl}-1-(2-morpholin-4-yl-ethyl)-1H-pyridin-2-one
(4-Methyl-pyridin-2-yl)-[6-(2-phenylethynyl-oxazol-5-yl)-pyridin-2-yl]-amine
[6-(2-benzoxazole-2-yl-oxazol-5-yl)-pyridin-2-yl]-(4-methyl-pyridin-2-yl)-amine (4-Methyl-pyridin-2-yl)-(6-{2-[2-(2-morpholin-4-yl-ethoxy)-phenyl]-oxazol-5-yl}-pyridin-2-yl)-amine
{6-[2-(2-Methoxy-phenyl)-oxazol-5-yl]-pyridin-2-yl}-(4-methyl-pyridin-2-yl)-amine
(4-Methyl-pyridin-2-yl)-[6-(2-o-tolyl-oxazol-5-yl)-pyridin-2-yl]-amine
{6-[2-(2,6-Dimethyl-phenyl)-oxazol-5-yl]-pyridin-2-yl}-(4-methyl-pyridin-2-yl)-amine
4-{5-[6-(4-Methyl-pyridin-2-ylamino)-pyridin-2-yl]-oxazol-2-yl}-benzonitrile
(4-Methyl-pyridin-2-yl)-{6-[2-(3-trifluoromethyl-phenyl)-oxazol-5-yl]-pyridin-2-yl}-amine
(4-Methyl-pyridin-2-yl)-{6-[2-(4-trifluoromethyl-phenyl)-oxazol-5-yl]-pyridin-2-yl}-amine
(4-Methyl-piperazin-1-yl)-(3-{5-[6-(4-methyl-pyridin-2-ylamino)-pyridin-2-yl]-oxazol-2-yl}-phenyl)-methanone
{6-[2-(1H-Indol-5-yl)-oxazol-5-yl]-pyridin-2-yl}-(4-methyl-pyridin-2-yl)-amine
[6-(2-Furan-2-yl-oxazol-5-yl)-pyridin-2-yl]-(4-methyl-pyridin-2-yl)-amine
4-{5-[6-(3-Trifluoromethyl-phenylamino)-pyridin-2-yl]-oxazol-2-yl}-piperazin-2-one
{5-Methyl-6-[2-(4-methyl-piperazin-1-yl)-oxazol-5-yl]-pyridin-2-yl}-(4-methyl-pyridin-2-yl)-amine
4-{5-[3-Methyl-6-(4-methyl-pyridin-2-ylamino)-pyridin-2-yl]oxazol-2-yl}-piperazin-2-one
(4-Methyl-pyridin-2-yl)-[5-methyl-6-(2-thiophen-3-yl-oxazol-5-yl)-pyridin-2-yl]-amine
1-(2-Methoxy-ethyl)-4-{5-[3-methyl-6-(4-methyl-pyridin-2-ylamino)-pyridin-2-yl]-oxazol-2-yl}-piperazin-2-one
4-{5-[3-Fluoro-6-(4-methyl-pyridin-2-ylamino)-pyridin-2-yl]-oxazol-2-yl}-1-(2-methoxy-ethyl)-piperazin-2-one
4-{5-[3-Fluoro-6-(4-methyl-pyridin-2-ylamino)-pyridin-2-yl]-oxazol-2-yl}-piperazin-2-one
(5-Fluoro-6-{2-[4-(4-methyl-piperazin-1-yl)-phenyl]-oxazol-5-yl}-pyridin-2-yl)-(4-methyl-pyridin-2-yl)-amine
1-{5-[6-(Pyridin-2-ylamino)-pyridin-2-yl]-oxazol-2-yl}-piperidine-4-carboxylic acid amide
(4-Methyl-pyridin-2-yl)-[6-(2-thiophen-2-yl-oxazol-5-yl)-pyridin-2-yl]-amine
(4-Methyl-pyridin-2-yl)-[6-(2-thiophen-3-yl-oxazol-5-yl)-pyridin-2-yl]-amine
{6-[2-(2-Methoxy-4-methyl-pyridin-3-yl)-oxazol-5-yl]-pyridin-2-yl}-(4-methyl-pyridin-2-yl)-amine
{6-[2-(6-Methoxy-pyridin-3-yl)-oxazol-5-yl]-pyridin-2-yl}-(4-methyl-pyridin-2-yl)-amine
5-{5-[6-(4-Methyl-pyridin-2-ylamino)-pyridin-2-yl]-oxazol-2-yl}-1H-pyridin-2-one
3-{5-[6-(4-Methyl-pyridin-2-ylamino)-pyridin-2-yl]-oxazol-2-yl}-1-(2-pyrrolidin-1-yl-ethyl)-1H-pyridin-2-one
5-{5-[6-(4-Methyl-pyridin-2-ylamino)-pyridin-2-yl]-oxazol-2-yl}-1-(2-morpholin-4-yl-ethyl)-1H-pyridin-2-one
[6-(2-Benzofuran-2-yl-oxazol-5-yl)-pyridin-2-yl]-(4-methyl-pyridin-2-yl)-amine
(4-Methyl-pyridin-2-yl)-(6-{2-[2-(4-trifluoromethoxy-phenyl)-vinyl]-oxazol-5-yl}-pyridin-2-yl)-amine
{6-[2-(4-Methoxy-phenylethynyl)-oxazol-5-yl]-pyridin-2-yl}-(4-methyl-pyridin-2-yl)-amine
4-{5-[6-(4-Methyl-pyridin-2-ylamino)-pyridin-2-yl]-oxazol-2-ylethynyl}-benzonitrile
(4-Methyl-pyridin-2-yl)-[6-(2-pyrrolidin-1-yl-oxazol-5-yl)-pyridin-2-yl]-amine
(4-Methyl-pyridin-2-yl)-[6-(2-piperidin-1-yl-oxazol-5-yl)-pyridin-2-yl]-amine
(4-Methyl-pyridin-2-yl)-[6-(2-morpholin-4-yl-oxazol-5-yl)-pyridin-2-yl]-amine
4-{5-[6-(4-Methyl-pyridin-2-ylamino)-pyridin-2-yl]-oxazol-2-yl}-piperazin-2-one
(4-Methyl-pyridin-2-yl)-[6-(2-thiomorpholin-4-yl-oxazol-5-yl)-pyridin-2-yl]-amine
{6-[2-(4-Methyl-piperazin-1-yl)-oxazol-5-yl]-pyridin-2-yl}-(4-methyl-pyridin-2-yl)-amine
1-{5-[6-(4-Methyl-pyridin-2-ylamino)-pyridin-2-yl]-oxazol-2-yl}-piperidine-4-carboxylic acid amide
(4-Methyl-pyridin-2-yl)-{6-[2-(2-methoxyethylamino)oxazol-5-yl])-pyridin-2-yl}-amine
(4-Methyl-pyridin-2-yl)-{6-[2-(2-morpholin-4-yl-ethyl)-amino-oxazol-5-yl])-pyridin-2-yl}-amine
1-(2-Methoxy-ethyl)-4-{5-[6-(4-methyl-pyridin-2-ylamino)-pyridin-2-yl]-oxazol-2-yl}-piperazin-2-one
[6-(2-Cyclopentyl-sulfanyl-oxazol-5-yl)-pyridin-2-yl]-(4-methyl-pyridin-2-yl)-amine
(3-Methyl-pyridin-2-yl)-[6-(2-phenyl-oxazol-5-yl)-pyridin-2-yl]-amine
{6-[2-(1H-Indol-5-yl)-oxazol-5-yl]-pyridin-2-yl}-(3-methyl-pyridin-2-yl)-amine
(3-Methyl-pyridin-2-yl)-[6-(2-thiophen-3-yl-oxazol-5-yl)-pyridin-2-yl]-amine
(5-Methyl-pyridin-2-yl)-[6-(2-phenyl-oxazol-5-yl)-pyridin-2-yl]-amine
(5-Methyl-pyridin-2-yl)-[6-(2-thiophen-3-yl-oxazol-5-yl)-pyridin-2-yl]-amine
{6-[2-(1H-Indol-5-yl)-oxazol-5-yl]-pyridin-2-yl}-(5-methyl-pyridin-2-yl)-amine
(5-Methyl-pyridin-2-yl)-[6-(2-pyrrolidin-1-yl-oxazol-5-yl)-pyridin-2-yl]-amine
4-{5-[6-(5-Methyl-pyridin-2-ylamino)-pyridin-2-yl]-oxazol-2-yl}-piperazine-2-one
{6-[2-(4-Methyl-piperazin-1-yl)-oxazol-5-yl]-pyridin-2-yl}-(5-methyl-pyridin-2-yl)-amine
(4-Chloro-pyridin-2-yl)-[6-(2-thiophen-3-yl-oxazol-5-yl)-pyridin-2-yl]-amine
(4-Chloro-pyridin-2-yl)-{6-[2-(1H-indol-5-yl)-oxazol-5-yl]-pyridin-2-yl}-amine
(4-Chloro-pyridin-2-yl)-[6-(2-thiophen-2-yl-oxazol-5-yl)-pyridin-2-yl]-amine
(4-Chloro-pyridin-2-yl)-[6-(2-furan-2-yl-oxazol-5-yl)-pyridin-2-yl]-amine
(5-Chloro-pyridin-2-yl)-{6-[2-(1H-indol-5-yl)-oxazol-5-yl]-pyridin-2-yl}-amine
(5-Chloro-pyridin-2-yl)-[6-(2-pyrrolidin-1-yl-oxazol-5-yl)-pyridin-2-yl]-amine
4-{5-[6-(5-Chloro-pyridin-2-ylamino)-pyridin-2-yl]-oxazol-2-yl}-piperazine-2-one
(5-Chloro-pyridin-2-yl)-{6-[2-(4-methyl-piperazin-1-yl)-oxazol-5-yl]-pyridin-2-yl}-amine
(5-Chloro-pyridin-2-yl)-{6-[2-(2-methoxyethyl)-methyl-amino-oxazol-5-yl}-pyridin-2-yl}-amine
(4,6-Dimethyl-pyridin-2-yl)-[6-(2-phenyl-oxazol-5-yl)-pyridin-2-yl]-amine
(4,6-Dimethyl-pyridin-2-yl)-[6-(2-thiophen-3-yl-oxazol-5-yl)-pyridin-2-yd-amine
(4,6-Dimethyl-pyridin-2-yl)-{6-[2-(1H-indol-5-yl)-oxazol-5-yl]-pyridin-2-yl}-amine
(4,6-Dimethyl-pyridin-2-yl)-[6-(2-pyrrolidin-1-yl-oxazol-5-yl)-pyridin-2-yl]-amine 4-{5-[6-(4,6-Dimethyl-pyridin-2-ylamino)-pyridin-2-yl]-oxazol-2-yl}-piperazine-2-one
4-{5-[6-(4-Ethyl-pyridin-2-ylamino)-pyridin-2-yl]-oxazol-2-yl}-piperazine-2-one
2-{6-[2-(3-Oxo-piperazin-1-yl)-oxazol-5-yl]-pyridin-2-ylamino}-isonicotinonitrile
4-{5-[6-(5-Trifluoromethyl-pyridin-2-ylamino)-pyridin-2-yl]-oxazol-2-yl}-piperazine-2-one
4-{5-[6-(5-Trifluoromethyl-pyridin-2-ylamino)-pyridin-2-yl]-oxazol-2-yl}-piperazin-2-one
(6-{2-[2-(4-Methoxy-phenyl)-vinyl]-oxazol-5-yl}-pyridin-2-yl)-[4-(2-morpholin-4-yl-ethoxy)-pyridin-2-yl]-amine
(6-{2-[2-(4-Methoxy-phenyl)-vinyl]-oxazol-5-yl}-pyridin-2-yl)-(4-methyl-pyrimidin-2-yl)-amine
4-{5-[6-(Pyrazin-2-ylamino)-pyridin-2-yl]-oxazol-2-yl}-piperazine-2-one
4-{5-[6-(4-Methyl-thiazol-2-ylamino)-pyridin-2-yl]-oxazol-2-yl}-piperazine-2-one
{6-[2-(4-Methyl-piperazin-1-yl)-oxazol-5-yl]-pyridin-2-yl}-(4-methyl-thiazol-2-yl)-amine
(4-Methyl-pyridin-2-yl)-[3-(2-styryl-oxazol-5-yl)-phenyl]-amine
(3-{2-[2-(2,4-Difluoro-phenyl)-vinyl]-oxazol-5-yl}-phenyl)-(4-methyl-pyridin-2-yl)-amine
(4-Methyl-pyridin-2-yl)-[3-(2-thiophen-3-yl-oxazol-5-yl)-phenyl]-amine
{3-[2-(2,4-Dimethoxy-phenyl)-oxazol-5-yl]-phenyl}-(4-methyl-pyridin-2-yl)-amine
{3-[2-(1H-Indol-5-yl)-oxazol-5-yl]-phenyl}-(4-methyl-pyridin-2-yl)-amine
1-{5-[3-(4-Methyl-pyridin-2-ylamino)-phenyl]-oxazol-2-yl}-piperidine-4-carboxylic acid amide
(4-Methyl-pyridin-2-yl)-[3-(2-morpholin-4-yl-oxazol-5-yl)-phenyl]-amine
(4-Methyl-pyridin-2-yl)-(3-{2-[(pyridin-2-ylmethyl)-amino]-oxazol-5-yl}-phenyl)-amine
[3-(2-Benzylamino-oxazol-5-yl)-phenyl]-(4-methyl-pyridin-2-yl)-amine
4-{5-[3-(4-Methyl-pyrimidin-2-ylamino)-phenyl]-oxazol-2-yl}-piperazine-2-one
{3-[2-(4-Methyl-piperazin-1-yl)-oxazol-5-yl]-phenyl}-(4-methyl-pyrimidin-2-yl)-amine
(4,6-Dimethyl-pyridin-2-yl)-{3-[2-(1H-indol-5-yl)-oxazol-5-yl]-phenyl}-amine
3-(4-Methyl-pyridin-2-ylamino)-5-[2-(3-oxo-piperazin-1-yl)-oxazol-5-yl]-benzonitrile
3-[2-(4-Methyl-piperazin-1-yl)-oxazol-5-yl]-5-(4-methyl-pyridin-2-ylamino)-benzonitrile
4-{5-[3-(4-Methyl-pyridin-2-ylamino)-5-trifluoromethoxy-phenyl]-oxazol-2-yl}-piperazin-2-one
{3-[2-(4-Methyl-piperazin-1-yl)-oxazol-5-yl]-5-trifluoromethoxy-phenyl}-(4-methyl-pyridin-2-yl)-amine
4-{5-[4-Methyl-3-(4-methyl-pyridin-2-ylamino)-phenyl]-oxazol-2-yl}-piperazin-2-one
{5-[2-(1H-Indol-5-yl)-oxazol-5-yl]-2-methyl-phenyl}-(4-methyl-pyridin-2-yl)-amine
4-[5-(6-m-Tolylamino-pyridin-2-yl)-oxazol-2-yl]-piperazine-2-one
{6-[2-(4-Methyl-piperazin-1-yl)-oxazol-5-yl]-pyridin-2-yl}-m-tolylamine
(6-{2-[(2-Methoxy-ethyl)-methyl-amino]-oxazol-5-yl}-pyridin-2-yl)-m-tolylamine
(3,5-Dimethyl-phenyl)-{6-[2-(1H-indol-5-yl)-oxazol-5-yl]-pyridin-2-yl}-amine
4-{5-[6-(4-Chloro-phenylamino)-pyridin-2-yl]-oxazol-2-yl}-piperazine-2-one
(4-Chloro-phenyl)-{6-[2-(4-methyl-piperazin-1-yl)-oxazol-5-yl]-pyridin-2-yl}-amine
(4-Methyl-pyridine-2-yl)-[6-{2-[3-(2-morpholin-4-yl-ethoxy)-phenyl]-oxazol-5-yl}-pyridine-2-yl]-amine.

8. A pharmaceutical composition comprising a compound according to claim 1.

9. A cosmetic composition for tropical administration comprising a compound according to claim 1.

10. A method for treating a protein kinase related disease or disorder in a subject comprising administration to the subject an effective amount of a compound of Formula I according to claim 1.

11. A pharmaceutical composition comprising an effective amount of a combination of a compound according to claim 1 and another molecularly targeted agent.

12. A method for treating hematological malignancies, myeloproliferative disorder, other proliferative disorders, autoimmune disorders and skin disorders, comprising simultaneously or sequentially administering to a human or animal subject in need thereof a compound according to claim 1 in combination with another molecularly targeted agent, in sufficient amounts to provide a therapeutic effect.

13. The compound according to claim 1, wherein X is CH.

14. A method according to claim 10, where the protein kinase is a tyrosine kinase.

15. A method according to claim 14, where the protein kinase is an Flt-3 and/or syk.

* * * * *